US012797185B2

(12) United States Patent
Piunova et al.

(10) Patent No.: US 12,797,185 B2
(45) Date of Patent: Nov. 17, 2026

(54) LIGHT ADJUSTABLE INTRAOCULAR LENSES WITH A CAGED PHOTOINITIATOR

(71) Applicant: RxSight, Inc., Aliso Viejo, CA (US)

(72) Inventors: Victoria Piunova, Los Gatos, CA (US); David Joshua Dibble, Tustin, CA (US); Ilya Goldshleger, Ladera Ranch, CA (US); John Kondis, Irvine, CA (US); Christian Sandstedt, Pasadena, CA (US)

(73) Assignee: RxSight, Inc., Aliso Viejo, CA (US)

( * ) Notice: Subject to any disclaimer, the term of this patent is extended or adjusted under 35 U.S.C. 154(b) by 322 days.

(21) Appl. No.: 18/242,206

(22) Filed: Sep. 5, 2023

(65) Prior Publication Data

US 2024/0398551 A1 Dec. 5, 2024

Related U.S. Application Data

(60) Provisional application No. 63/505,840, filed on Jun. 2, 2023.

(51) Int. Cl.
*A61F 2/16* (2006.01)
*A61L 27/18* (2006.01)
(Continued)

(52) U.S. Cl.
CPC .............. *A61F 2/1659* (2013.01); *A61F 2/16* (2013.01); *A61L 27/18* (2013.01); *A61L 27/26* (2013.01);
(Continued)

(58) Field of Classification Search
CPC ...................... A61F 2/1659; A61F 2/16; A61F 2002/1696; A61F 2002/16965;
(Continued)

(56) References Cited

U.S. PATENT DOCUMENTS

| | | | |
|---|---|---|---|
| 6,450,642 | B1 | 9/2002 | Jethmalani et al. |
| 6,851,804 | B2 | 2/2005 | Jethmalani et al. |

(Continued)

FOREIGN PATENT DOCUMENTS

| | | | |
|---|---|---|---|
| WO | 2014/141019 | A1 | 9/2014 |

OTHER PUBLICATIONS

Tasdelen et al., "Benzodioxinone Photochemistry in Macromolecular Science: Progress, Challenges, and Opportunities" in ACS Macro Letters 2017, 6, pp. 1392-1397 which was submitted by applicant in form 1449 (Year: 2017).*

Bailey, J. et al., Switchable Liquid Crystal Contact Lenses for the Correction of Presbyopia, Crystals, vol. 8, publication 29, Jan. 12, 2018, doi:10.3390/cryst8010029, pp. 1-24; p. 2, second paragraph.

(Continued)

*Primary Examiner* — Blessing M Fubara

(57) ABSTRACT

Light Adjustable Lenses are described with a caged photoinitator and advanced polymerization control that greatly suppress unintended optical power drift in these lenses. Some Light Adjustable Lenses comprise a polymer silicone network, molded in the presence of a mobile macromer and an ultraviolet absorber; and a cage-photoinitiator complex; wherein a caged photoinitiator can be freed from a cage by a first photon of a first illumination; the free photoinitiator can be activated by a second photon of a second illumination; and the activated photoinitiator is capable of inducing a polymerization reaction of the mobile macromer, leading to a changing of an optical power of the LAL.

25 Claims, 27 Drawing Sheets

(51) Int. Cl.

| | |
|---|---|
| ***A61L 27/26*** | (2006.01) |
| ***A61L 27/48*** | (2006.01) |
| ***A61L 27/50*** | (2006.01) |
| ***C08K 5/132*** | (2006.01) |
| ***G02B 1/04*** | (2006.01) |
| ***G02B 1/14*** | (2015.01) |

(52) U.S. Cl.

CPC ............... *A61L 27/48* (2013.01); *A61L 27/50* (2013.01); *C08K 5/132* (2013.01); *G02B 1/041* (2013.01); *G02B 1/14* (2015.01); *A61F 2002/1696* (2015.04); *A61F 2002/16965* (2015.04); *A61F 2002/1699* (2015.04); *A61L 2430/16* (2013.01)

(58) Field of Classification Search

CPC ............. A61F 2002/1699; A61L 27/18; A61L 27/26; A61L 27/48; A61L 2430/16; A61L 27/50; C08K 5/132; G02B 1/041; G02B 1/14

See application file for complete search history.

(56) References Cited

U.S. PATENT DOCUMENTS

| | | | | |
|---|---|---|---|---|
| 9,119,710 | B2 | 9/2015 | Grubbs et al. | |
| 11,266,495 | B2 | 3/2022 | Goldshleger et al. | |
| 2002/0016629 | A1* | 2/2002 | Sandstedt ................ | G02B 1/04 623/6.58 |
| 2014/0038103 | A1 | 2/2014 | Miller | |

OTHER PUBLICATIONS

Pourshaban, E. et al., Flexible and Semi-Transparent Silicon Solar Cells as a Power Supply to Smart Contact Lenses, ACS Applied Electronic Materials, vol. 4, No. 8, Aug. 1, 2022, https://doi.org/10.1021/acsaelm.2c00665, pp. 4016-4022; abstract; p. 4018, figure 2.

Zhang, R., et al., Advanced liquid crystal-based switchable optical devices for light protection applications: principles and strategies. Light: Science and Applications, vol. 12, publication 11, Jan. 3, 2023, https://doi.org/10.1038/s41377-022-01032-y, pp. 1-30; entire publication.

Hung, T. L., et al., "Benzophenone derivatives as novel organosoluble visible light Type II photoinitiators for UV and LED photoinitiating systems", J. Polymer Science, 2020, 58, pp. 2914-2925.

Schneider, M.H., et al., "Benzophenone Absorpotion and Diffusion in Poly (dimethylsiloxane) and Its Role in Graft Photo-polymerization for Surface Modification", Langmuir, 2011, 27(3), pp. 1232-1240.

Tasdelen, M.A., et al., "Photochemically masked benzophenone: Photoinitiated free radical polymerization by using benzodioxinone", Polymer, 2006, 47, pp. 7611-7614.

Tasdelen, M.A., et al., "Benzodioxinone Photochemistry in Macromolecular Science: Progress, Challenges, and Opportunities", ACS Macro Letters, 2017, 6, pp. 1392-1397.

Tretinnikov, O.N., et al., "Benzophenone-Initiated Grafting Photopolymerization of Acrylic Acid on the Surface of Polyethylene from the Monomer Aqueous Solution without Its Deaeration", Polymer Science, Series B, 2012, vol. 54, Nos. 9-10, pp. 427-433.

Khudyakov and Turro, "Cage Effect Dynamics under Photolysis of Photoinitiators", Designed Monomers and Polymers 13(5):487-496; DOI:10.1163/138577210X521378.

* cited by examiner

Example 1

| | |
|---|---|
| cage-PI complex 200 | benzodioxinone |

| | |
|---|---|
| free PI 206a | benzophenone |

Example 3

| cage-PI complex 200 |
| --- |
| 5-hydroxy-2-(naphthalenyl)-2 phenyl-4H-benzo-dioxinone |

| free PI 206a |
| --- |
| 2-naphthalenyl (phenyl)methanone |

Example 5 cage-PI complex 200

2-(4-(diphenylamino)phenyl)-5-hydroxy-2-phenyl-4H-benzo[d][1,3]dioxinone free PI 206a 4-diphenylamino benzophenone

LIGHT ADJUSTABLE INTRAOCULAR LENSES WITH A CAGED PHOTOINITIATOR

This application claims priority from and thus benefit of U.S. Provisional Application 63/505,840, entitled: "Light Adjustable Intraocular Lenses with Advanced Polymerization Control", to I. Goldshleger et al., filed on Jun. 2, 2023, the entire application incorporated by reference herein.

TECHNICAL FIELD

This invention relates to light adjustable lenses, and in more particular to advanced control techniques of the polymerization process in these lenses.

BACKGROUND

The techniques of cataract surgery are progressing at an impressive pace. Generations of phacoemulsification platforms and more recently introduced surgical lasers keep increasing the precision of the placement of intraocular lenses (IOLs) and keep reducing unintended medical outcomes. Nevertheless, after the IOLs have been implanted, the postsurgical healing process can shift or tilt the IOLs in a notable fraction of the patients, leading to a diminished visual acuity, and a deviation from the planned surgical outcome.

A new technique has been developed recently to correct or mitigate such a postsurgical IOL shift or tilt. The IOLs can be fabricated from a photo-polymerizable material, henceforth making them Light Adjustable Lenses, or LALs. In the days after the surgery, the implanted LALs may shift and tilt, eventually settling into a postsurgical position different from what the surgeon planned, just like all other Intraocular lenses, or IOLs. However, unlike other IOLs, once the LAL settled, a Light Delivery System (LDD) can be used to illuminate the LALs with an illumination beam profile that induces photopolymerization in the LAL with a pre-determined spatial profile, thereby changing the refractive properties of the LALs. This refractive change adjusts the LAL optical performance to compensate the unintended postsurgical shift or tilt of the LAL. This adjustment procedure is followed by a lock-in procedure, whose function is to deactivate all remaining photopolymerizable materials.

In a limited percent of cases, the lock-in procedure may not deactivate all photopolymerizable material. Subsequent exposure of this remaining fraction of the photopolymerizable material to sunlight may cause an additional, undesirable drift of the optical power of the LAL. Therefore, there is a need for advanced polymerization control techniques to limit, or eliminate, the undesirable optical power drift in LALs.

SUMMARY

Light Adjustable Lenses (LALs) that address the above challenges can comprise various polymer control designs, processes and techniques, as described next.

Some Light Adjustable Lenses (LAL) are comprising a polymer silicone network, infused with a mobile macromer, a non-switchable ultraviolet absorber, and a photoinitiator; and a front protection layer, including a switchable ultraviolet absorber; wherein the LAL is light adjustable by a shaped illumination activating the photoinitiator which induces a polymerization of the mobile macromer, thereby changing an optical power of the LAL; the LAL is capable of accommodating an oxygen concentration in the range of 0.5-20 ppm; and a ratio R of the oxygen concentration [O2] times an oxygen-driven photoinitiator quench rate kq over a mobile macromer concentration [MM] times a photoinitiator-driven polymerization add rate ka, R=kq[O2]/ka[MM], is greater than 10.

In some Light Adjustable Lenses, the front protection layer includes a non-switchable ultraviolet absorber.

In some Light Adjustable Lenses, the LAL includes a radical scavenger or an anti-oxidant.

In some Light Adjustable Lenses, the mobile macromer is monofunctional.

In some Light Adjustable Lenses, the mobile macromer is sterically hindered.

In some Light Adjustable Lenses, the photoinitiator is switchable between a protected state and an activatable state.

In some Light Adjustable Lenses, chemical compositions, concentrations and reaction rates of the silicone network, the mobile macromer, the switchable and non-switchable ultraviolet absorber and the photoinitiator are such that during a light adjustment procedure a slope of a time dependent power adjustment curve increases by a factor of two or more after a t (activate) time, wherein t (activate) is in a range of 3 seconds-100 seconds.

In some Light Adjustable Lenses, the photoinitiator is anchored to the polymer silicone network.

In some Light Adjustable Lenses, the photoinitiator is capable of becoming an activated photoinitiator upon absorbing an UV photon; and the activated photoinitiator is capable of activating a mobile macromer by activating its endgroup.

In some Light Adjustable Lenses, the activated endgroup of the mobile macromer is capable of forming a bond with a second mobile macromer, activating an endgroup of the second mobile macromer in the process.

In some Light Adjustable Lenses, a reaction of the activated photoinitiator with oxygen creates a low activity photoinitiator derivative.

In some Light Adjustable Lenses, a reaction of the activated mobile macromer with oxygen creates a low activity compound; and the LAL includes a radical scavenger that is capable of reacting with the low activity compound to turn it into a deactivated compound.

Some Light Adjustable Lenses comprise a polymer silicone network, molded in the presence of a mobile macromer and an ultraviolet absorber; and a cage-photoinitiator complex; wherein a caged photoinitiator can be freed from a cage by a first photon of a first illumination; the free photoinitiator can be activated by a second photon of a second illumination; and the activated photoinitiator is capable of inducing a polymerization reaction of the mobile macromer, leading to a changing of an optical power of the LAL.

DETAILED DESCRIPTION

Figures 1A, 1B, 1C:
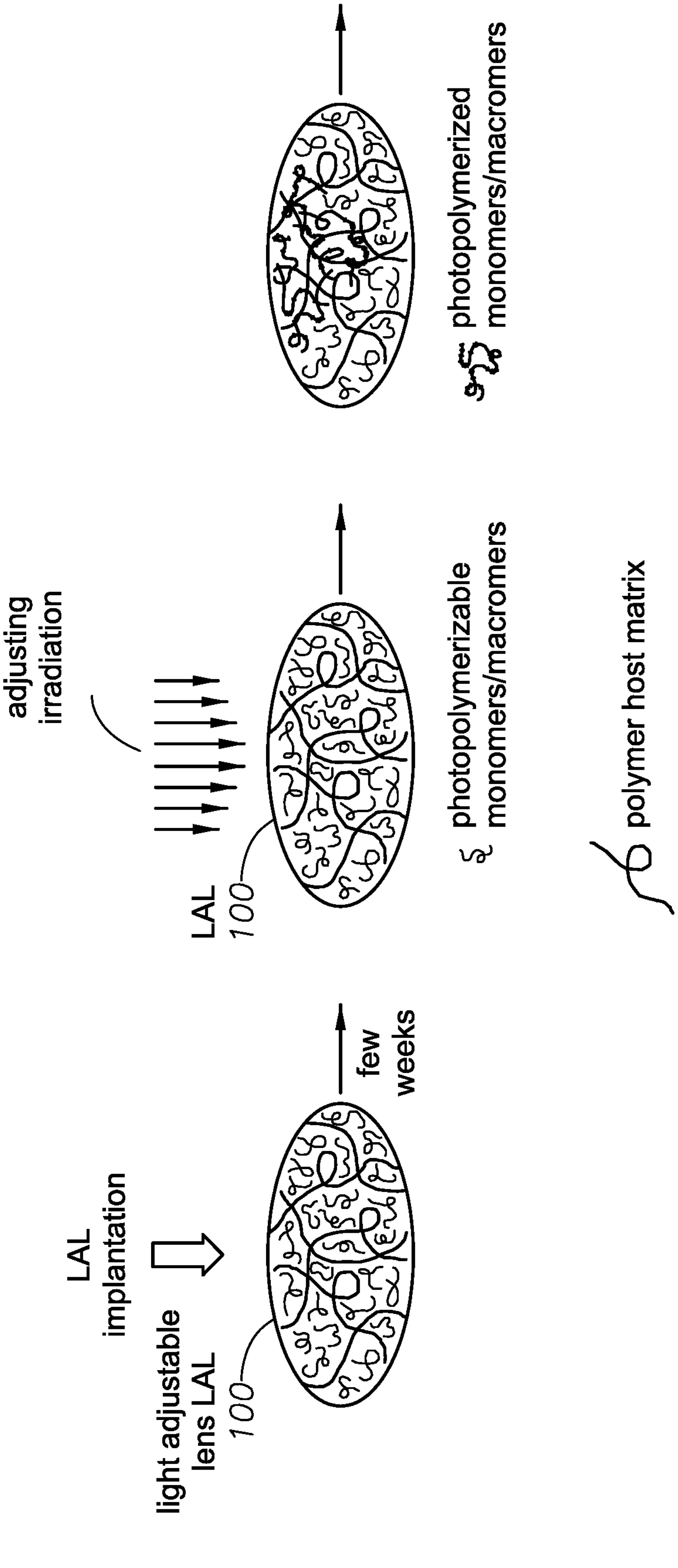
FIGS. 1A-F illustrate the steps of light adjustment in a Light Adjustable Lens (LAL 100).
Figures 1D, 1E, 1F:
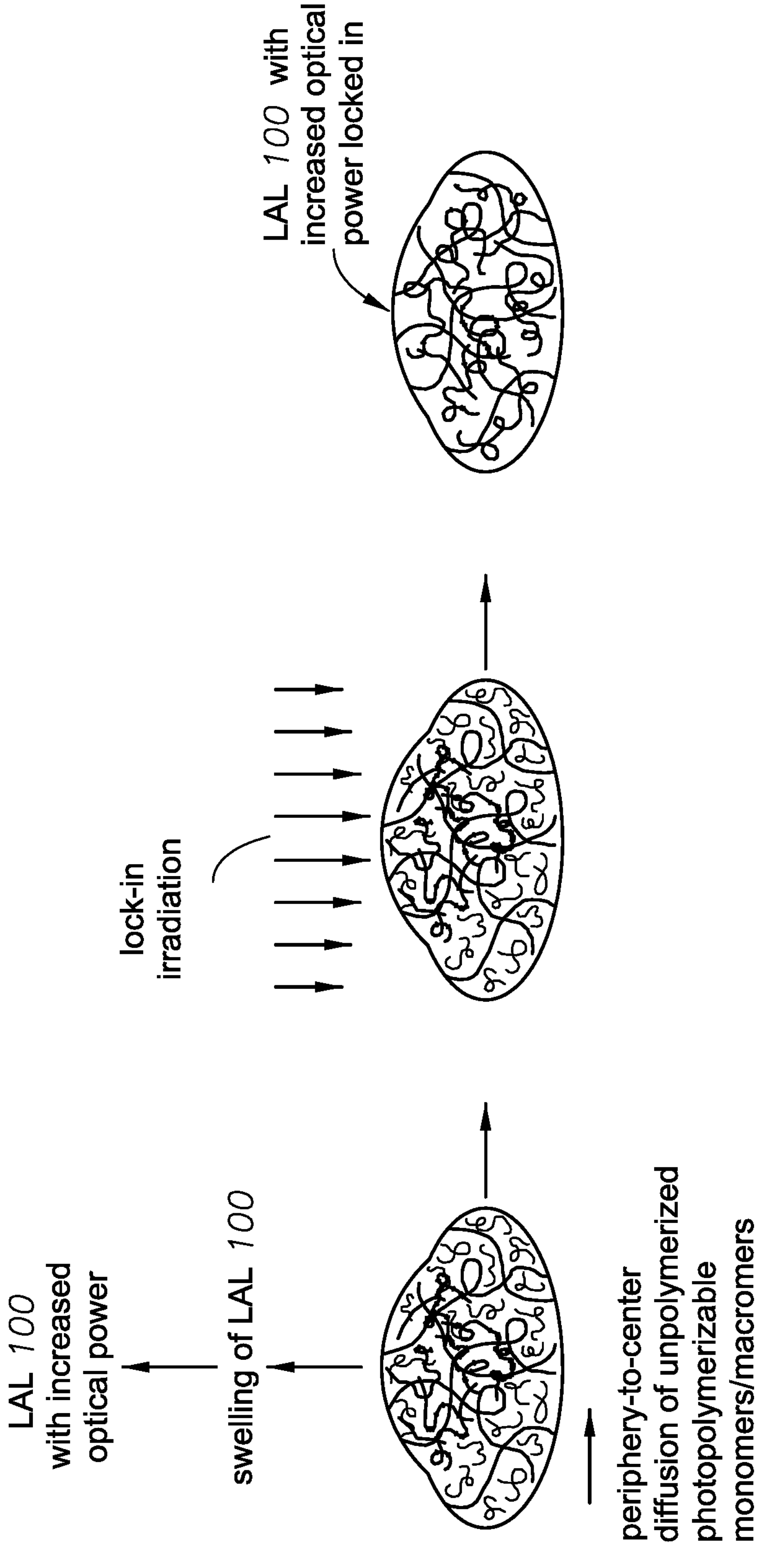

The central step of the cataract surgery is the implantation of the Intra Ocular Lens, the IOL. The ophthalmologist uses refined and time-tested calculations to choose the IOL with the optimal optical characteristics and positions the IOL with extreme care in the capsule. After the implantation, the IOL settles in the eye as the scars and the incisions heal, and the ophthalmic tissue reacts to the surgical procedure and the implantation. This typically takes weeks and often results in the IOL shifting and/or tilting away from its implanted location. Thus, in spite of careful preparations and informed choices by the ophthalmologist, these shifts and tilts can move the focal point of the IOL off the retina, resulting in the deterioration of the patient's visual acuity. Traditional IOLs have a fixed shape and optical properties, and so the patient has to live with this deteriorated visual performance, e.g., by wearing corrective glasses. Some ophthalmologists perform LASIK surgeries to correct these unintended shifts. In contrast, if a Light Adjustable Lens, or LAL 100 was implanted into the patient's eye, once the LAL 100 settled, the ophthalmologist can determine how to adjust the shape of the LAL 100 in order to compensate its shift and tilt. This adjustment is achieved by irradiating the LAL 100 with a UV beam whose beam profile is selected to achieve this shape adjustment.

FIGS. 1A-F illustrate that the LAL 100 is capable of such shape change because its silicone polymer network has been infused (1) with photoinitiator molecules that can be activated by an incoming UV illuminating beam; and (2) with mobile macromers, which the activated photoinitiators can induce to bond to the polymer network, or to each other. Once the mobile macromers bond to the network, they become immobile. This creates a chemical potential difference for the remaining mobile macromers that forces their diffusion from the peripheral, higher concentration regions to the central regions where their concentration has been depleted by the photoinduced immobilizing polymerization. This diffusion, or drift, of the mobile macromers to the central irradiated regions causes the swelling of the LAL 100, which in turn modifies its optical characteristics to re-optimize the visual acuity for the patient. This chemistry of the LALs 100 will be described in more detail shortly.

Once the adjustment has been performed, the remaining photoinitiators and mobile macromers are deactivated by a subsequent "lock-in" procedure, where a "lock-in" UV radiation is applied with a sufficiently high intensity to consume all, or essentially all of them.

In order to ensure that indeed all photo activatable compounds are deactivated, it is typical to perform two lock-in procedures, separated by a few days. However, requiring the patients to return to the clinic for two lock-in procedures after the original implantation and the subsequent optical power adjustment places substantial burden on both the patient and the doctor. Therefore, modifying the chemistry of these light adjustable lenses 100 to reduce the number of necessary lock-in procedures from two to one would offer major improvements for the overall convenience and acceptance of the light adjustable lens technology, in effect bringing its medical benefits to a much larger number of patients. It is important though that the modified lens chemistry still ensures that the single lock-in procedure consumes essentially all photo-active compounds, and enables the sufficient stabilization of the lens and thus prevents any subsequent unintended photo-induced drift of the optical properties.

Since the retina is very sensitive to UV irradiation, the first generation of the LALs 100 included UV absorbers distributed in their bulk, as well as a strongly UV-absorbing back layer. These UV absorbers already prevented the adjusting and the lock-in UV irradiation damaging the retina. As an additional safety measure, in order to prevent the UV content of the sunlight from inducing unintended optical adjustments in the LAL 100 from the implantation until the lock-in, patients are instructed to wear UV-blocking sunglasses.

Figure 2A:
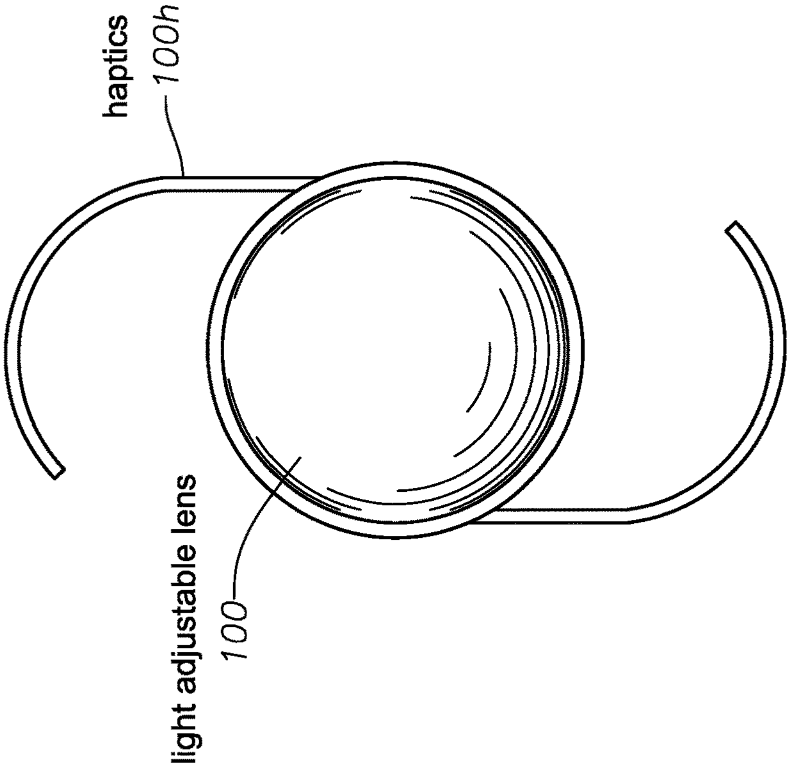
FIGS. 2A-B illustrate a Light Adjustable Lens (LAL) with a front protection layer and a back protection layer.
Figure 2B:
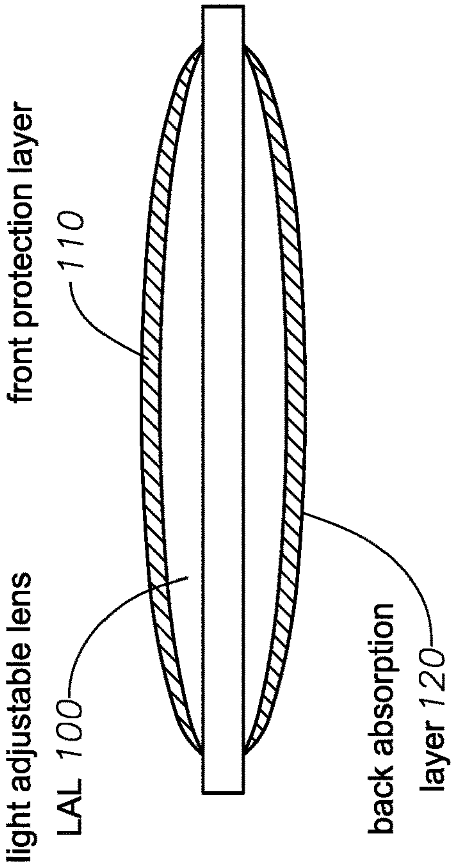

FIGS. 2A-B show that recent upgrades of the LAL 100 introduced an additional, front protection layer 110. FIG. 2A is a top view of these upgraded LALs 100 that also shows that the LAL 100 is stabilized in the capsulary bag of the eye after implantation with the help of haptics 100*h*. FIG. 2B is a side view of the LAL 100 that shows the new front protection layer 110, and the previous back protection layer 120. This front protection layer 110 includes a switchable UV absorber that can switch between a strongly UV-absorbing configuration and a weakly UV-absorbing configuration. Such a switchable front protection layer 110 provides good UV protection in its strongly absorbing configuration to prevent unintended optical adjustments before the lock-in, while it can be switched to its weakly absorbing configuration to allow the UV light to enter the LAL 100 during the adjustment and the lock-in procedures. Its chemistry will be described in detail later. These upgraded lenses have been widely implanted in patients, and after two lock-in procedures they exhibit completely satisfactory optical stability with no perceptible changes in their optical properties.

In the process of searching for one-lock-in lens chemistries, laboratory experiments showed that in rare circumstances one-lock-in lenses can face potential challenges. Some of these challenges are called “zone formation” and “power drift”, both leading to unwanted changes of the optical power of the LAL 100 at times other than the adjustment or lock-in procedure. As it will be described in detail below, these unwanted changes of the optical power can be induced by at least two classes of processes. The faster, zone formation change can be induced primarily by the UV component of ambient/natural light between the implantation and the lock-in of the LAL 100, when the LAL 100 still contains a substantial amount of photoinitiators and mobile macromers. Zone formation may be caused by UV exposure of relatively short duration, an example being a patient inadvertently looking at the sun without the required sunglasses, possibly while playing outdoors sports, or using a UV tanning machine.

Power drift, the other class of power-changing processes, is primarily driven by chemical reactions that were started by a low intensity ambient UV light, but are sustained by spontaneous chemical reactions that progress without further UV illumination. This self-sustaining power drift happens much more slowly, but can continue over a long time, possibly even after the first lock-in process at a lower rate. As mentioned, the new generation of LAL 100_s_ have an added switchable front protection layer 110 whose primary function is to protect against zone formation. This front protection layer 110 has the potential to eliminate the need for wearing sunglasses between implantation and lock-in—a clear advantage. However, this same front protection layer 110 hinders the consumption of the macromers and photoinitiators during the lock-in process. Therefore, some percent of the macromers and photoinitiators may remain activatable even after the first lock-in and thus can sustain the chemical reactions that lead to a power drift. Further, the switchable front protection layer 110 and the distributed UV absorber still allow a very low percentage of UV photons to get into the bulk of the LAL 100. Some of these UV photons can be absorbed by the remaining activatable photoinitiators in the central exposed region. This UV absorption by activatable photoinitiators can initiate additional self-sustaining chemical reactions, primarily unintended polymerization. Both of these mechanisms lead to a slow power drift of the optical power of the LAL 100. Realistic ambient light exposure experiments with single lock-in experimental lenses indicated the possibility of such a power drift with a magnitude of about 0.1 D-0.2 D over several hundreds of hours after the single lock-in.

In response to the above challenges, the present application primarily describes chemical considerations and designs to suppress and minimize this long-time slow power drift in the new generation of LALs 100, with the eventual goal of creating optically stable single lock-in light adjustable lenses.

In addition, it is noted that lens chemistries that reduce the long-time power drift, caused by the self-sustaining unintended polymerization after the first lock-in, can also reduce zone formation at short times, before the first lock-in. Preventing short-time zone formation with such new lens chemistries would eliminate the need to require patients to wear sunglasses until the first lock-in, and thus would enhance control over outcomes, patient comfort, and acceptance of the light adjustable lens technology, thus bringing the medical benefits to a larger number of patients.

To set the stage, the chemistry of the Light Adjustable Lenses is described in greater detail next. The LAL 100 is formed from two polymerizable formulations: the silicone lens matrix, or network, formulation, and the photoreactive formulation. Many details of these formulations were described in U.S. Pat. No. 6,450,642, titled: “Lenses capable of post-fabrication power modification” to Jethmalani et al, hereby incorporated by reference in its entirety. In some embodiments, the silicone lens matrix can include a silicone polymer, such as a vinyl capped siloxane copolymer, even more particularly, the shown divinyl polydimethyl diphenyl siloxane copolymer:

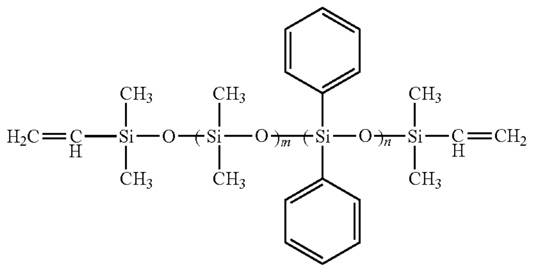

where n and m can be in the 2-100 range, in some embodiments in the 2-30 range. The composition, or concentration, of this silicone copolymer can be in the 20%-70% range, in some cases in the 30%-60% range.

The other component of the network formulation can be a wide variety of multi-vinyl functional silicone resins. One example is shown here:

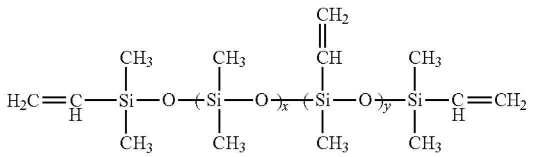

where x and y can be in the 2-100 range, in some embodiments in the 2-30 range. The composition of this silicone resin can be in the 10%-50% range, in some cases, in the 20%-40% range.

These two components can be linked into a silicone lens network 101 with a variety of crosslinkers XLK 102, such as multi-hydrosilane functionals, with an example shown here:

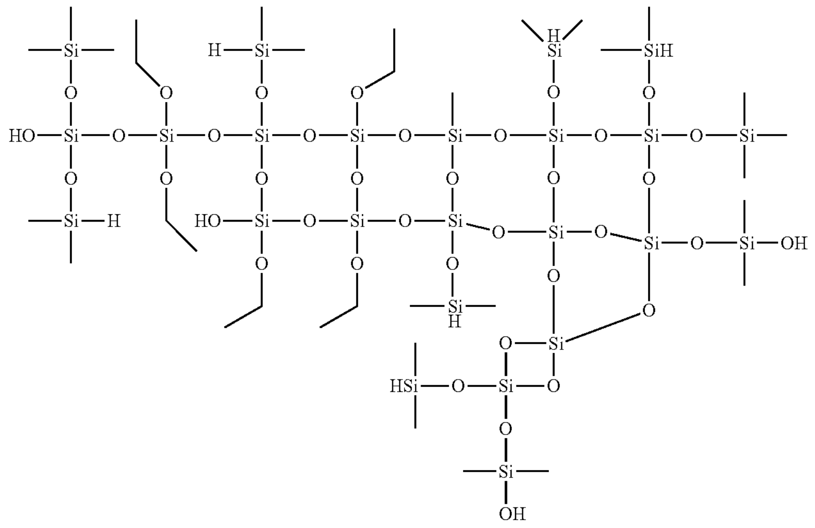

The composition of the cross-linker XLK 102 can be in the 1%-10% range, in some cases, in the 3%-7% range. These cross-linkers XLK 102 can link the siloxane polymers together by a catalyst-assisted hydrosilation polymerization process into the silicone network 101 as part of a curing process. The curing is performed at a low temperature to ensure that the photoreactive formulation remains photoreactive. This polymerization process creates the large, interconnected silicone network 101, or matrix, described briefly earlier. This polymer network 101 is immobile because of its huge size and because the large number of its branches prohibit mobility. It forms the backbone of the LAL 100 and largely determines its mechanical and optical properties.

Figure 3:
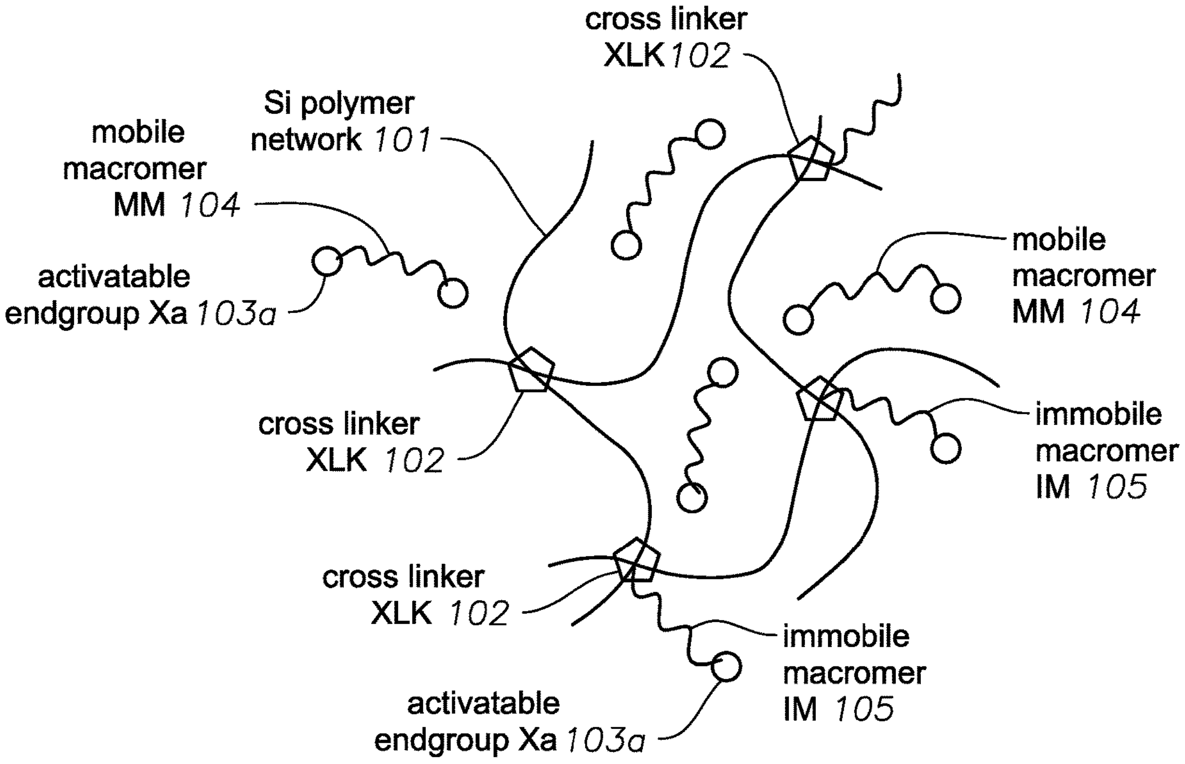
FIG. 3 illustrates primary compounds and structures in the LAL 100.

The photoreactive formulation can include a variety of acrylate endcapped siloxane macromers, an example being the shown polydimethyl siloxane, with methacrylate endgroups:

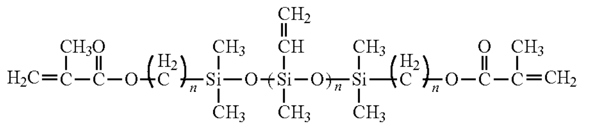

where n and x can be in the 2-100 range, in some cases, in the 2-30 range. These macromers are often shorter than the previously described siloxane copolymers and silicone resins, and are not linked to the silicon network 101 either, and are therefore mobile. The composition of these mobile macromers can be in the 20%-50% range, in some cases, in the 30%-40% range. Importantly, the methacrylate end groups are photoactivatable via their activatable end group (or endcap) 103, as described further below. These macromers are also impacted by the curing process, but only partially. A fraction of them gets linked to the cross-linkers XLK 102 during the hydrosilation process of the curing at one of their methacrylate endcaps 103 and thus become immobilized macromers themselves. At the same time, the other methacrylate endgroup 103 of these immobilized macromers retains its photoactivity. The remaining fraction of these macromers remains untethered to the network 101 and thus remain mobile. These will be referred to as Mobile Macromers 104, or MMs 104. The macromers that got linked to crosslinkers will be referred to as (one type of) Immobilized Macromers 105, or IMs 105. The resulting structure of the polymerized silicone network 101 with IMs 105 linked at the crosslinkers XLK 102. while MMs 104 remaining mobile is shown in FIG. 3.

The photoinitiator 106, or PI 106, can be a wide variety of known photoinitiators. Some embodiments of photoinitiators include x-alkylbenzoins having the general formula or structure:

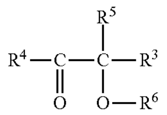

wherein R3 is H, alkyl radical, aryl radical, substituted alkyl, or substituted aryl radical, and R4 is H, alkyl radical, aryl radical, substituted alkyl or substituted aryl radical; R5 and R6 are phenyl or substituted phenyl allyl or allyloxy. Specific examples of R3 and R4 groups include methyl, phenyl trifluoropropyl, ethyl and cyano propyl. Phenyl substituents from the R5 and R6 groups may include alkyl, alkoxy, halogen, alkaryl, cyano alkyl, haloalkyl and N,N dialkyl amino.

Also useful are photoinitiators 106 having one or more UV initiators bonded to a short polymer backbone or segment. This photoinitiator 106 has the general formula: A-B-A1, wherein A and A1 may be the same or different UV initiators and B is a short polymer segment comprising from 2 to 28 monomer moieties. In general, the photoinitiator 106 tends to have the same polymer backbone as that used for the network of the LAL 100. For example, for LALs 100 fabricated from silicone polymer, the short polymer linking the initiators can also be a silicone polymer. Likewise, where the LAL 100 is polyacrylate based, the short polymer chain can be a polyacrylate.

In one embodiment, the photoinitiators 106 comprise one or more UV initiators attached to a polysiloxane bridge and having the general formula:

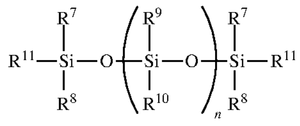

where R7 through R11 are independently selected from the group consisting of hydrogen, alkyls (primary, secondary, tertiary, cyclo), aryl or heteroaryl moieties and n is an integer from 2 to 28 and where at least one moiety R7-R11 is a UV initiator. In preferred embodiments, R7-R11 are C1-C10 alkyl or phenyl with methyl most preferred, but at least one can be hydrogen.

Particularly useful photoinitiators 106 include benzoyl peroxide (left), and benzoin (right):

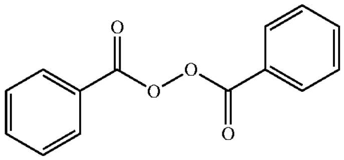

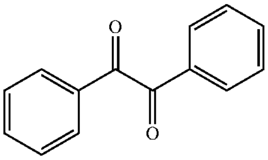

The incoming UV photons break, or cleave, the central O—O bond in benzoyl peroxide and the central C—C bond in benzoin. A particularly useful photoinitiator 106 is BLAB, which includes benzoyl as shown. "L4" codes the four-times repeated silicone dimethyl unit.

effective to execute this cleaving. Photons with wavelengths in a 10-20 nm range around 365 nm can also be used. Electrons in a highly reactive state, the radical center, will be denoted by *, and the compounds that are transformed into radicals by these electrons are also denoted by *. The below figure shows the photocleavage process of the BL4B photoinitiator 106 into two radicals (step (1)):

(1)

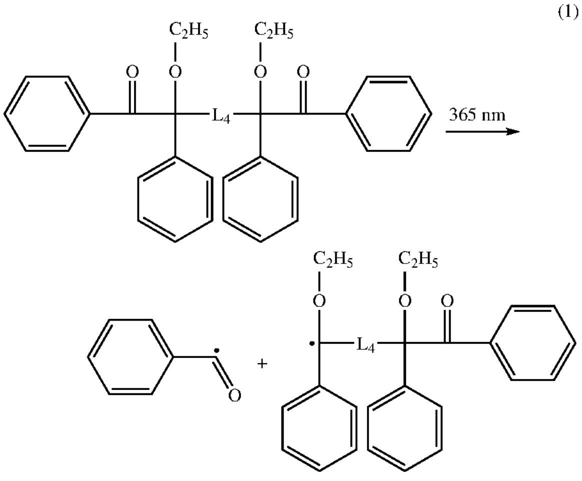

Figure 4:
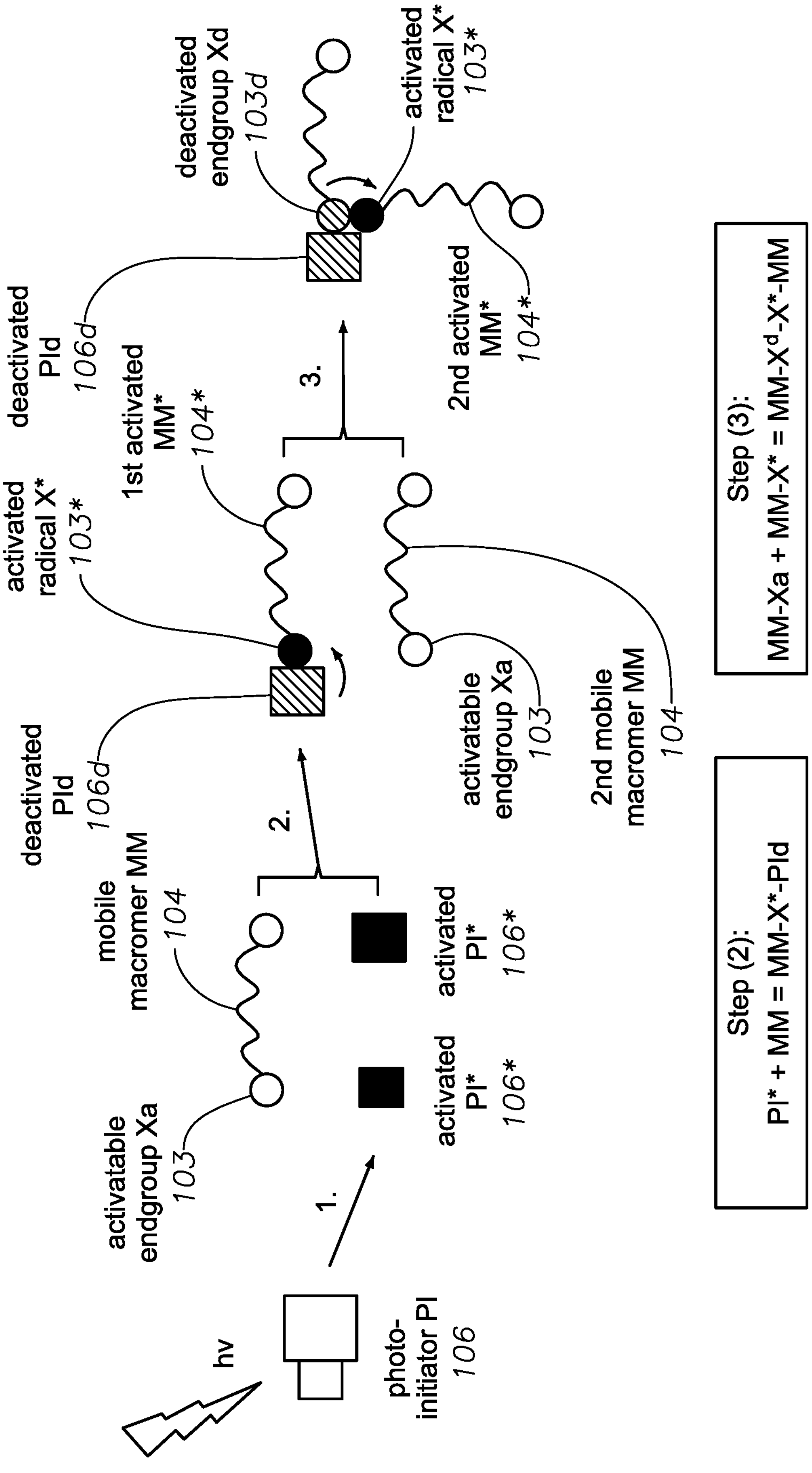
FIG. 4 illustrates steps of the photoinduced interaction between mobile macromers and the photoinitiator.

FIG. 4 shows the process of photoactivated poly . . . ization on a symbolic level in three steps. Step (1) is the just-described photo-cleaving: the incident photon cleaves the PI 106 into two groups. (Equations with "s" will be used for the symbolic representation of the corresponding chemical reaction: Eq. (1s) to symbolically represent the reaction of Eq. (1), etc.):

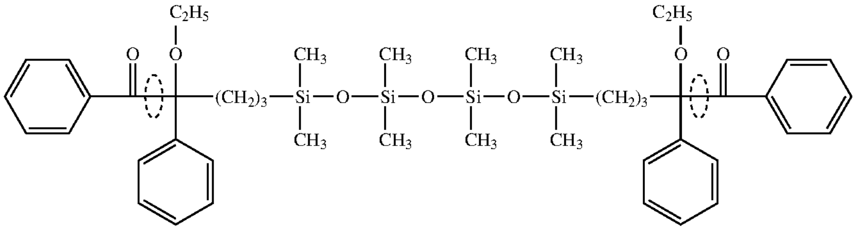

BL4B 842

The BLAB PI 106 is bifunctional in the sense that it has two photocleavable bonds, shown with the two ellipses. In general, when the PI 106 absorbs a UV photon, it often breaks, or cleaves, into two highly reactive radicals. The probability of this process is called the quantum yield. BLAB breaks into a benzoyl radical and a group with a ketyl radical at the end, as shown below. Each of these radicals has a radical center: an electron in a highly reactive state.

With these preparations, we describe the photoactivated polymerization with chemical reaction equations on a particular example, as well as on a symbolic level. Following widely used notations, UV photons will be denoted by hv, indicating their frequency v multiplied by Planck's constant h. The number "365" next to hv indicates an approximate wavelength of the photon, in nanometers, that is most $$PI + h\nu = 2PI^*. \quad (1s)$$

Both PI groups are activated in the sense that both have an electron excited into a highly reactive state, and thus forms radicals, both of which will be denoted by PI* 106* for simplicity. The uneven sizes of the two squares in FIG. 4 capture the uneven sizes of the two groups.

Step (2) shows that each activated PI* 106* group can react with a MM 104, which activates the MM in the sense that the reaction transfers the highly reactive electron state onto the MM's endgroup, transforming it into a radical. The full reaction reads as follows (step (2)):

(2)

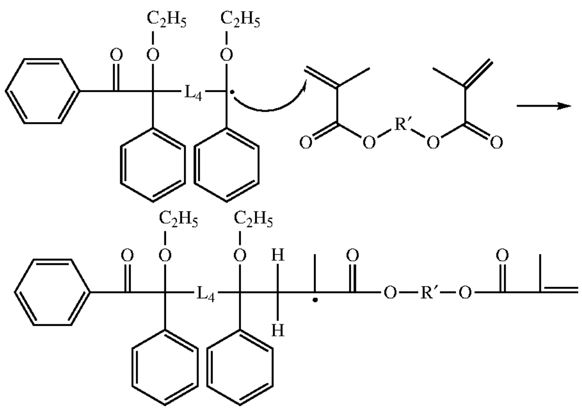

The highly reactive electron of the PI* 106*, its radical center, breaks the double bond between the central carbon atom of the methacrylate endgroup and the CH2 in this process. The electron of the CH2 group forms a bond with the radical center of the PI* 106*, deactivating it into a deactivated PId 106*d* (shown with shading) and bonding it to the MM 104. Remarkably, the same reaction promotes the other electron from the double bond into a highly reactive state, forming a new radical center on the central carbon. FIG. 4 indicates these processes of step (2) symbolically.

The methacrylate endgroup 103 of the MM 104, with the double bond broken and one of its electrons being promoted into a highly reactive state, will be referred to as a "radical X*", or "activated radical X*", or "activated endgroup 103*". In the Figures, open symbols refer to pre-reaction groups (activatable endgroup 103, PI 106), solid symbols refer to activated groups (activated radical X* 103*, activated PI* 106*), and shaded symbols refer to deactivated groups (deactivated endgroup (Xd) 103*d*, deactivated PId 106*d*). The endgroup 103 transforming into the radical X* activates MM 104 into an activated MM* 104*, where the activated radical will be shown sometimes explicitly as MM-X*. The symbolic representation of the above reaction takes the form (step (2)):

$$PI^* + MM = MM^*{-}PId \equiv MM{-}X^*{-}PId \quad (2s)$$

where on the right the deactivated PId is shown in the endproduct, and the identity (≡) on the right simply introduces a shorter and a longer notation for the same activated mobile macromer with an activated endgroup expressly shown (MM-X*), or only implied (MM*).

FIG. 4 also shows that the activation of MM 104 into MM-X* 104* in step (2) made it ready for a polymerization reaction with a second MM 104 in a subsequent step (3) via the reaction:

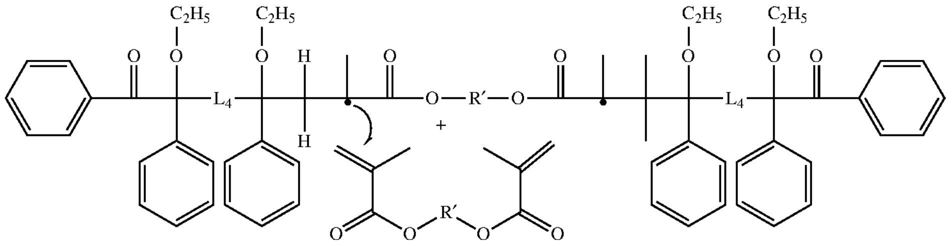

which results in the two MMs 104 bound into a final state:

(3)

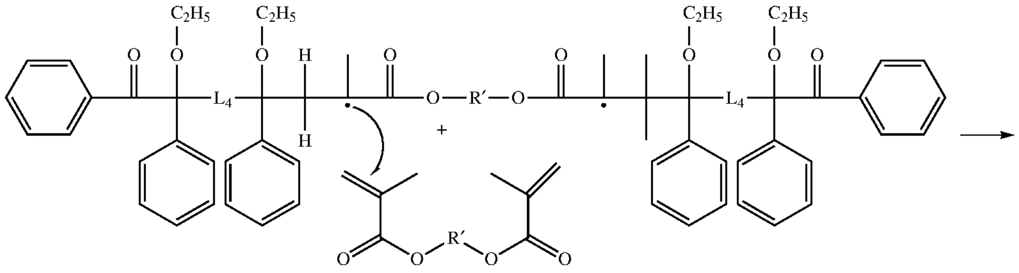

-continued

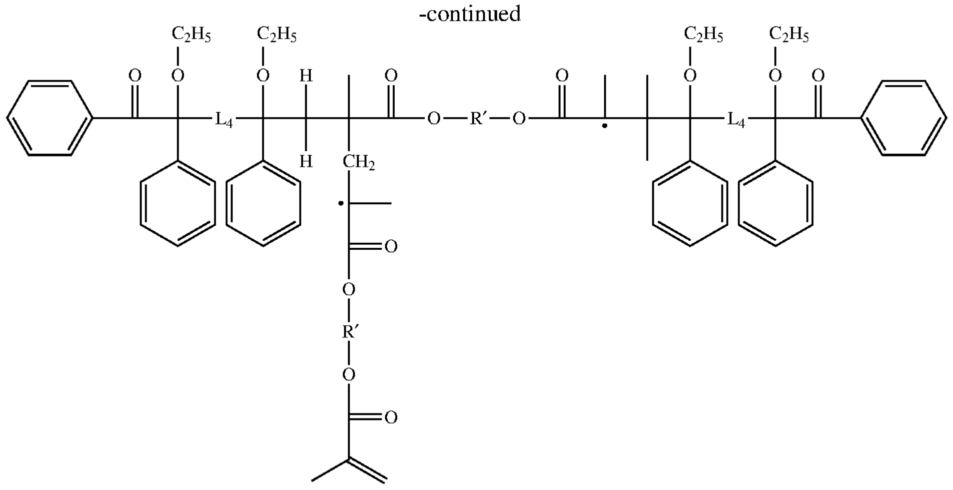

This polymerization, or bonding step (3) transfers the highly reactive electron state from the first activated MM-X* 104* to the second MM 104. Accordingly, polymerization step (3) deactivates the activated radical X*/endgroup 103* of the first MM-X* into a deactivated endgroup (Xd) 103*d*, while it activates the second MM into a MM-X* with its own radical center. This transfer of step (3) in FIG. 4 can be described symbolically as:

$$MM\text{-}X^* + MM = MM\text{-}MM\text{-}X^* \quad (3s)$$

In a more detailed representation, the activatable endgroup is denoted by Xa or 103*a*, and the deactivated endgroup is denoted by Xd or 103*d*. With this, the above polymerization step (3) can be written in more detail as:

$$MM\text{-}X^* + MM\text{-}Xa = MM\text{-}Xd\text{-}X^*\text{-}MM. \quad (3s')$$

We will use these two notations interchangeably. In reactions when in step (2), the activated photoinitiator PI* 106* activated an activatable endgroup Xa 103*a* at the end of an immobile macromer IM 105 into a IM-X*, then the polymerization step (3) takes the form:

$$MM\text{-}Xa + IM\text{-}X^* = IM\text{-}Xd\text{-}X^*\text{-}MM. \quad (3s'')$$

In the detailed step (3) above an MM 104 was shown that had two activatable endgroups 103, both of them activated by PI*s 106*, and thus had activated radicals on both of its two ends: X*-MM-X*. Such MMs 104 are sometimes called bifunctional for this reason. The step (3) MM-MM bonding/polymerization reaction involved only one of these radicals. This reaction leaves the bifunctional MM still capable of entering into a second polymerization reaction through its other radical X* 103*. Such bifunctional MMs 104 that can polymerize at both of their endgroups are capable of rapidly growing a multi-branched polymer network, as described next.

Figure 5A:
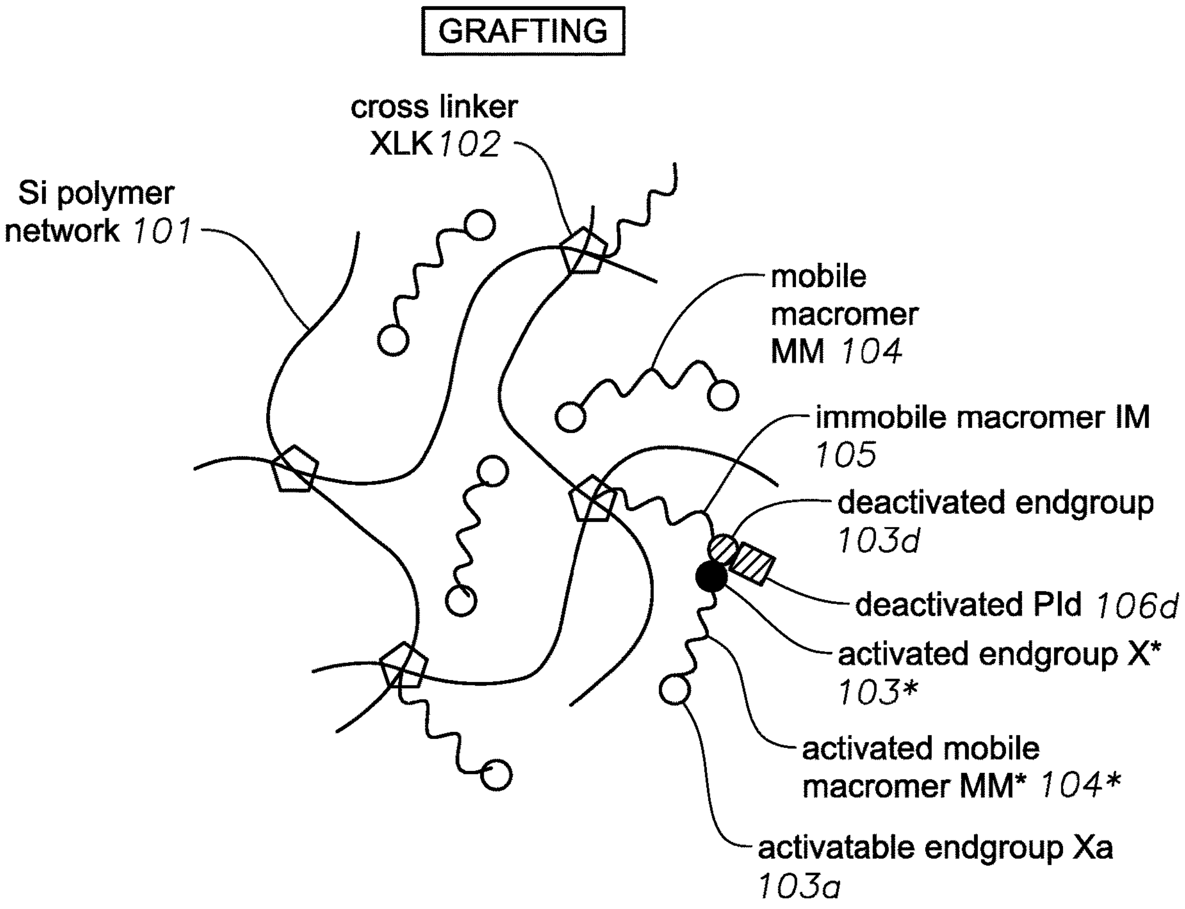
FIGS. 5A-C illustrate the two pathways to immobilizing mobile macromers.
Figure 5B:
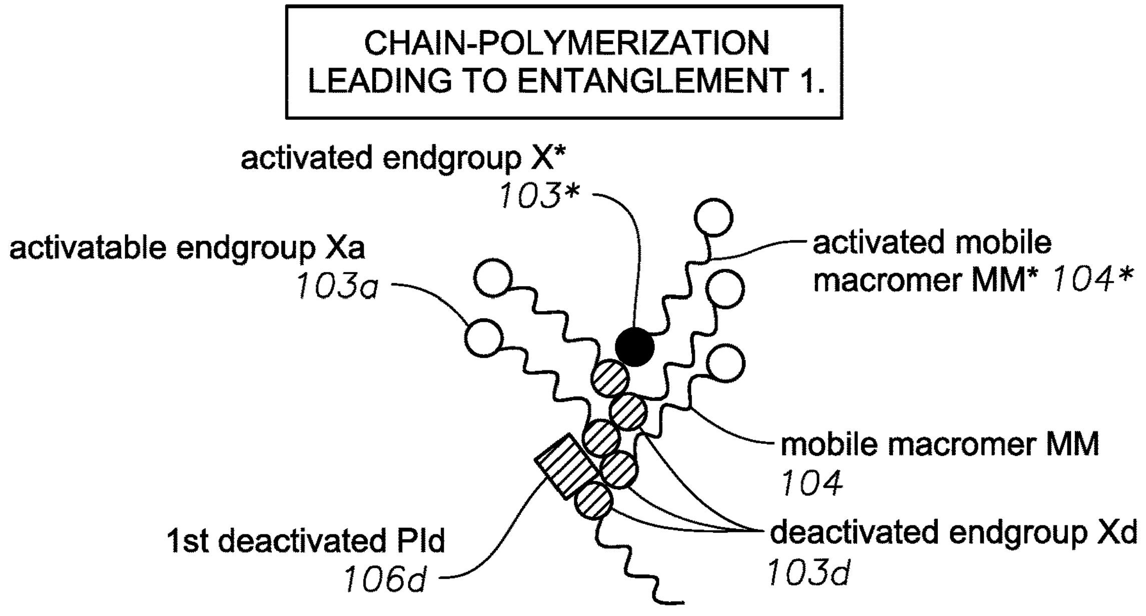
Figure 5C:
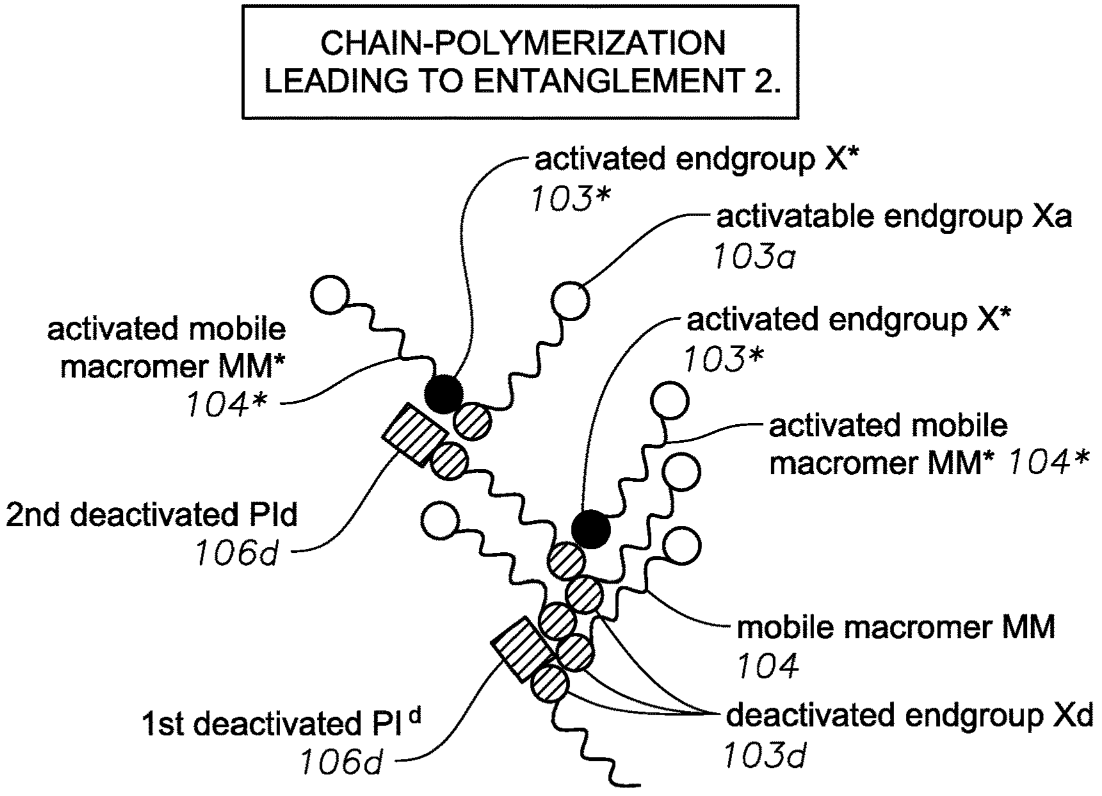

FIGS. 5A-C show that this 3-step photoinduced bonding/polymerization of two MMs 104 tends to immobilize them. The immobilization of mobile macromers MM 104 is, of course, the driver of the change of the optical power, as demonstrated in FIG. 1. FIG. 5A shows the first mechanism for this immobilization. It is recalled that the LAL 100 has two types of Macromers: Mobile Macromer MMs 104 that are free to move through the network 101, and Immobile Macromer IMs 105 which got linked to the crosslinkers XLK 102 of the silicone network 101 already during the molding/curing and are therefore immobilized. FIG. 5A shows a photoinduced bonding of a mobile MM 104 to an already immobile IM 105, induced by an activated PI* 106. Referring back to FIG. 4, in step (2), the activated PI* 106* can activate the activatable endgroup 103*a* of the IM 105, turning it into IM* 105*. In the subsequent polymerization step (3), a nearby MM 104 can bond to the activated IM* 105*. This step (3) deactivates the immobile macromer IM 105 into a deactivated IM 105*d* and transfers the radical center onto the MM 104 to transform it to an activated MM* 104*. In a sister reaction, in step (2) the activated PI* 106* could activate a MM 104 into a MM* 104*, and in the subsequent step (3), the MM* 104* can bond to an IM 105, which deactivates the MM 104 and activates the IM 105 into a IM* 105*. Both processes result in a MM 104 being bonded to the IM 105, their complex having an activated endgroup 103*. Bonding to the immobile macromer IM 105 naturally immobilizes the mobile macromer MM 104 as well. This process is often called "grafting", since the MMs 104 graft onto the Si polymer network 101. Grafting is induced by UV illumination activating PI 106 into PI* 106*, which then grafts a MM 104 onto the Si polymer network. As such, this UV-induced grafting is a primary driver of the relatively fast zone formation.

FIG. 5B shows the second mechanism of immobilization: a photoinduced bonding of a mobile MM 104 to another mobile MM-X* 104*, activated by a PI* 106*. FIG. 4 showed that the result of this process is that the first, activated MM-X* 104* gets deactivated into a MM-Xd 104*d*, while the second activatable MM-Xa 104*a* becomes a newly activated MM-X* 104. This bonding/polymerization step (3) can repeat again and again without repeated activation by additional photoactivated PIs* 106*. This is the previously mentioned self-sustaining polymerization process that keeps repeating itself without repeated absorption of UV photons. This process is sometimes called chain-polymerization. Since chain-polymerization can repeat itself without activating additional photoinitiators PI 106 beyond the original PI 106 that originally nucleated this cluster of MMs 104, it can continue spontaneously without UV light in a spontaneous, self-sustaining manner. Its speed is lower though that that of the initial, PI*-induced step (2), because the reactivity, or reaction rate of the UV-activated, PI*-induced step (2) is considerably faster than the reactivity of the chain-polymerization.

FIG. 5B shows that a single initial photoinduced activation of a PI 106 can nucleate a development of a network of increasing number of MMs 104 along a zig-zag backbone. FIG. 5C shows that in embodiments where the MM 104 is bifunctional, see Eq. (3), a side-branch can be nucleated by a second photoactivated PI*s 106*, and further side-branches by further photoactivated PI*s 106*. The resulting complex cluster, or network, of MMs 104 rapidly increases in size and can develop many complex branches. Because of the cluster's growing size, the probability of it entangling with the silicone network 101 increases, and therefore the mobility of this cluster rapidly decreases. This entanglement of the growing MM 104 cluster into the silicone matrix 101 plays out via mechanical constraints and frustration, instead of forming chemical bonds. Nevertheless, it immobilizes the MMs 104 just as effectively. This process of FIGS. 5B-C can be therefore characterized as chain polymerization, leading to entanglement.

The grafting and the entanglement processes of Eqs. (2)-(3) and FIGS. 5A-C both lead to the eventual loss of the mobility of the MMs 104, making them effectively immobile IMs 105. This immobilization induces the shape-change of the LAL 100, as described in relation to FIG. 1. The fast, UV-induced grafting, and the UV-induced start of the entanglement-by-chain polymerization are both mechanisms of the fast zone formation. The subsequent, slow but self-sustaining entanglement-by-chain polymerization even in the absence of (or in minimal presence of) UV illumination is a leading mechanism of the slow power drift. This power drift may be enhanced by low intensity UV component of the ambient light.

This document describes methods, techniques and chemical designs that control and reduce these unintended polymerization processes that drive grafting and entanglement, primarily in order to reduce the undesirable long-time slow optical power drift, but possibly also to reduce the short-time zone formation.

First, we review the processes that terminate these undesirable polymerization mechanisms. Then, we describe embodiments that utilize and control these termination processes to suppress and minimize power drift in LAL 100*s*. A first process that terminates chain polymerization occurs when two radicals X* 103* that are at the ends of their respective MMs 104 or IMs 105, get into each other's physical proximity and deactivate each other, thus terminating each other's growth, symbolically:

$$X^* + X^* = XX \qquad (4s)$$

In the more detailed notation:

$$MM{-}X^* + MM{-}X^* = MM{-}X{-}X{-}MM. \qquad (4s')$$

Several other processes that limit or impact the rate of the unintended polymerization are related to oxygen that is unavoidably present in the aqueous environment of the implanted LAL 100. In the aqueous of the eye the O2 concentration is around 0.5 ppm, substantially lower than 6 ppm, typical for water exposed to atmospheric conditions. The O2 concentration ([O2] for short) inside the LAL 100 equilibrates with the O2 in its surrounding aqueous environment. Remarkably, because the oxygen solubility in the LAL 100 is about eight times greater than in water, the [O2] inside the LAL 100 that is in equilibrium with the 0.5 ppm of the aqueous is about eight times higher, about 4 ppm, as further described below. This oxygen concentration [O2] is maintained by the homeostasis of the human body: if a chemical reaction starts to consume the oxygen in the LAL 100, the surrounding aqueous will tend to restore this concentration rather quickly. As described next, even at these low concentrations, oxygen plays an important role in the chemistry of the LAL 100. Therefore, controlling the oxygen content of the LAL 100 can be used to suppress the power drift.

In a particularly relevant example, the activated photoinitiators PI* 106* can react with the oxygen instead of activating mobile macromers MM 104. This reaction creates a lower activity PI derivative PI-OO, symbolically shown as:

$$PI^* + O2 = PI{-}OO \qquad (5s)$$

An example of this symbolic reaction (5*s*) is shown expressly as:

(5)

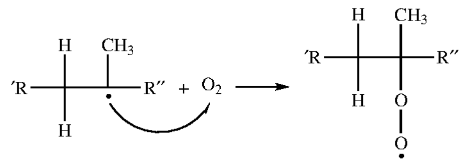

where, following convention, the remaining portions of the PI molecule are shown with R' and R". Another example is the above-mentioned benzoin PI 106, where the reaction of the activated PI* 106* radical with oxygen eventually creates benzoic acid:

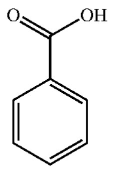

The reactivities of these low activity PI derivatives, such as the oxidized PI-OO, are much smaller than that of the activated PI* 106*, and therefore PI-OO is not labeled with a "*" Visibly, activated photoinitiators PI*s 106* reacting with oxygen depletes the concentration of PI* 106*, and thus beneficially reduces the unintended polymerization. For completeness, it is noted that the low activity PI-OO may still induce a PI-OO+MM=IM−X* reaction, but the reaction rate is much slower than the rates of reactions that involve a PI* 106*. In informal terms, the low activity PI derivative PI-OO (and its variants like PI-OH) will be referred to as "zombie photoinitiators".

Because of the process (5), the presence of oxygen is detrimental for the adjustment process, as it reduces the concentration of the photoinitiators that were intended to induce the LAL adjustment. But for stabilizing the LAL 100 against long time power drift, especially after the lock-in, the presence of oxygen is very helpful, since it deactivates the potential source of the unintended polymerization, including power drift. Remarkably, the reaction rate of process (2), the PI*+MM=IM–X* reaction is $k1=10^2$-$10^4$ L/mol*sec, whereas the reaction rate of process (5), the PI*+O2=PI-OO reaction is about $k2=10^6$-$10^8$ L/mol*sec. The ratio of these two reaction rates is estimated to be in the $k1/k2=10^{-2}$-$10^{-4}$ range, in some embodiments of the order of $10^{-3}$. These rates of course depend on various factors, such as temperature and concentrations. Thus, as long as oxygen is present in the LAL 100, most of the radicals PI* 106* will react with the oxygen, not with the mobile macromers MM 104. As such, judiciously including oxygen in the LAL 100 in a suitable concentration is an efficient way of controlling the polymerization because it greatly reduces, or even stops, the unintended photo-polymerization that would lead to zone formation or power drift. Below it will be described that simply increasing the [O2] at fabrication is not expected to bring benefits as the [O2] is expected to return to the equilibrium with the corresponding [O2] of the aqueous. Therefore, embodiments emphasize physical-chemical designs to enhance the oxygen content of the LAL 100. An example is to modify the earlier-mentioned oxygen solubility in the LAL 100.

Figure 6A:
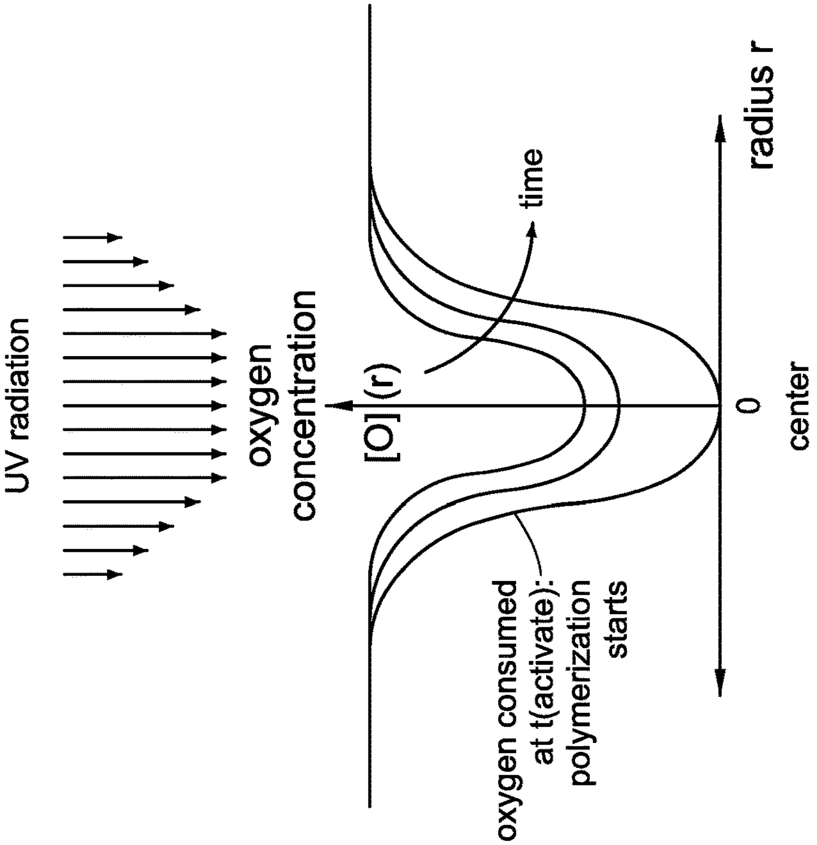
FIGS. 6A-B illustrate the dynamics of oxygen concentration and power change during UV illumination.
Figure 6B:
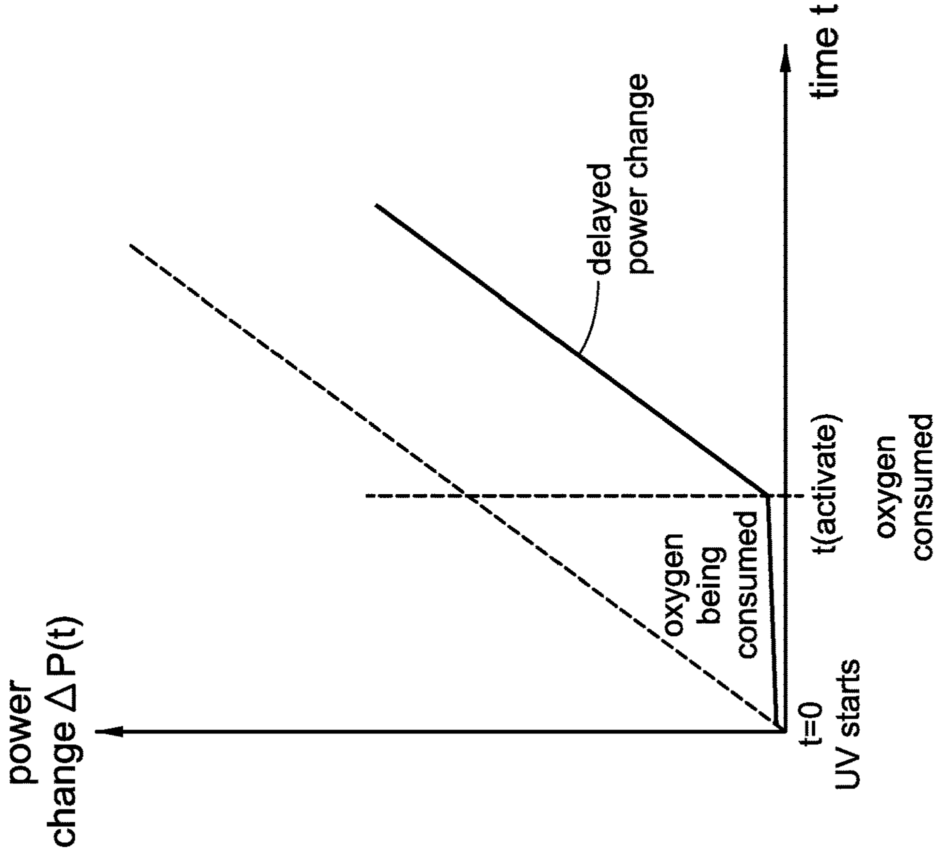

FIGS. 6A-B show that one of the consequences of the above processes is that when an adjustment, or a lock-in process, or even an unintended zone formation starts, there is an initial time period, when the UV radiation is already incident on the LAL 100, but only minimal, or no power change occurs. This is because most photoinitiator molecules PI 106, even though activated by the UV photons, are all subsequently consumed by the oxygen present in the LAL 100 through the fast and dominant step (5): the PI*+O2=PI-OO process. FIG. 6A illustrates the time evolution of the spatial profile of the radius-dependent oxygen concentration [O2](r) in this initial period as oxygen gets consumed and depleted when the LAL 100 is exposed to UV illumination. As long as there is a finite concentration of oxygen [O2](r) in the illuminated region, the rate of polymerization of the MMs 104 remains minimal. Once the oxygen is completely consumed and depleted by process (5) at t (activate), as shown by the outermost [O2](r) concentration profile, the polymerization and concomitant power change starts. FIG. 6B qualitatively illustrates that this dynamics delays the power change ΔP(t) of the LAL 100. FIG. 6B shows that during a light adjustment procedure the slope of the power change curve ΔP(t) is initially low, because the oxygen suppresses photo-induced polymerization, even as it gets consumed by process (5). Once essentially all oxygen is consumed by the time t (activate), photo-polymerization is not suppressed anymore by the oxygen, and thus the slope of the power change curve ΔP(t) substantially increases. In embodiments, the chemical compositions, concentrations and reaction rates of the silicone network 101, the mobile macromer MM 104, the switchable and non-switchable ultraviolet absorber and the photoinitiator PI 106 are such that during a light adjustment procedure this slope of the time dependent power adjustment curve can increase by a factor of two or more after a t (activate) time, when the oxygen has been nearly completely consumed in the illuminated region. Herein t (activate) can be in a range of 3 seconds-100 seconds in some embodiments; in others in the range of 5 seconds-50 seconds. In cases where the slope of the ΔP(t) curve varies noticeably, the slope averaged over a time period of 5-10 seconds after t (activate) can be at least a factor of 2 greater than the slope averaged over the time period 0–t (activate). In some cases, this ratio of slopes can be greater than 1.5. Referring back to FIG. 6A, in some embodiments, the oxygen concentration [O2] in a center of the LAL 100 decreases during the t (activate) time by more than 50%. In some other LALs 100, the oxygen concentration in the center of the LAL 100 decreases during the t (activate) time by more than 90%.

In dynamical terms, the above-described reactions involving the PI can be represented by the following rate equation:

$$d[PI^*]/dt = +\alpha I(UV)[PI] - k1[MM][PI^*] - k2[O2][PI^*]. \qquad (6)$$

Here I(UV) represents the intensity of the incoming UV illumination, a is an efficiency constant, [PI*], [PI], and [MM] represent the concentration of the compounds PI*, PI, and MM; and k1 and k2 are reaction rates for processes (2) and (5), introduced earlier. As stated above, in characteristic embodiments k1<<k2, while [O2]~4 ppm and [MM]=10-50 wt %, in some embodiments 20-30 wt %. The ratio of the full rates (including the concentrations) of the two processes that consume PI*s is denoted by R=k2 [O2]/k1 [MM]. This can be also thought of as a ratio of a PI quench rate Rq=kq[X*][O2] to an add rate Ra=ka* [X*][MM], from which R=Rq/Ra=kq [O2])/ka [MM], as before, identifying kq=k2 and ka=k1.

Embodiments can reduce the undesired power drift by having a high R ratio, which represents that most activated PI*s 106* get quenched by oxygen instead of activating MMs 104 into radicals MM-X* 104*. In some embodiments, R can be in the range of 1-1,000, in some embodiments in the range of 1-100, in others in the range of 1-10. In such LALs 100 where R>>1, the majority of the PI* radicals 106* get neutralized/consumed by oxygen, thereby reducing the unwanted polymerization of the mobile macromers MMs 104. In contrast, in LALs 100 where R is closer to 1, or even less than 1, a majority of the PI* radicals 106* actively promotes polymerization of mobile macromers MM 104 that induces uncontrolled polymerization and power drift. Therefore, fabricating LALs 100 with an R ratio much larger than 1 is another efficient method of polymerization control and power drift prevention.

Another important oxygen-related reaction that can reduce chain polymerization is that the radicals X* that drive the chain polymerization also react with the oxygen instead of the other mobile macromers MM 104. This reaction converts the high activity radicals X* into low activity XOO* compounds, symbolically:

$$X^* + O2 = XOO^*. \qquad (7s)$$

Or, in the more detailed notation:

$$MM{-}X^* + O2 = MM{-}XOO^*. \qquad (7s')$$

The low activity radical XOO* is often a peroxy (or peroxyl) radical. Since the XOO* compound is much less reactive than the radical X*, this process largely deactivates the radical X*. While the ability of these low activity XOO* compounds to start subsequent chain polymerization is suppressed, it is still non-zero, as described later.

With these preparations (5)-(7), the rate equation for the oxygen concentration can be written as follows:

$$d[O2]/dt=\beta([Oeq]-[O2])-k2[O2][PI^*]-k3[O2][X^*]. \quad (8)$$

This process spatially evolves via diffusion. Thus, if the spatial dependence is explicitly represented, then:

$$\partial[O2]/\partial t=D\partial^2[O2]/\partial r^2-k2[O2][PI*]-k3[X^*], \quad (9)$$

which equation needs to be solved with the appropriate boundary conditions that, among others, fix [O2] at [Oeq] at the boundary of the LAL 100, the equilibrium oxygen concentration of the LAL 100, equilibrated with the aqueous of the eye. β is a constant representing the rate of the oxygen equilibrating process, and k3 is the reaction rate for process (7). There are corresponding rate equations for [X*], [MM] and the concentration of immobilized macromers [IM], which will not be described in detail.

Figure 7:
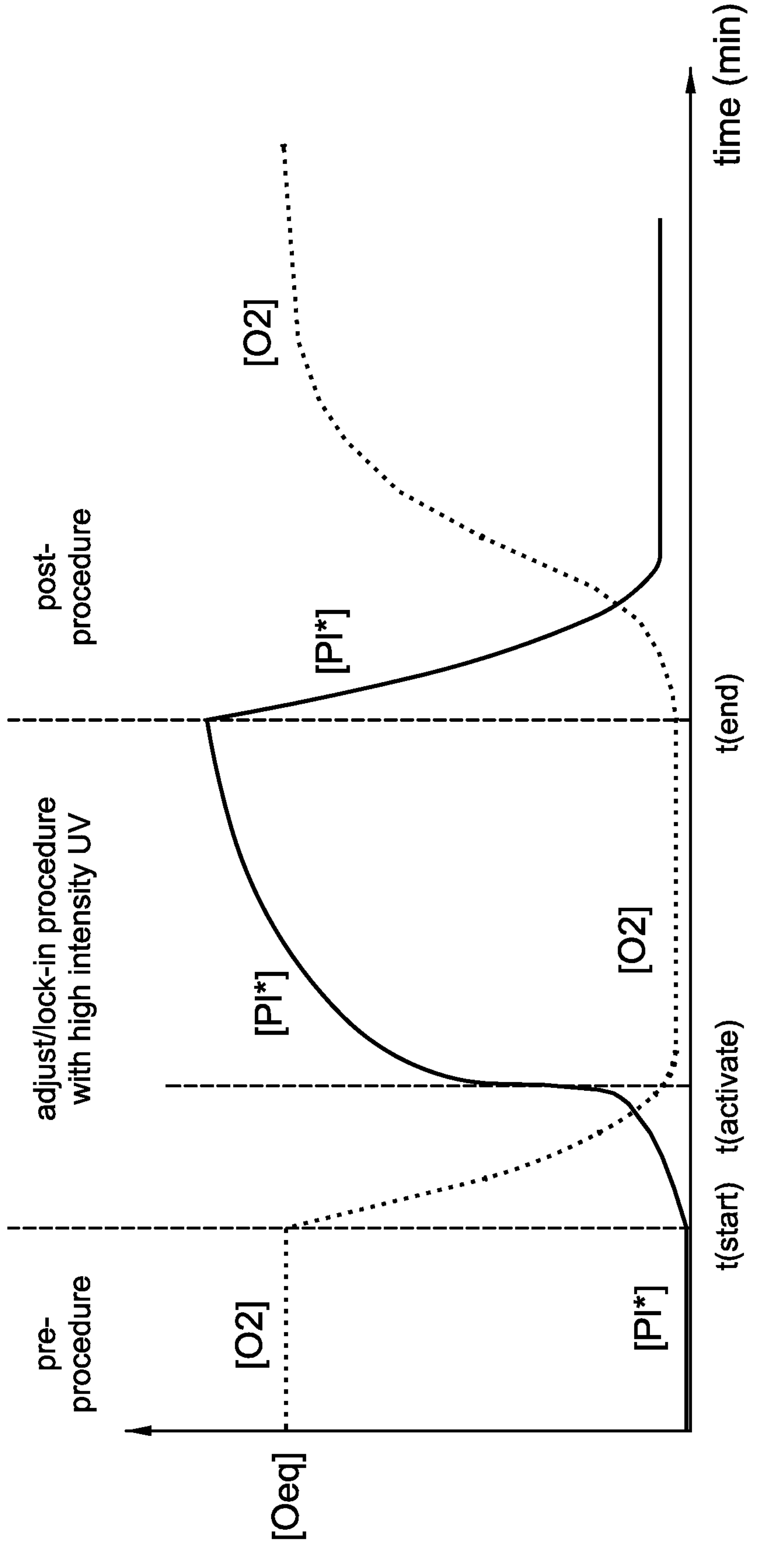
FIG. 7 illustrates the concentration of oxygen [O2], and photoinitiator radicals [PI*] during and after UV illuminating procedures, including adjustment, lock-in and possibly zone formation.

Next, the dynamics of [O2], guided by equations (5)-(9), which are coupled to the analogous equations for [X*] and [MM], will be described, before, during and after an adjustment or lock-in procedure. FIG. 7 shows the concentration [PI*] of the activated photoinitiator radical PI* 106*, and the concentration of oxygen [O2] in the LAL 100. The adjustment, or lock-in, procedure starts at t (start) by applying a UV illumination beam and ends at t (end) by switching off the UV beam. Before the UV beam is applied, oxygen is present in a concentration [Oeq], equilibrated with the aqueous of the eye. Also, in the absence of an incident UV beam, there are no activated PI* radicals present before t (start), and hence [PI*] is negligibly small. Once the UV beam is applied at t (start), PI* 106* radicals are created by the UV photons via process (1), or step (1). The fastest process involving activated PI* radicals 106* is process (5), the consumption of PI*s by oxygen. Therefore, most UV-activated PI* 106*s get quickly consumed by process (5). Accordingly, after the UV beam is switched on at t (start), the [O2] rapidly decreases from [Oeq] while the [PI-OO] concentration (not shown) grows correspondingly, and the negligible [PI*] remains minimal, as shown. During this process, the decrease of [O2] suppresses the ratio R from its high initial value. This makes the PI* radicals 106* consumed less and less by reacting with oxygen and more and more by polymerizing mobile macromers MM 104.

Once the oxygen concentration [O2] reaches approximately zero at t (activate), the PI* radicals 106* stop being rapidly consumed by oxygen, and thus from t (activate), the UV illumination starts to increase the [PI*] rapidly, as shown. After t (activate), the PI* 106* radicals primarily induce the polymerization and immobilization of the mobile macromers MM 104, which induces the adjustment of the optical power of the LAL 100. The [PI*] flattens out at a dynamical equilibrium value determined by the balance of the generation of PI* 106*s** by the UV beam and the consumption of the PI* 106*s by the polymerization of the MM 104***s*. In formal terms, by setting the right hand side of Eq. (6) to 0.

Finally, when the UV beam is switched off at t (end), the PI* 106* radical concentration [PI*] starts to decrease according to Eq. (6), and the oxygen concentration climbs back to its equilibrium value [Oeq], according to Eqs. (8)-(9). A typical duration of such an adjustment or lock-in procedure, |t (end)-t (start)|, is 20-200 seconds; in some embodiments 30-100 seconds. The graph of FIG. 7 reviews the central role of oxygen in influencing the PI* 106*concentration [PI*] in every stage of the UV illumination process. This review provides a useful context for analyzing and controlling the power drift, induced by the reactions of MM 104, PI* 106* and oxygen, primarily over a long time after t (end).

While nominally FIG. 7 illustrated the light adjustment process by intentionally applying a UV beam, it is informative for the unintended UV-induced zone formation process, and for the UV-induced fraction of the power drift process. Zone formation involves a UV illumination with an intensity lower than used in the adjustment or lock-in procedures, such as an inadvertent exposure to sunlight by a patient not wearing the required sunglasses before lock-in. If the inadvertent exposure lasts long enough, the O concentration can decrease to a sufficiently low level that PI* generation starts to speed up (as it happens after t (activate) in FIGS. 6-7), and induces the polymerization of MMs 104 that changes the shape of the LAL 100 in the illuminated zone. As mentioned before, LALs 100 with the front protection layer 110 minimize and typically eliminate the chances of such zone formation.

Figure 8:
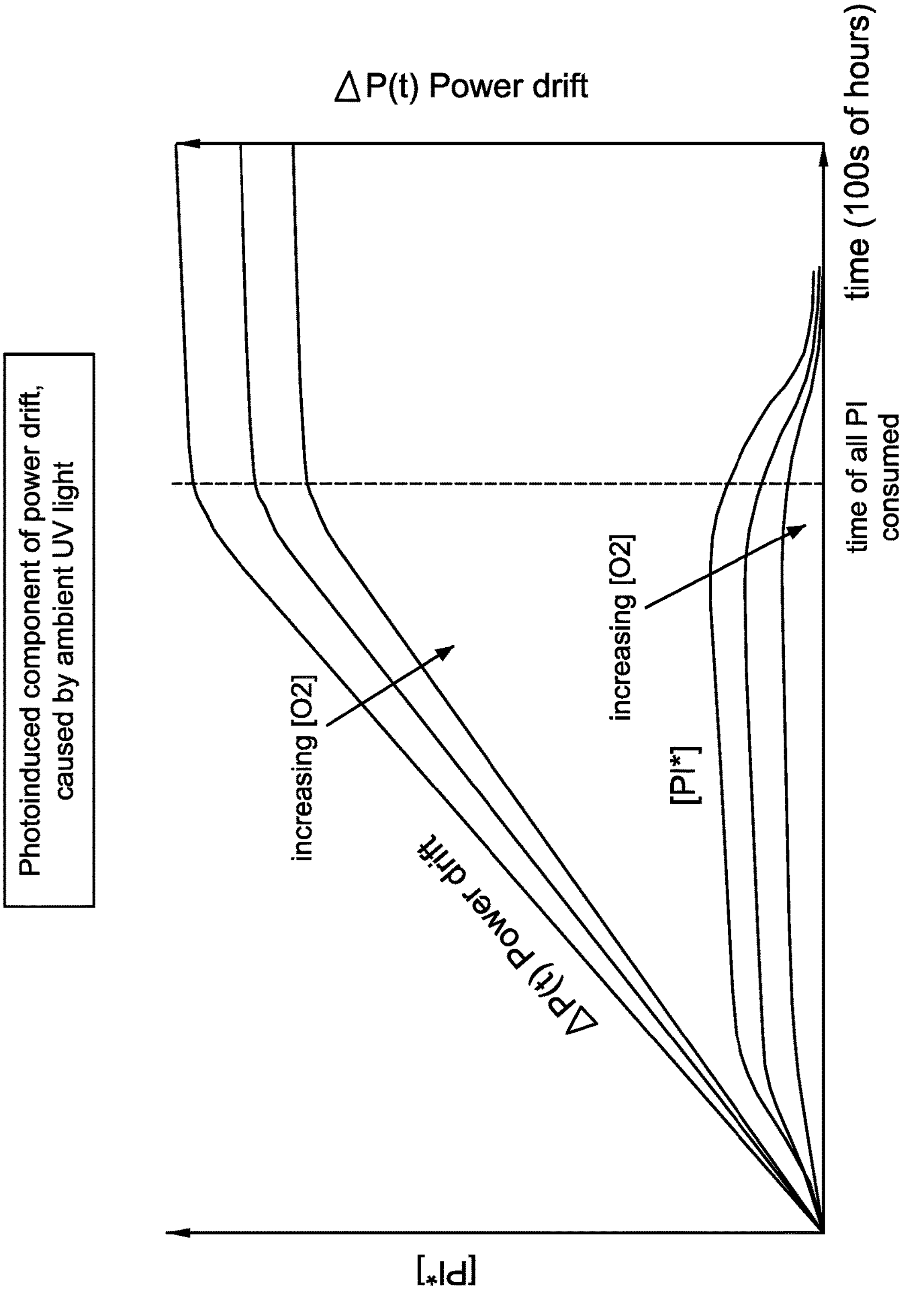
FIG. 8 illustrates the concentrations of oxygen and of the photoinitiator radicals [PI*] during and after unintentional UV exposure.

FIG. 8 illustrates that in weak ambient UV illumination the UV-activated processes (1) and (5) reach a dynamic equilibrium with a very small, but non-zero PI* radical concentration [PI*]. This [PI*] concentration is very small because the UV light is insufficient to reduce to zero, and thus most activated PI* 106* reacts with oxygen and turn into the zombie-photoinitiator PI-OO. Still, this very low but non-zero [PI*] can induce undesired polymerization and thus an increasing power drift ΔP(t) over hundreds of hours, as shown. From this description it is clear that LALs 100 that have a chemical composition that accommodates more oxygen will have a lower equilibrium [PI*], and therefore a slower UV-induced power drift.

The above description was directed to the UV-induced component of the power drift. Typically, the greater fraction of the power drift is caused by chain-polymerization, which may be started by UV absorption, but continues spontaneously in a self-sustaining manner even without UV illumination. Having described the role of oxygen in controlling and managing the UV-induced polymerization, the description now turns to its role in controlling chain-polymerization. Oxygen limits and suppresses this polymerization process as well by the process (7) that turns the radical, or activated endgroup, X* 103* into the much less reactive XOO* group, such as peroxy. Therefore, an efficient control design to suppress unintended polymerization in a LAL 100 is to incorporate oxygen into the LAL 100 which reacts with the X* radicals 103* (of the activated mobile macromers MM-X* 104*) via process (7) and turns them into the weakly active radicals XOO*, or MM-XOO*.

Figure 9B:
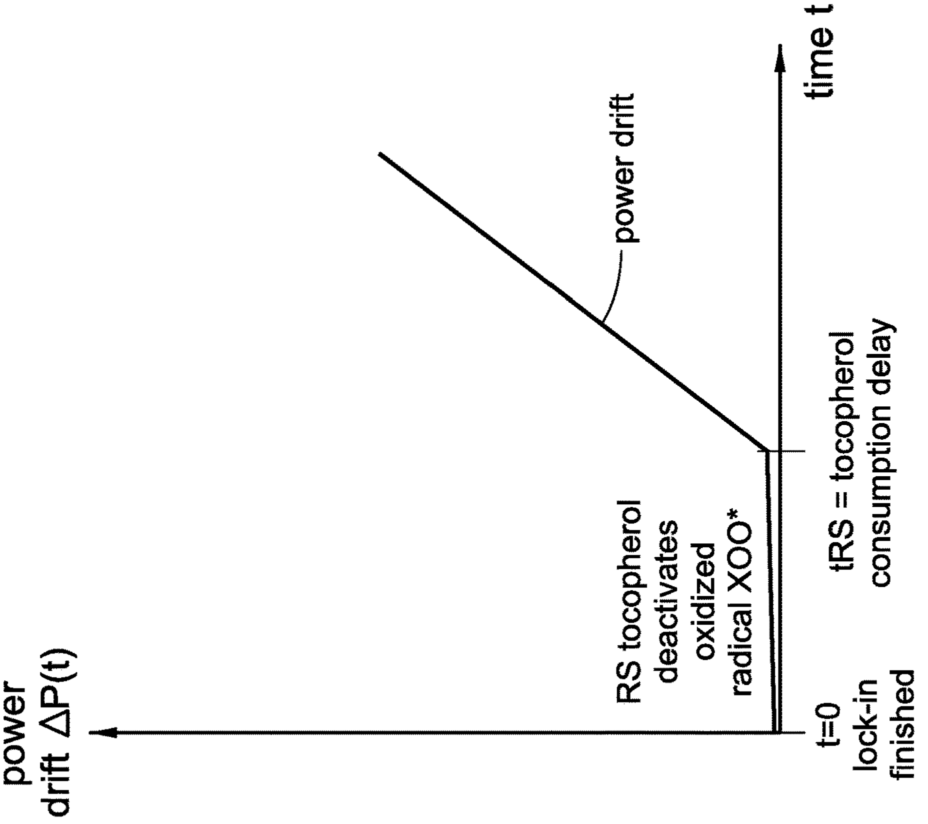
FIGS. 9A-B illustrate the reaction dynamics of radical scavengers RS 125.
Figure 9A:
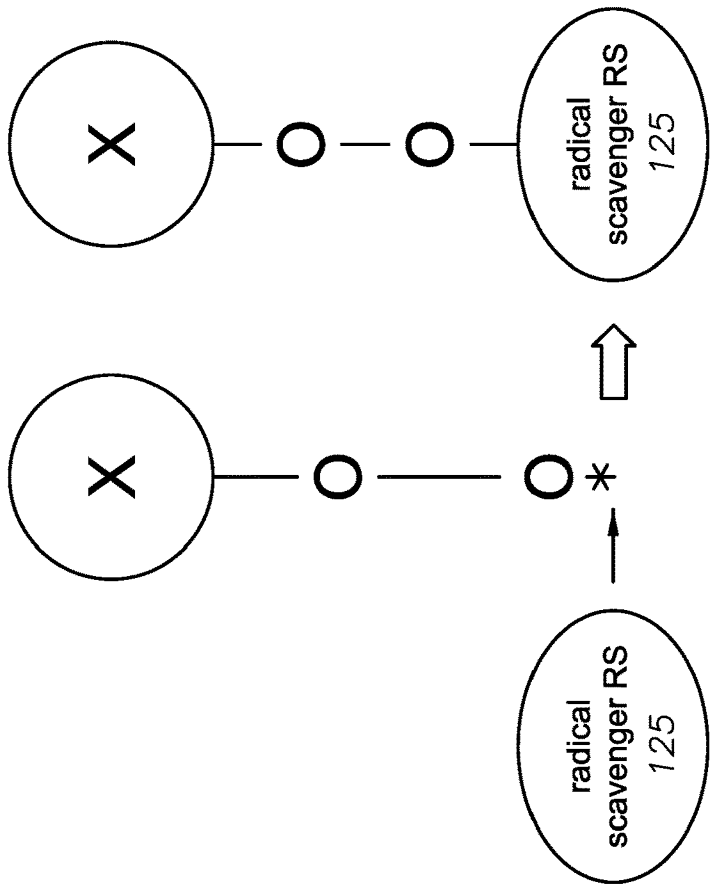

However, the reactivity of this low activity radical XOO* is still not zero, and so it can still drive a slower power drift over hundreds of hours. FIGS. 9A-B show that therefore, some embodiments of the LAL 100 control and reduce this unintended polymerization by including radical scavengers RS 125 to further deactivate these oxidized, low activity radicals XOO*, symbolically expressed as:

$$RS+XOO^*=XOOd \quad (10s)$$

Here XOOd denotes the deactivated XOO* group, having reacted with the radical scavenger RS 125. In the more detailed notation:

$$RS+MM-XOO^*=MM-XOOd \quad (10s')$$

A potent example of such a radical scavenger RS 125 is tocopherol, or vitamin E, with the formula:

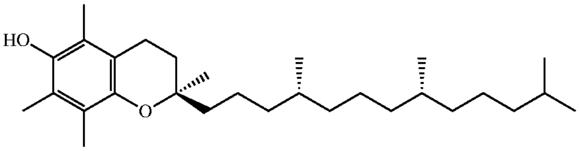 [SMILES: Cc1c(C)c2c(c(C)c1O)CC[C@@](C)(CCC[C@H](C)CCC[C@H](C)CCCC(C)C)O2]

The radical scavenger RS 125 can be tocopherol in its different, α, β, γ and δ forms. The O* of XOO* reacts with the OH at the end group of the tocopherol, and this electron exchange neutralizes the O* radical center, thereby turning XOO* into an inactive group. Other radical scavengers include ascorbates, butylated hydroxytoluene (BHT), butylated hydroxyanisole (BHA), or 2,6-di-tert-butyl-4-methoxyphenol. In general, many varieties of radical scavengers are known. A shared property of many of them is that they are proton-donors, which have a preference for reacting with peroxy radicals.

Figure 10A:
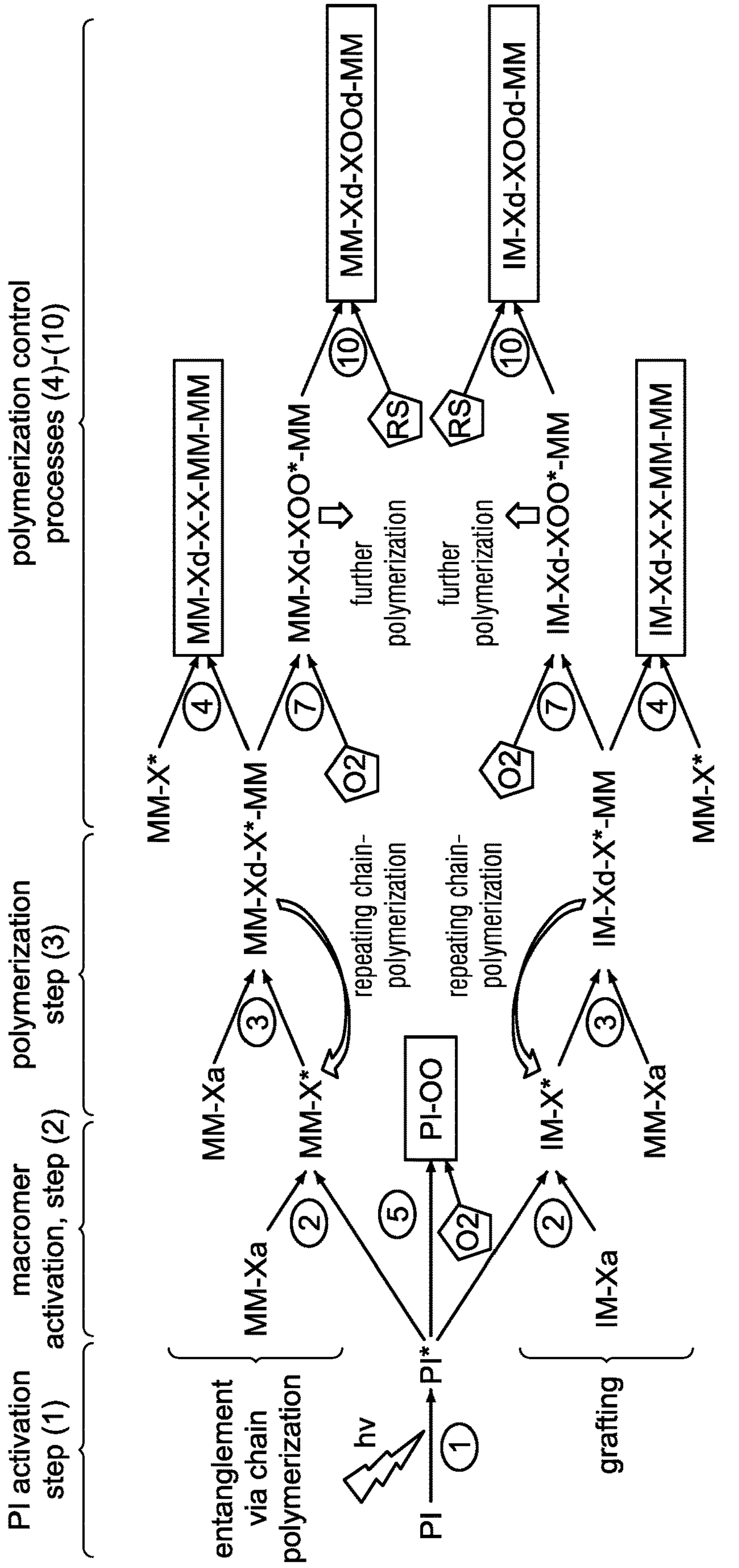
FIGS. 10A-B summarize the steps of the polymerization, and the polymerization control design processes.
Figure 10B:
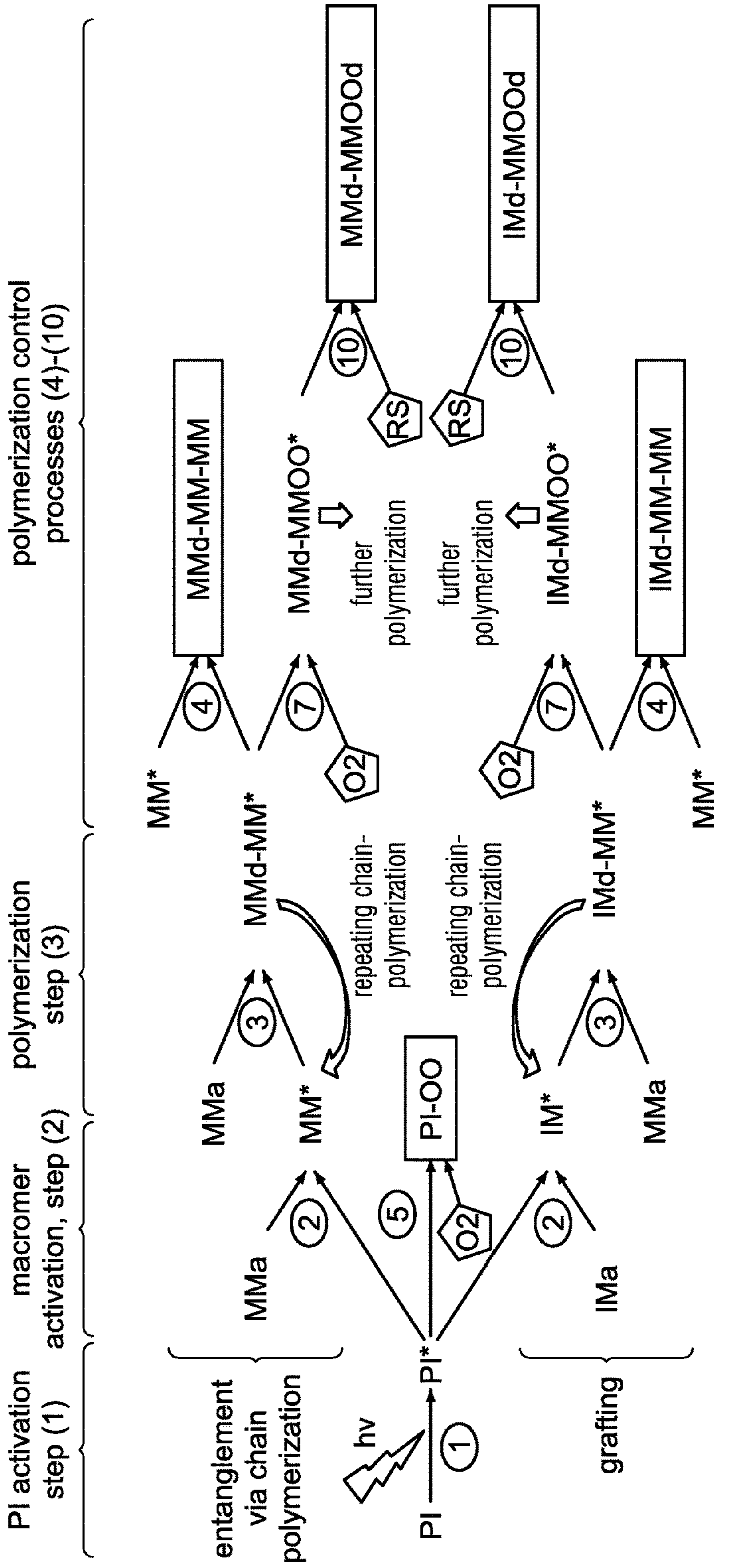

The above-described photoactivated polymerization steps (1)-(3) and polymerization control design processes (4)-(10) are comprehensively summarized in FIGS. 10A-B. The numbers in the circles indicate the label of the steps or processes. The boxes around the chemical formulas (e.g. PI-OO, and MM-Xd-XOOd-MM) indicate that the polymerization control designs managed to deactivate these compounds from participating in further polymerization. The pentagons around O2 and the Radical Scavenger RS 125 indicate that these are important agents for polymerization control designs. FIGS. 10A-B show both the immobilization via entanglement by chain-polymerization process and the immobilization via grafting reaction pathways. FIG. 10A uses the detailed chemical notation that explicitly shows the endgroup X 103 of the MM 104 and IM 105 in its three states: Xa for an activatable X. X* for an activated X, and Xd for a deactivated X, while FIG. 10B uses the most compact notation, where MMa stands for a Mobile Macromer with an activatable endgroup Xa 103*a*, MM* stands for a Mobile Macromer with an activated endgroup X* 103*, and MMd stands for a Mobile Macromer with a deactivated end group Xd 103*d*. These two notations are provided as alternative, analogous description of the same chemical pathways.

Returning to polymerization control process (10), some LALs 100 make use of the control design of introducing radical scavengers RSs 125 into the LALs 100 that react with the low activity radicals XOO* and further deactivate them into approximately inactive groups XOOd via process (10). Advantageously, the reaction rate k (RS-XOO*) of tocopherol with the low activity XOO*/peroxy radicals is fast, while its reaction rate k (RS-PI*) with the activated PI*s 106* is slow. Therefore, tocopherol does not substantially slow down the adjustment and lock-in processes that rely on the PI* 106* radicals, while it quite efficiently completes the suppression of the unintended chain-polymerization via process (10) that was already substantially suppressed by oxygen via process (7). In particular, FIG. 9A shows how the radical scavenger RS 125 deactivates the still moderately active radical center of the low activity radical XOO*, and FIG. 9B shows that after the lock-in is finished, as long as both oxygen and RS 125 tocopherol are present, the polymerization, and the corresponding power shift ΔP(t) is suppressed until all the RS 125 tocopherol is consumed.

In ordinary circumstances, the UV component of the ambient light experienced by a patient from sunlight or indoor lighting, reduces the LAL 100's PI concentration [PI] to zero over a range of times, e.g. between 100 and 1,000 hours by activating the PIs 106 into PI* 106*, which then get consumed either by oxygen or by the polymerization process. In some typical cases, this time can be in the range of 300-500 hours. This time can be referenced as the drift-active time. During this drift-active time essentially all PI 106 gets consumed by the UV component of the ambient light. Accordingly, the polymerization control designs and processes to protect against the PI-driven power drift need to be effective only over this drift-active time of hundreds of hours, not for the decades of the lifetime of the LAL 100. Accordingly, polymerization control designs and processes that are capable of effectively suppressing the major mechanisms of the power drift of the LAL 100 include following. (1) Fabricating LALs 100 that accommodate enough oxygen to deactivate the photoinitiators PIs 106 and to lower the activity of the radicals X* 103* of the mobile macromers 104 and immobilized macromers 105 by transforming them into low activity radicals XOO*. Since [O2] in the LAL 100 equilibrates with the aqueous, indirect methods are needed for this. (2) Fabricating LALs 100 that contain enough radical scavengers RSs 125 to extensively deactivate the low activity radicals XOO* over the drift-active time. Details of these classes of polymerization control designs and processes are further detailed next.

Figure 11A:
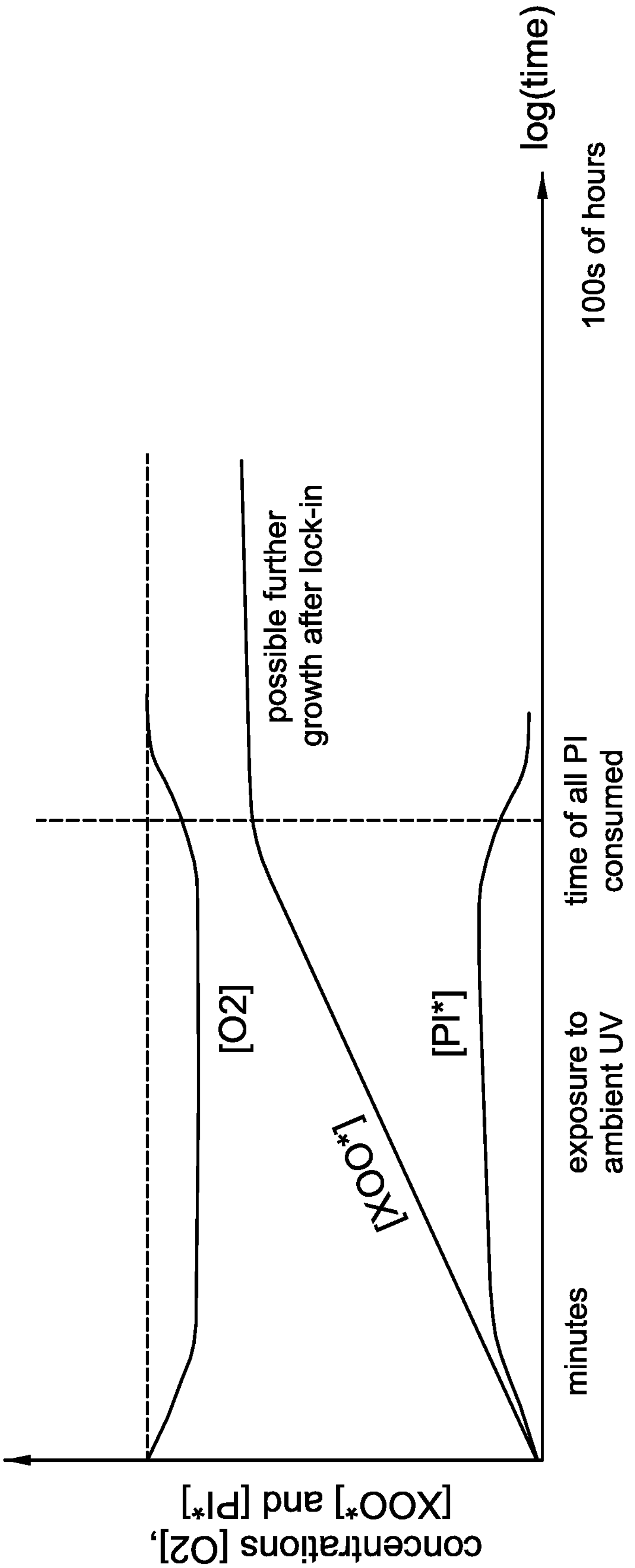
FIGS. 11A-B illustrate the concentration of oxygen [O2], and XOO* radicals [XOO*] in the absence and in the presence of radical scavengers RS.
Figure 11B:
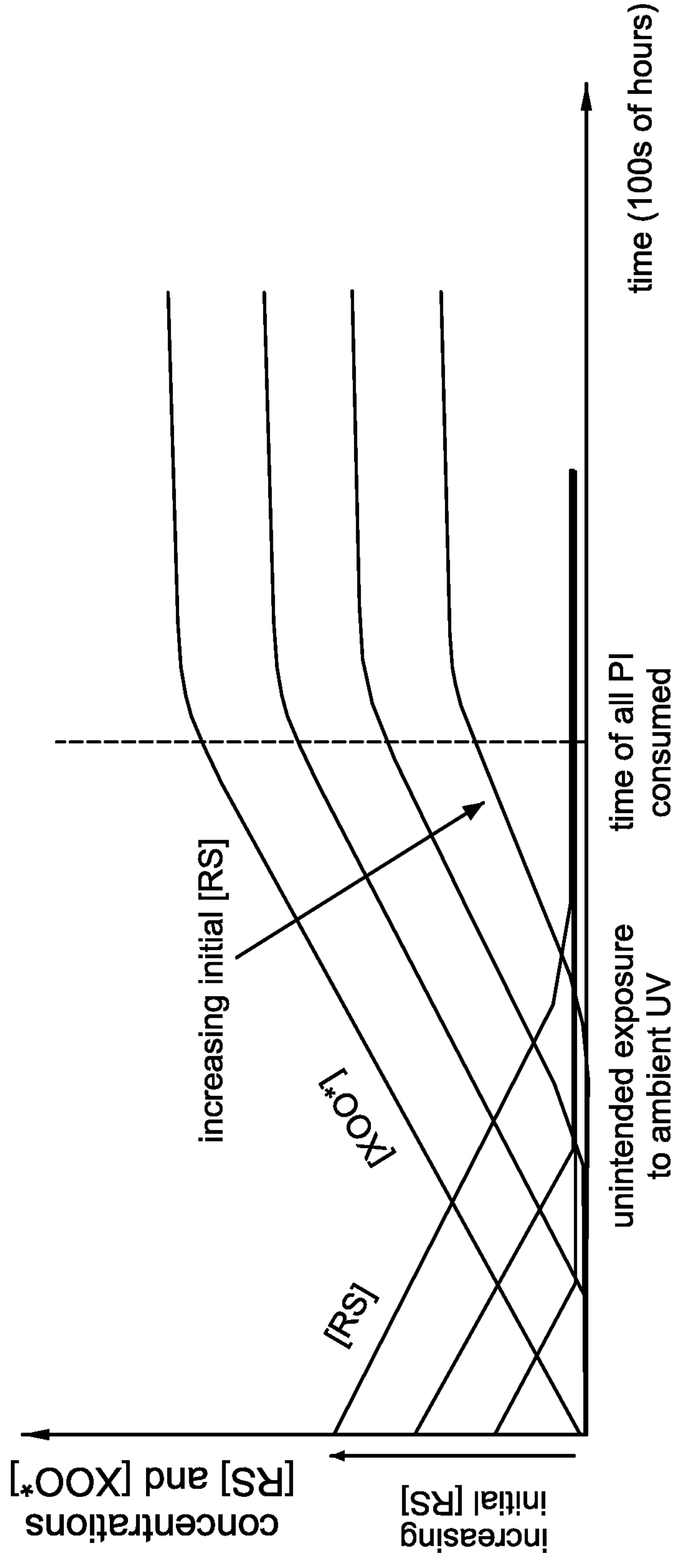

FIGS. 11A-B show the effect of the radical scavengers RS 125 on the power drift dynamics of FIG. 8 in some detail. FIG. 11A shows that without the radical scavenger RS 125, when an LAL 100 is exposed to some low intensity/ambient UV irradiation, the UV photons start activating PI* 106* radicals by process (1)/step (1). The process of PI* 106* generation is limited by process (5), in which the oxygen turns the PI* 106* radicals to much less reactive PI-OO zombie photoinitiators. These competing processes (1) and (5) set a dynamically balanced [PI*] that depends on the [O2] as shown. Process (5) also consumes oxygen and therefore tends to reduce [O2], while equilibration to [Oeq] by the aqueous via process (8) tends to increase [O2]. These two competing processes set a dynamically balanced concentration, as shown. And since [O2] converges to a stationary value, the concentration [PI*] also converges to a stationary value, as shown. These stationary concentrations [O2] and [PI*] remain until all PI 106 are consumed, at which time [PI*] returns to its initial near-zero value, and [O2] also returns to its initial value, equilibrated to the aqueous. These photoactivated PI* 106*s induce a slow power drift of the LAL 100, as described in FIG. 8, while the oxygen-generated PI-OO zombie photoinitiators have minimal residual reactivity, and thus do not add to the power drift.

FIG. 11A-B illustrate that in conjunction with the above, oxygen transforms a portion of the activated endgroups X* 103* into low activity XOO* radicals by process (7). The generated XOO* radicals induce further polymerization and thus are additional drivers of the power shift ΔP(t). FIG. 11A shows that the concentration of these XOO* radicals grows over time as long as the PI* 106* radicals are getting generated by ambient UV illumination.

XOO* radicals can be additionally generated by chain-polymerization that does not involve UV-generated PI* radicals 106*, followed by the oxygen-driven process (7). This process can continue even after lock-in, as the lock-in dominantly polymerizes MM 104*s* in the central region, and thus there can be residual MM 104*s* in the periphery of the LAL 100 that were not reached by the lock-in beam with full intensity, which then can very slowly drift into the central region of the LAL 100 and continue the chain-polymerization and XOO* generation. Therefore, over hundreds of hours, the low activity radical concentration [XOO*] can still grow and induce a slow power drift of the LAL 100 in a small percent of procedures, possibly even after lock-in, as shown in FIG. 11A.

FIG. 11B illustrates that some polymerization control methods suppress even this residual power drift by taking advantage of process (10), in which a radical scavenger RS 125 deactivates the low-reactivity XOO* groups. As shown, process (10) suppresses the generation of the XOO* groups until all RS 125 are consumed and [RS] hits zero. As the polymerization control designs add RS 125 in increasing amounts, the rise of the [XOO*] concentration is delayed, and its dynamical equilibrium value, in an approximate sense its plateau value, gets reduced. In some cases, even the growth rate of the [XOO*] (its slope) get reduced by the introduction of RS 125. Naturally, over time the reduction and control of the [XOO*] concentration also consumes the radical scavenger RS 125, thus its concentration [RS] decreases with time, as shown.

Next, various processes that involve UV absorbers will be discussed. FIGS. 2A-B showed that recent upgrades of the LAL 100 introduced the additional front protection layer 110. FIG. 2A is a top view of the LAL 100. FIG. 2B is a side view of the LAL 100 that shows the front protection layer 110, and an optional, often useful back protection layer 120. The front protection layer 110 typically includes a switchable UV absorber that can switch between a strongly UV-absorbing configuration and a weakly UV-absorbing configuration.

An embodiment of the switchable UV absorber is azobenzene, known to change its absorption properties upon stimulation by light. Azobenzene is one of the simplest examples of the family called azo compounds by the general form of R—N═N—R', where R and R' can be an aryl or an alkyl, or groups of these. Azobenzene is known to have two conformations, differing in the bond angle between the N═N double bond and one of the two phenyl rings. The "trans" conformation has high absorption in the UV spectrum, with a peak in the 360-370 nm wavelength range, where the absorption involves a π-to-π* electronic transition. An analogous absorption peak is present in a variety of functionalized azobenzenes as well. A UV light with a wavelength around 365 nm can serve as the high-to-low modulating stimulus 310-*htl*, to transform the azobenzene from its high-absorption isomer 300-*h* with trans conformation to its low-absorption isomer 300-1 that has a cis conformation. As shown, the cis conformation has a much lower absorption around 365 nm wavelength. Therefore, azobenzene is an embodiment of the switchable UV absorber of the front protection layer 110 that largely blocks incoming UV rays in its trans conformation, but can be switched into the low absorption cis conformation to let the adjusting radiation through to the LAL 100. For completeness, it is mentioned that azobenzene-based compounds can have additional conformations.

There are many other embodiments of the switchable UV absorber beyond azobenzene. The switchable UV absorber can be an azo-aromatic compound, a diazene, an azo-pyrazole, a dienylethene, a fulgicide, an azulene, a spiropyran, an ethene-aromatic compound, a macromer of one of these compounds, a polymer of these compounds, a composition containing one of these compounds, a composition containing one of these compounds as side-chains, a composition containing one of these compounds as a backbone having a side-chain, a nanoparticulate bonded to one of these compounds; and one of these compounds dissolved in an ionic fluid. The switchable UV absorber could also be a polymer incorporating any of the just listed compounds into the polymer host polymer network itself, so it doesn't have to be incorporated as a side chain. Some such compounds may include a polymer which bends in response to light. The description continues by overviewing an extensive list of embodiments of the switchable UV absorber.

As mentioned earlier, the azo-aromatic compound can be, e.g., azobenzene that exhibits the following conformational change:

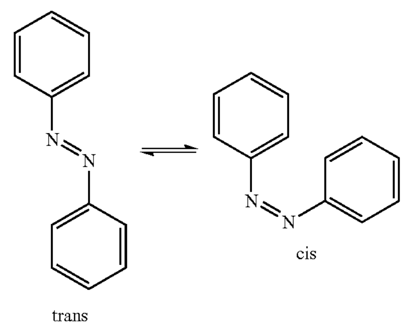 [SMILES: c1ccc(/N=N/c2ccccc2)cc1 ; c1ccc(/N=N\c2ccccc2)cc1]

In other embodiments of the switchable UV absorber, the azo-aromatic compound can be 4-methoxy azobenzene:

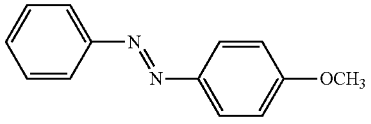 [SMILES: COc1ccc(/N=N/c2ccccc2)cc1]

The switchable UV absorber can also be an indazole, allylated azobenzene with various spacer links, or another version of phenyl azopyrazoles, as shown:

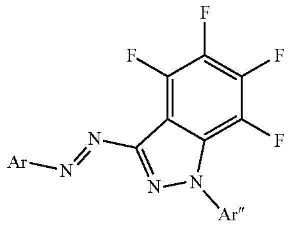

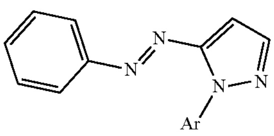

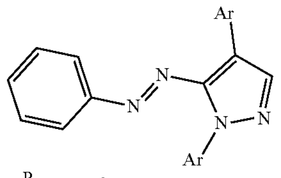

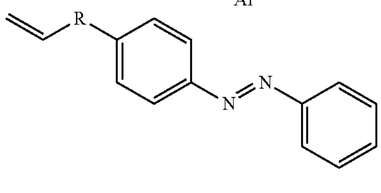

In yet other embodiments, the azo-pyrazole can be a vinyl phenyl azo-pyrazole VPAP:

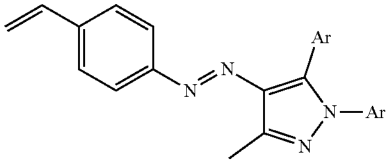

Finally, in some embodiments, the ethene-aromatic compound can be stilbene:

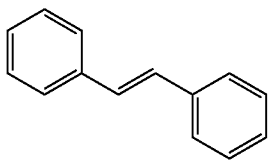 [SMILES: C(=C\c1ccccc1)/c1ccccc1]

Embodiments of such switchable absorbers have been described in great detail in commonly owned U.S. patent application Ser. No. 16/658,142, entitled: "Light Adjustable Intraocular Lens with a modulable absorption front protection layer", by I. Goldshleger et al., the entire content of which is hereby incorporated by reference. Under illumination by ambient light, these switchable absorbers very efficiently absorb UV light. However, when illuminated by a high dose of UV light, an internal dynamic balance between the two (trans and cis) conformations of the VPAP molecule shifts and the front protection layer 110 becomes partially transparent to UV. This change opens the door for the adjustment UV beam to enter the bulk of the lens and initiate the above-described adjustment effects. Once the adjusting irradiation is completed and the UV beam is switched off, this front protection layer 110 switches back to strongly UV absorptive. By this absorption-switching mechanism, this VPAP front protection layer 110 protects the LAL 100 from unintended adjustments by the fraction of the mobile macromers that are still active, from implantation to lock-in.

The switching between the strongly UV absorbing and the weakly UV absorbing configurations may degrade the UV absorber's structure in a small percent of these switching events. Moreover, these back-and-forth switching events are ongoing as the system maintains its stationary state. Therefore, switching UV absorbers can be assigned a half-life t (sUV) that represent after how many switching events will the structure of 50% of the switchable UV absorbers degrade and lose their ability to switch. This half-life t (sUV) is based on the number of switching events the switchable UV absorber can survive times the characteristic time between switches. This switching time depends on the temperature and on the chemical parameters. LALs 100 with switchable UV absorbers whose structure degrades faster lose their UV protection from the front protection layer 110 faster. Since the lock-in typically takes place 15-30 days after the implantation and the UV exposure is typically impactful less than 10 hours a day, embodiments of the switchable UV absorbers that have a half-life t (sUV) in an implanted environment that exceed 200 hours can be advantageous. Some embodiments of the switchable UV absorber can have a half-life t (sUV) that even exceeds 400 hours in an implanted environment.

The same degradation process can be also captured via the number of switching events. Depending on their specific chemical composition, the switching UV absorber molecules start to show an increasing degree of degradation after a number of switching events that can be in the 50,000-500,000 range, in some cases, in the 100,000-200,000 range.

The switching UV absorbers can also degrade because the activated PI* 106* or the XOO* molecules migrate into the front protection layer 110. Further, after the PI 106 is consumed in the front central region, PI 106 can migrate to this front central region from the periphery or any other regions of the lens.

Next, several polymerization control designs will be described that control and suppress unwanted and uncontrolled polymerization and thus reduce the unwanted power drift of the LAL 100. Embodiments of the LAL 100 can combine more than one of the listed polymerization control designs for amplified benefits and advantages.

(1) One of the broad polymerization control design principles is to create LALs 100 that are capable of accommodating oxygen in as high concentration as possible. Some LALs 100 can be capable of accommodating an oxygen concentration in the range of 0.5-50 ppm. Other LALs 100 can accommodate oxygen concentrations in the 0.5-20 ppm range, in the 4-20 ppm range, or in the 6-20 ppm range. The initial oxygen concentration of the LAL 100 is expected to equilibrate with the 0.5 ppm oxygen concentration of the aqueous of the eye after implantation. Therefore, LALs 100 need to have chemical and physical properties that enable them to retain a higher oxygen concentration even after equilibration with the aqueous. One design principle is, as established earlier, that LALs 100 with higher R=k2 [O2]/k1 [MM] ratios can retain excess oxygen and thus suppress unwanted power drift more efficiently. In the earlier equivalent notation, R can be also expressed as the oxygen concentration [O2] times an oxygen-driven photoinitiator quench rate kq (above denoted as k1) over a mobile macromer concentration [MM] times a photoinitiator-driven polymerization add rate ka (above denoted as k2): R=kq [O2]/ka [MM].

In some embodiments, R can be greater than 10, 100, or 1,000. In the silicone-based compound of the LAL 100 that equilibrated with the aqueous with a partial oxygen pressure, the oxygen concentration is given by the product of the pressure and the oxygen solubility. The solubility, in turn, is given by the oxygen permeability divided by the diffusivity. Since the oxygen concentration of the eye's aqueous cannot be comfortably modified, polymerization control designs are directed to advantageously adjusting the solubility or the diffusivity of the LALs.

In typical silicones, the oxygen permeability due to diffusion is 500-800 "barrers", a non-SI unit. In SI units, the permeability is given in units of mol/(m*sec*Pa), and 1 barrer=3.35*10-16 mol/(m*sec*Pa). In existing embodiments of the LAL 100, the permeability of oxygen is a lesser 100-200 barrers. Therefore, the chemical design of the LALs 100 can be improved by increasing their oxygen permeability and thus solubility, while possibly reducing the oxygen diffusivity towards the levels of regular silicone exhibit. LALs 100 with such chemical designs will have enhanced oxygen concentration [O2], and therefore reduced power drift. Accordingly, some LALs 100 can have a chemical composition such that a permeability, a solubility, and a diffusivity of oxygen enable an oxygen concentration in the 4-20 ppm range, in some cases in the 6-20 ppm range.

Another way to capture these polymerization designs uses the equilibrium equation:

$$[O2]_{LAL} = (S_{LAL}/S_{aq})[O2]_{aq}, \tag{11}$$

where $[O2]_{LAL}$ and $[O2]_{aq}$ are the oxygen concentrations in the LAL and in the aqueous, while $S_{LAL}$ and $S_{aq}$ are the solubilities in the LAL and in the aqueous. In some characteristic silicones, like PDMS, the ratio $S_{LAL}/S_{aq}$ is about 8. This makes it possible that even though $[O2]_{aq}$ in the aqueous is only about 0.5 ppm, in the LAL an $[O2]_{LAL}$ of about 4 ppm can be reached. Some polymerization control designs further increase this $[O2]_{LAL}$ by at least one of the polymer silicone network 101 and the mobile macromer MM 104 include at least one of fluorine, and a functional group containing fluorine. Accordingly, in some LALs 100 the ratio $S_{LAL}/S_{aq}$ can be greater than 5, in some embodiments, greater than 10.

(2) In some LALs 100 the R ratio can be increased not only by boosting the oxygen concentration [O2], but also by reducing the k1 (or kq) reaction rate in the denominator that characterizes the polymerization process. The endgroup of the methacrylates of the mobile macromer MM can be described by the formula:

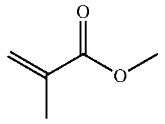

In some LALs 100 the CH3 side group of the penultimate carbon atom can be replaced by a longer group or chain. In other LALs 100, one or both hydrogens can be replaced by a CH3 or a longer side chain. More generally, an endgroup 103 of the mobile macromer MM 104 can include sidechains longer than CH3 methyl. Such MMs 104 have a slower polymerization add rate k1 (or ka) and thus a favorably higher R ratio.

(3) Some LALs 100 can include a radical scavenger RS, or an antioxidant to suppress unwanted polymerization. In some LALs 100, the RS concentration [RS] can be in the 5-1,000 ppm range, in some embodiments in the 10-500 ppm range, in yet other embodiments in the 50-200 ppm range. A class of antioxidant radical scavengers is tocopherol, or vitamin E. Remarkably, LALs 100 with elevated and [RS] concentrations were found to exhibit 50% lower power drift. Such 50% reduction can be achieved, e.g., in LALs 100 with [O2] in the 5-10 ppm range, and tocopherol concentration in the 100-200 ppm range.

Figure 12:
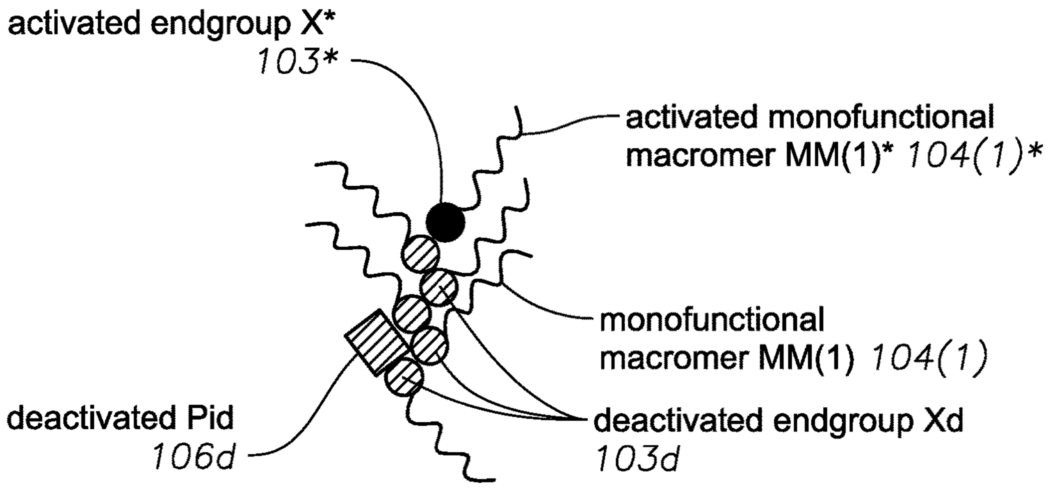
FIG. 12 illustrates polymerization with monofunctional macromers MM(1).

(4) FIG. 12 illustrates that in some embodiments, the power drift can be suppressed by a different polymer control design. In some embodiments of the LAL 100 the underlying silicon polymer network may be infused with mobile macromers MM that can be activated only on one of their ends. In some embodiments, only one of the endgroups of the mobile macromer MM 104(1) is an acrylate. Such macromers can be referred to as monofunctional macromers MM(1) 104(1), to distinguish them from the above described bifunctional macromers that form multi-branched chain polymerization, as shown in FIG. 5C. As shown in FIG. 12, when an activated photoinitiator PI* activates such a monofunctional mobile macromer MM(1) 104(1), a chain polymerization can start subsequently, but the chain-polymerized clusters will have a linear backbone, or zig-zag spine, but no secondary and additional branches. Therefore, the chain polymerization after the UV illumination stops will be suppressed and limited, thereby reducing the probability and degree of unintended power drift. It is worth mentioning that LALs 100 with such monofunctional mobile macromers MM(1) 104 (1), while they have less or even negligible unintended power drift, may also limit the adjusting UV illumination to induce less (intended) power change. The power change achievable by UV illumination can be about 2.0-2.5 D in LALs with bifunctional MM 104*s*, while only 0.4-0.7 D in LALs with monofunctional MM (1) 104(1) s.

(5) Yet other embodiments of the LAL 100 employ polymerization control designs and suppress the undesirable power drift by incorporating sterically hindered mobile macromers MM (sh) 104 (*sh*). The chemically activatable bond in a generic acrylate endgroup Xa 103*a* of the MM 104 (*sh*) is the double bond between the ultimate and penultimate carbon atoms:

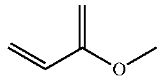

Sterically hindered endgroups 103 (*sh*) comprise additional ligands around this C=C double bond to spatially hinder the access of the radical center of the photoactivated photoinitiators PI* 106*. For example, in a methacrylate endgroup 103 the H on the penultimate C is replaced with a CH3. Other sterically hindered MM 104 (*sh*) replace the two hydrogens at the ultimate C with other carbon atoms, each possibly forming CH3, or longer chains. Yet other sterically hindered MM 104 (*sh*) replace the three hydrogens of the CH3 group of the penultimate C of the methacrylate end group 103 with carbon atoms, each possibly forming CH3, or longer chains. In other sterically hindered MM 104 (*sh*), a carbon atom of the activatable double bond of an endgroup 103 (*sh*) of the mobile macromer MM 104 (*sh*) also forms a bond with a CH3 methyl group, or a longer chain. In other sterically hindered MM 104 (*sh*), a carbon atom of the activatable double bond of the endgroup 103 (*sh*) of the mobile macromer MM 104 (*sh*) also forms a bond with a carbon atom that is coupled with at least one more carbon atom. In yet other sterically hindered MM 104 (*sh*), the ultimate or penultimate carbon atom of the activatable double bond of an acrylate endgroup 103 (*sh*) of the mobile macromer MM 104 (*sh*) also forms a bond with a CH3 methyl group, or a longer chain.

Yet others make the chain connecting to the end group 103 longer e.g. by using propyl, iso-propyl, tert-butyl, sec-butyl, butyl acrylates, cyclohexyl, cyclopentyl and phenyl acrylate. Each of these sterically hindered structures tend to reduce the rate of the subsequent chain polymerization process, and thereby the rate of the unwanted power drift.

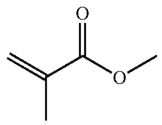

(6) In some LAL 100 embodiments, the power drift can be reduced by re-engineering the underlying Si polymer network 101. It is recalled that the mobile macromers MM preferentially bond to the polymer network 101 at its vertices, which were created by crosslinkers XLK 102. Therefore, polymer silicone networks 101 with less crosslinkers XLK 102 offer less attachment vertex-points where the mobile macromers MM could bond to the underlying silicone network. Forming silicone networks 101 with fewer crosslinkers 102 suppresses one of the two main processes that immobilize macromers, shown in FIG. 5A. Therefore, LALs 100 with such reduced-crosslinker density exhibit reduced power drift. It is mentioned that fewer crosslinkers tend to make the LA 100 softer. Also, other polymer control designs reduce the incorporation of the MM 104 into the Si network 101 during the curing of the LAL 100.

(7) In yet other embodiments, the power drift is reduced by a different design of the front protection layer 110. The front protection layer 110 has been described as comprising a switchable UV absorber, or UV blocker. However, as described earlier, some switchable UV blockers degrade with time, induced by the radicals in the system such as the PI* 106* or the XOO* radicals. The degradation of the switchable UV absorber over time results in an increasing fraction of the incident UV photons getting past this front protection layer 110, acting as another driver of unintended power drift.

In order to reduce this increasing amount of UV getting past the front protection layer 110, some embodiments of the front protection layer 110 can be formed with a combination of a switchable and a non-switchable UV blocker. In such LAL 100*s*, any potential degradation of the switchable UV blocker leads only to a partial loss of UV blocking, as the permanent UV blockers do not degrade and do not lose their ability to block the UV light over time. In some LALs 100, the non-switchable UV absorber is a 5-50% fraction of the combined amount of the switchable and non-switchable UV absorbers in the front protection layer 110. In some other embodiments this fraction is in the 10-40% range, in yet others in the 20-30% range.

Figure 13:
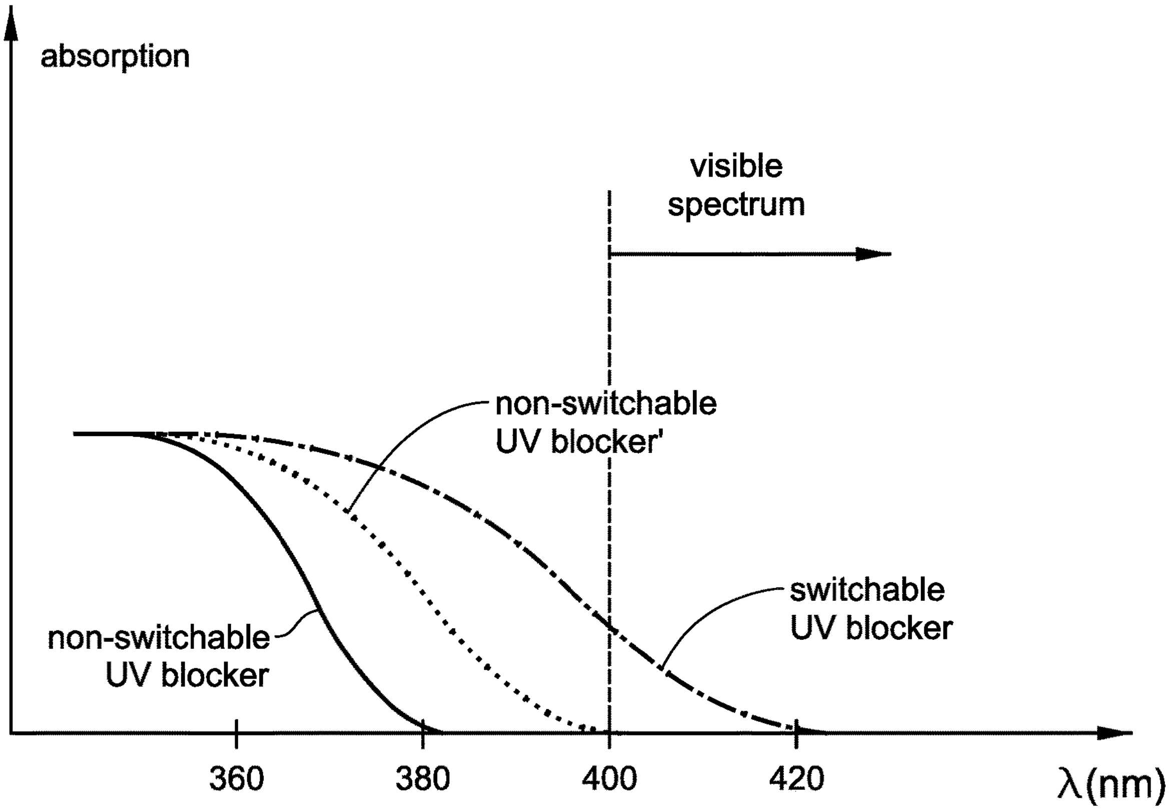
FIG. 13 illustrates the absorption properties of switchable and non-switchable UV absorbers.

When selecting the non-switchable UV absorber, several additional issues can be considered. One of these is that some switchable UV absorbers, like VPAP, turn the visual experience more yellow than patients are comfortable with, since the absorption spectrum of VPAP has a tail into the visible spectrum above 400 nm, as shown in FIG. 13. Therefore, the added non-switchable UV blocker can be preferably selected based on its property of providing strong UV blocking for wavelengths less than 400 nm, but minimal blocking above 400 nm, as shown in FIG. 13. In other words, in some LALs 100 the non-switchable UV absorber absorbs efficiently for wavelengths shorter than 400 nm. Since these wavelength considerations do not impact the control of the polymerization processes and do not contribute to the suppression of the unwanted power drift, they are not an integral or necessary part of the polymerization control designs. Rather, they are meant to improve the overall visual experience for the patients. Examples include UV absorbers which absorb efficiently at wavelengths shorter than 380 nm, or 390 nm. A wide variety of suitable non-switchable UV absorbers, or UV blockers, have been described in U.S. Pat. No. 6,851,804, entitled: "Readjustable optical elements" by J. M. Jethmalani et al., and U.S. Pat. No. 9,119,710, entitled: "Adjustable optical elements with enhanced ultraviolet protection", by R. H. Grubbs et al, both patents hereby incorporated in their entirety by reference.

(8) As mentioned above, in LALs 100 the switchable UV absorber in the front protection layer 110 may degrade over time in part because of reacting with radicals, primarily the PI* 106* radicals, or the XOO* radicals that diffuse into the front protection layer 110 from the bulk of the LAL 100, or get created by UV radiation after a not-yet-activated PI 106*a* diffused into the front protection layer 110 previously. To suppress this degradation mechanism, some LALs 100 suppress the diffusion of PI 106 into the front protection layer 110. The hydrophobic PI photoinitiators 106 diffuse efficiently into the hydrophobic silicon matrix 101 of the bulk and the front protection layer 110. The water content of the hydrophobic bulk and the front protection layer is typically 4% or less. In contrast, some LALs 100 adopt the polymerization control design by adding water into their front protection layer 110, thereby repelling the diffusion of the hydrophobic PI 106 into their front protection layer 110. Some LALs 100 have a water content of their front protection layer in the 4%-20% range, some LALs in the 5%-10% range. Other control designs modify the hydrophobicity of the silicone polymer network 101, yet others that of the mobile macromers 104, in order to change the hydrophobicity of the front protection layer 110, and suppressing the PI in-diffusion this way. Each of these polymer control designs reduces the degradation of the switchable UV absorbers, and thus eventually the unwanted power drift of the LAL 100. Some control designs may introduce an additional insulating layer between the bulk of the LAL 110 and the front protection layer 110 to suppress the in-migration of the radicals PI* 106* and XOO*.

(9) In some LAL 100 embodiments, the photoinitiator PI itself may be switchable between a protected state and an activatable state. In some sense, the protected state can be referred to as a "caged" state. In some embodiments, the UV-sensitive bond that is activatable by the incoming UV photons may be protected by its molecular surroundings. For such switchable PIs to become functional, first the protected state needs to be switched or modified, so that a subsequent UV photon can break the UV-sensitive bond itself. The protected state may be switched by a light of a first wavelength, different from the UV light of a second wavelength used in the shaped illumination that activates the photoinitiator PI 106 to adjust and to lock-in the LAL 100. For example, a shorter wavelength UV light may be used to alter the protected state which was designed to absorb only such shorter wavelength irradiation. Since these switchable PIs 106 are "on-demand", they are inactive in the absence of the activating UV light, and therefore do not induce any unwanted polymerization and power drift. Expressed another way, the photoinitator PI 106 is less photoactivatable in the protected state than in the activatable state. In some embodiments, the photoinitator is minimally photoactivatable in the protected state.

Such switchable PIs do not necessarily rely on multi-photon processes in the traditional sense. Multi-photon processes typically have low efficiency and thus require high beam intensities that may exceed retina-safe levels. In these processes a first photon often excites an electron to a first, intermediate state, and then a second photon excites the same electron to the higher-energy target state. In the present case, the excitation of this second electron would constitute the activation of the PI 106. Since in many muti-photon processes the first intermediate state has a very short lifetime, the second photon has to be incident very shortly after the first photon, often within picoseconds or nanoseconds. These short electronic lifetimes necessitate high intensity. In contrast, in embodiments of the switchable PI, the protective structure is a protective bond or configuration, whose switched state after the absorption of the first photon can have a long lifetime. Therefore, the second photon can arrive considerably later and still activate the UV-sensitive bond of the PI 106. As such, lower intensity beams may operate these switchable PI control designs successfully.

(10) In yet other embodiments, the photoinitiator PI 106 itself may be anchored to the network 101. In such systems, the anchored PI 106 can still activate the MM 104 mobile macromers. However, physically these anchored PIs 106 are mechanically and dynamically hindered from reaching the activatable endgroups 103 of the Mobile Macromers MMs 104 and Immobilized Macromers IMs 105. In particular, the shaped illumination activates the photoinitiator PI 106 by breaking it into two radicals PI* 106*, wherein at least one of the radicals remains attached to the polymer silicone network 101. Therefore, anchored PIs 106 are less effective inducing a chain polymerization process, and thus are much less likely to induce an unwanted power drift. Some LALs 100 with such anchored PIs 106 may exhibit history dependence, which needs to be addressed. In some control designs, illumination patterns can be developed that correspond to different illumination histories.

(11) In yet other LAL 100 embodiments, the power drift is prevented by not utilizing a photoinitiator PI 106 altogether. In such LALs 100 the polymerization of the MM mobile macromers 104 is induced directly by two-photon or multi-photon processes. Initiating such processes often requires a higher intensity illumination. Therefore, in such LALs 100 the UV illumination can be delivered by a laser, possibly in a scanning operation with a tight focus. If two photons of 500 nm wavelength from such a laser impact a Mobile Macromer MM 104 sufficiently quickly one after the other, they can induce a polymerizing chemical reaction of the type of process (1) and (2) directly in the MMs 104: this process would otherwise be induced by a single UV photon with a wavelength of 250 nm, to be corrected for losses. In contrast to the above-described processes, no equivalent of the PI* radical 106* is ever generated in such LALs, and therefore there is no corresponding induced power drift after the illumination stops.

LALs with a Caged Photoinitiator

Figure 14:
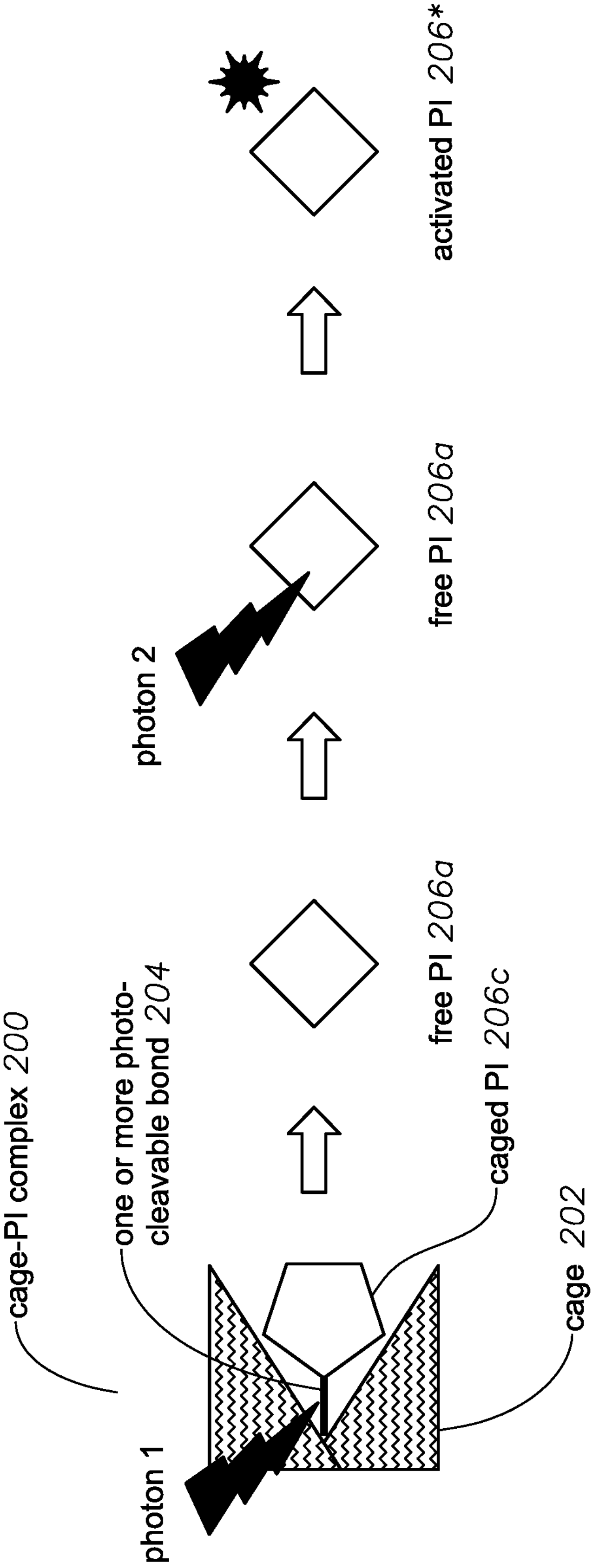
FIG. 14 shows the mechanism of action for the caged photoinitiator.
Figure 14:
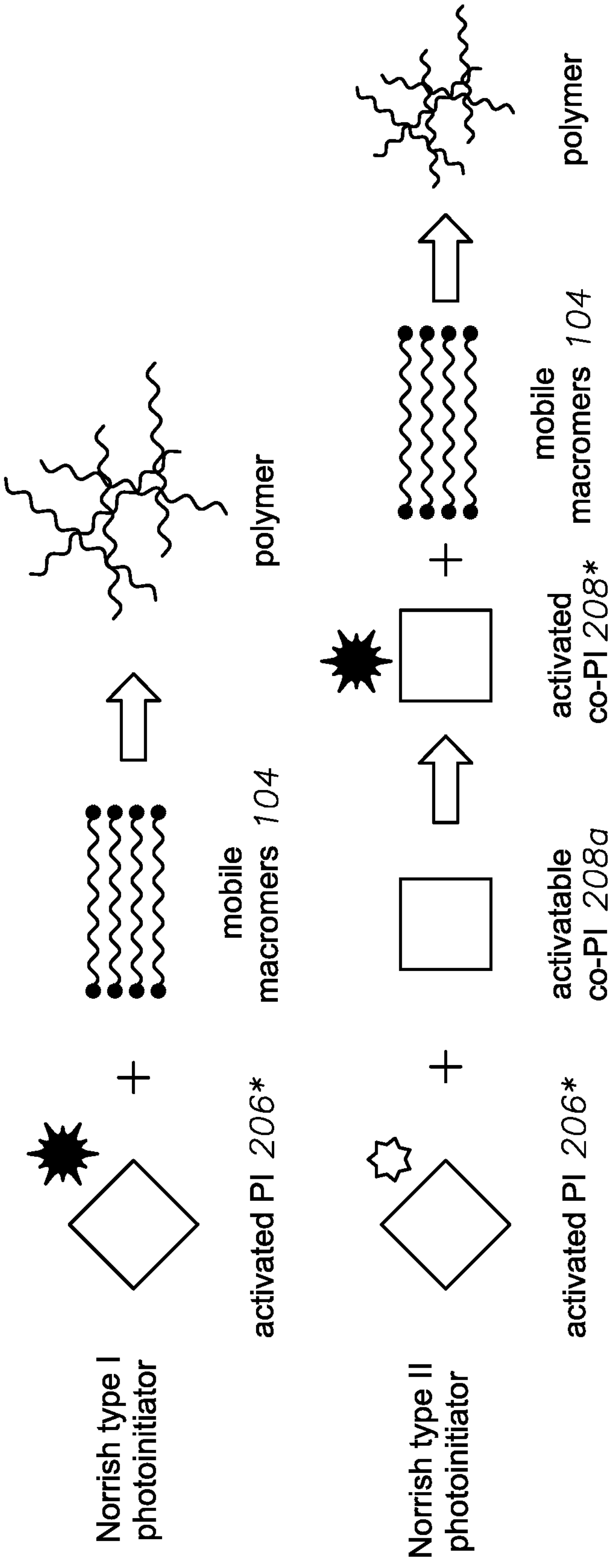

In this section, embodiments of the Light Adjustable Lens (LAL) 100 are described which include a caged photoinitiator **206*c* to manage the unwanted power drift of the LAL 100. FIG. 14 shows that, as before, such LAL 100 can include a polymer silicone network 101, molded in the presence of a mobile macromer 104 and a (non-switchable) ultraviolet absorber; and a cage-photoinitiator complex 200; wherein the caged photoinitiator 206*c* can be freed from the cage 202 by a first photon of a first illumination; the free photoinitiator 206*a* can be activated by a second photon of a second illumination; and the activated photoinitiator 206* is capable of inducing a polymerization reaction of the mobile macromer 104, leading to a changing of an optical power of the LAL 100. The cage-photoinitiator complex 200, or the caged photoinitiator 206*c* itself play the same function as the previously described broad class of photoinitiators 106, and thus can be viewed as embodiments of the latter. Also, we carry on with the notation that the photoinitiator (or PI) in its activatable, or pre-activated state is labeled 206*a*, in its activated state 206*, and in its deactivated state 206*d*. The 206*c* label is added to indicate that the PI is caged within the cage-PI complex 200 by at least a photocleavable bond 204. The caged PI 206*c* is indicated by a symbol differently shaped from the free PI 206*a*. As it will be shown below, this notation is used to indicate that the freeing of the PI from the cage often involves more than just photocleaving a bond. It often involves a rearrangement of atoms and bonds that involves both the caged PI 206*c* and the cage 202**.

A uniquely useful aspect of these embodiments of the LAL 100 is that the photoactivation of the caged PI **206*c* is a multi-photon process, and therefore LALs 100 with such a caged PI 206*c* have minimal sensitivity to an external UV illumination, at least at illumination intensities typical for ambient sunlight. With suitable choice of parameters, this sensitivity to ambient UV light can be minimized to such a degree that, after a patient-requested adjustment of the optical power of the LAL 100, the remaining caged PIs 206*c*** may not need to be deactivated by additional lock-in procedures. Moreover, if a patient does not even request a power adjustment, then no UV illumination procedure (adjustment or lock-in) would be necessary at all. The elimination of the need for a lock-in procedure may reduce the number of needed post-implantation visits. Reducing the number of visits and the number of UV illumination procedures has the potential to substantially increase the acceptance of the LAL technology by doctors and patients alike.

On a conceptual level, the efficiency of multiphoton procedures depends on the illumination intensity, or power, in a quadratic, or more broadly, a polynomial manner. This is to be contrasted with the efficiency of single-photon-activatable photoinitiators, where this relationship is linear. The polynomial dependence on the illumination intensity makes it possible to keep the photopolymerization efficiency high at the high intensities of the adjustment procedure such that the optical power of the LAL 100 can still be suitably adjusted, while markedly suppressing the photopolymerization efficiency at the low intensities of ambient sunlight to such a residual degree that the need for a lock-in procedure is eliminated. An additional dynamical process of the physical chemistry of the LALs 100 will be described below, which essentially eliminates even this residual UV sensitivity, and thus eliminates the need for lock-in by a wide and safe margin.

Before proceeding, it is recalled from FIG. 2 that embodiments of the LAL 100 can include the front protection layer 110 that can include a switchable ultraviolet absorber. Also, as shown in FIGS. 5A-C, the polymerization reaction can include grafting a mobile macromer 104 onto the polymer silicone network 101, or bonding to another mobile macromer 104, wherein the bonded macromers eventually entangle with the polymer silicone network, see FIG. 5B-C.

Returning to FIG. 14, during the first step of the photoinitiation process, the (caged) photoinitiator 206*c* is freed from the cage 202 into a free photoinitiator (PI) 206*a* by the first photon of the first illumination into a mobile state without activation. The fact that the free PI 206*a* is only activatable but not yet activated is indicated by the "a" label. The mobility of the PI 206*a* enhances the ability of the PI 206*a* to photoinitiate the polymerization reaction of the mobile macromers 104. In some embodiments, it is possible that the mobility of the PI 206*a* is low, or that the PI 206*a* is possibly even localized or anchored, as in the above section (10).

Figure 15A:
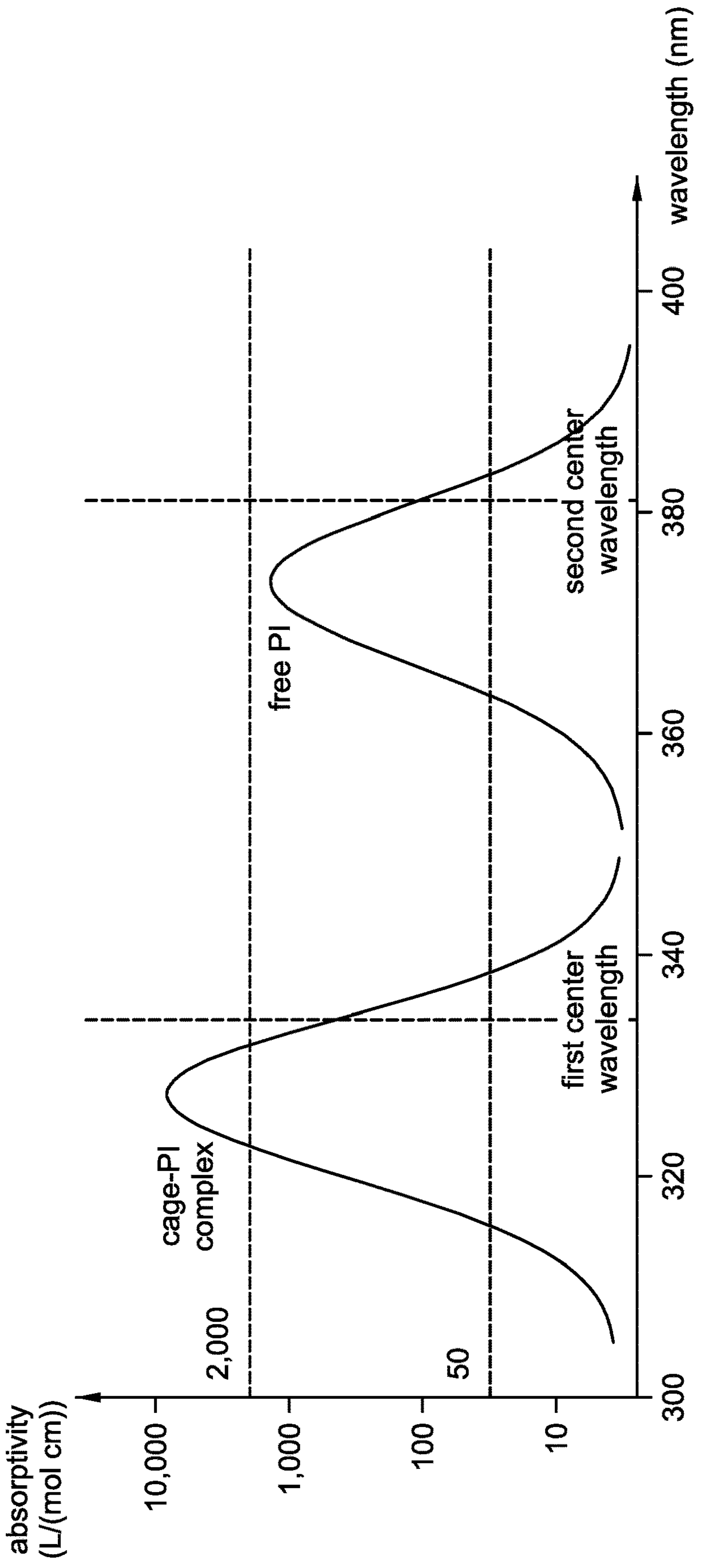
FIG. 15A-B shows the absorptivity of the cage-photoinitiator complex and the free photoinitiator in different embodiments.
Figure 15B:
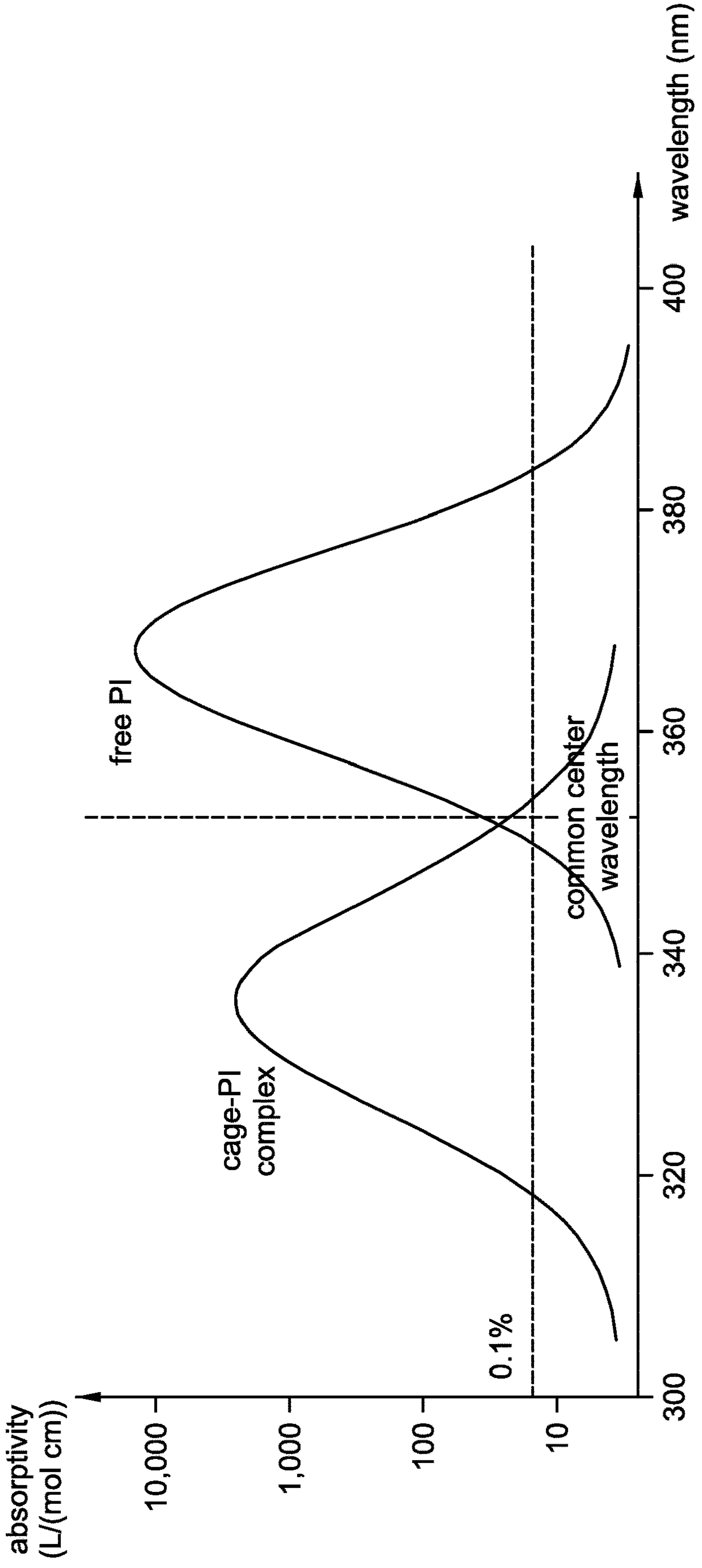

FIGS. 15A-B show that in some LALs 100, the cage-photoinitiator complex 200 has a wavelength-dependent first absorptivity with a first maximum at a first peak wavelength in a range of 250 nm-450 nm; and the free photoinitiator 206*a* has a wavelength-dependent second absorptivity with a second maximum at a second peak wavelength in a range of 250 nm-450 nm. In some LALs 100 the first peak wavelength and the second peak wavelength can both be in the range of 330 nm-380 nm. Having the peak wavelengths shorter than 400 nm is useful in that the intensity of sunlight rapidly decreases below 400 nm, and so a photoinitiator with an absorption maximum below 400 nm is less likely to get activated by the sunlight. On the other hand, commercially available light sources, in particular the modern light emitting diodes, or LEDs, are rare in the wavelength range below 330 nm-350 nm, and even the available ones output light only with too low power.

The activation of such a multiphoton photoinitiator system can be carried out at least in the following two ways. (1) The caged PI 206*c* can be freed from the cage 202 by a first illumination of a first wavelength, followed by activating the free PI 206*a* by a second illumination of a second wavelength. Such systems may carry out both steps well-tuned to the absorption properties of the cage-PI complex 200 and the free PI 206*a*. However, these systems require two light sources with corresponding optics and electronics, which increases both their complexity and their price. (2) It is also possible to use a system with a single light source. Such systems are less well-tuned to the absorption properties of the cage-PI complex 200 and the free PI 206*a*, but are simpler and thus less pricey.

In some detail, in the above type (1) embodiments, where a first center wavelength of the first illumination is different from a second center wavelength of the second illumination, the first center wavelength can be selected such that the first absorptivity of the cage-photoinitiator complex is greater than 1% of the first maximum; and the second center wavelength can be selected such that the second absorptivity of the free photoinitiator is greater than 1% of the second maximum. In general, these embodiments may not use light source wavelengths that are tuned close to the absorption maxima of the cage-PI complex 200 and the free PI 206*a*. The possible reasons for such off-peak tuning include that the absorptivity around the peak can be high, in a range of 5,000-20,000 L/(mol cm), which makes the cage-PI complex 200 and the free PI 206*a* absorb the incoming UV light very efficiently, thus giving rise to a very short penetration depth in the context of Beer's law. In such LALs 100, the UV light of the first and second illumination would not reach into the bulk of the LAL 100 very efficiently, which would reduce the efficiency of the shape and power adjustment of the LAL 100, as well as possibly introduce unwanted strains and mechanical deformations within the LAL 100. For all these reasons, it may be better to tune the wavelength of the first and second illumination to the wings of the absorptivity peaks of the cage-PI complex 200 and the free PI 206*a*, where the absorptivity is small, such as it is in the range of 1-50% of the absorptivity maximum, or in the range of 1-10%, or simply above 1%.

FIG. 15A shows that the same concept of off-peak tuning can be captured in absolute terms as follows. In LALs 100, where the first center wavelength of the first illumination is different from a second center wavelength of the second illumination; the first center wavelength can be selected such that the first absorptivity of the cage-photoinitiator complex 200 is in a range of 50-2,000 L/(mol cm); and the second center wavelength can be selected such that the second absorptivity of the free photoinitiator is in a range of 50-2,000 L/(mol cm). FIG. 15A shows a case where the first absorptivity peak of the cage-PI complex 200 is around 325 nm, yet the first center wavelength of the first illumination is chosen to be around 335 nm, and the second absorptivity peak of the free PI 206*a* is around 375 nm, yet the second center wavelength of the second illumination is chosen to be around 382 nm. Both of these choices place the absorptivity values at the illumination center wavelengths into a range of 50-2,000 L/(mol cm), indicated by dashed lines.

FIG. 15B shows the above type (2) embodiment, where the first and second illuminations are generated by the same illumination source, and therefore have the same single common center wavelength. Such an embodiment can be useful when the absorptivity peaks of the cage-PI complex 200 and the free PI 206*a* overlap to a non-trivial degree, as shown. In such embodiments, the common center wavelength can be selected such that the first absorptivity of the cage-photoinitiator complex 200 at the common center wavelength is at least 0.1% of the first maximum; and the second absorptivity of the free PI 206*a* at the common center wavelength is at least 0.1% of the second maximum. Such a choice of the common center wavelength of about 355 nm is shown in FIG. 15B. Correspondingly, in absolute terms, the common center wavelength can be selected such that the first absorptivity of the cage-photoinitiator complex 200 at the common center wavelength is in a range of 10-5,000 L/(mol cm); and the second absorptivity of the free PI 206*a* at the common center wavelength is in a range of 10-5,000 L/(mol cm).

Of the several design parameters, a number of combinations can have advantages. For example, in some LALs 100 the first peak wavelength of the cage-PI complex 200 can be shorter than the second peak wavelength of the free PI 206*a*. Such LALs 100 have the benefit of the cage-PI 200 is very unlikely to be activated by the sunlight, while the free PI 206*a* can be activated by a second illumination that poses less risk to the retina.

In some embodiments of the LAL 100, the first maximum absorptivity of the cage-photoinitiator complex 200 can be greater than the second absorptivity maximum of the free photoinitiator 206*a*. In such LALs 100 a flash of a first illumination can free the vast majority of the caged PIs 206*c*. Once the PIs 206*c* are uncaged, these LALs 100 function like the previously described LALs, whose PI was not caged in the first place.

Embodiment with the opposite arrangement, i.e. the first maximum absorptivity of the cage-photoinitiator complex 200 being smaller than the second absorptivity maximum of the free photoinitiator 206*a* have the benefit of being relatively safe: the low absorptivity of the cage-PI complex 200 makes it unlikely that inadvertent exposure to the UV portion of sunlight frees caged PIs 206*c*.

In general, the second illumination can have a higher or lower intensity, or power than the first illumination. Also, the second illumination can be started after the first illumination was ended, or possibly before the first illumination was ended, or even simply simultaneously with the first illumination. In the simplest embodiments, where the first and second illuminations are generated by the same light source and thus have the same common center wavelength, the first and second illumination can simply be one and the same single illumination.

The illuminations can also be shaped, i.e. can have an intensity with a radial and possibly an angular dependence, as described earlier in relation to FIG. 1A-F. As far as their time dependence is concerned, the illuminations can be a continuous wave illumination, or an oscillating, or pulsed illumination. As far as their spatial dependence is concerned, the illuminations can be wide beam, or scanning type illuminations.

FIG. 14 also shows that the free photoinitiator 206*a* can be of the Norrish type I or type II. In LALs 100 where the free photoinitiator 206*a* is Norrish type I, after getting activated by the second illumination, the activated PI 206* can be capable of directly inducing the polymerization reaction of the mobile macromer 104. Examples of such polymerization reactions have been described above in the context of Eqs. (2)-(3). The photoinitiators 106, described in relation to FIGS. 4-6 and 10A-B are often such Norrish type I.

FIG. 14 also shows that in LALs 100, where the free photoinitiator 206*a* is Norrish type II, after getting activated by the second illumination, the activated photointiator 206* can be capable of inducing the polymerization reaction of the mobile macromer 104 via activating a contributory initiator 208*a*, a sacrificial hydrogen donor, another free photoinitiator 206*a*, or itself by an intramolecular reaction; wherein the activation can involve the free photoinitiator 206*a* acquiring a hydrogen. It is noted that these Norrish type II initiators do not themselves become activated in the sense of forming a radical even after the absorption of the second photon. Instead, they only form an excited state, which is often a long-lived triplet excited state that is capable of activating the co-initiator 208*a*. The unique nature of the "non-radical activation" of these "activated" Norrish type II PIs 206* is indicated in FIG. 14 by the different, empty activation symbol.

In general, the contributory initiator 208*a* can be an alcohol, an amine, or a hydrosilane, that contained the acquired hydrogen in a labile bond. As an example, such an "activation-by-hydrogen-acquisition" process is described for the free PI 206*a* being a benzophenone as follows:

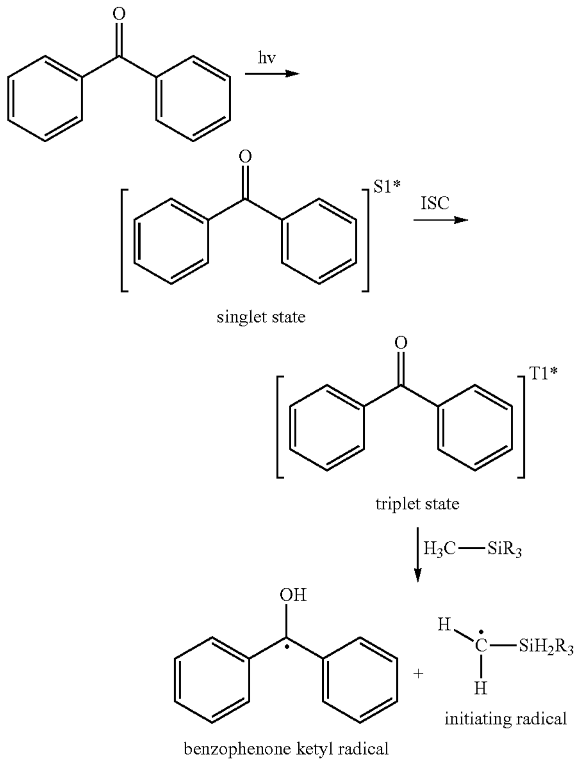

Figure 16B:
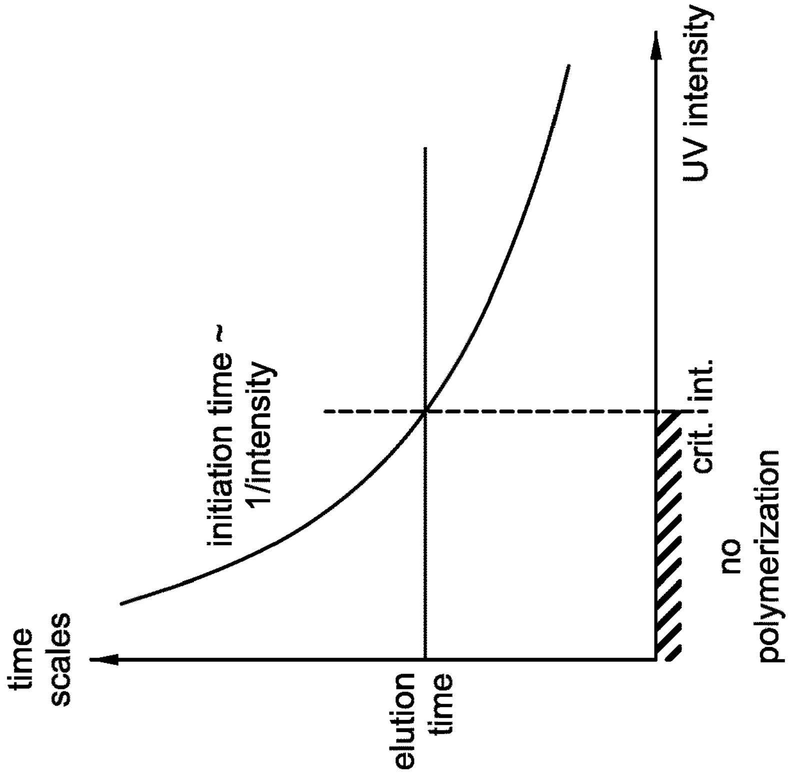
FIGS. 16A-C illustrate different demonstrations of the low intensity cutoff.
Figure 16A:
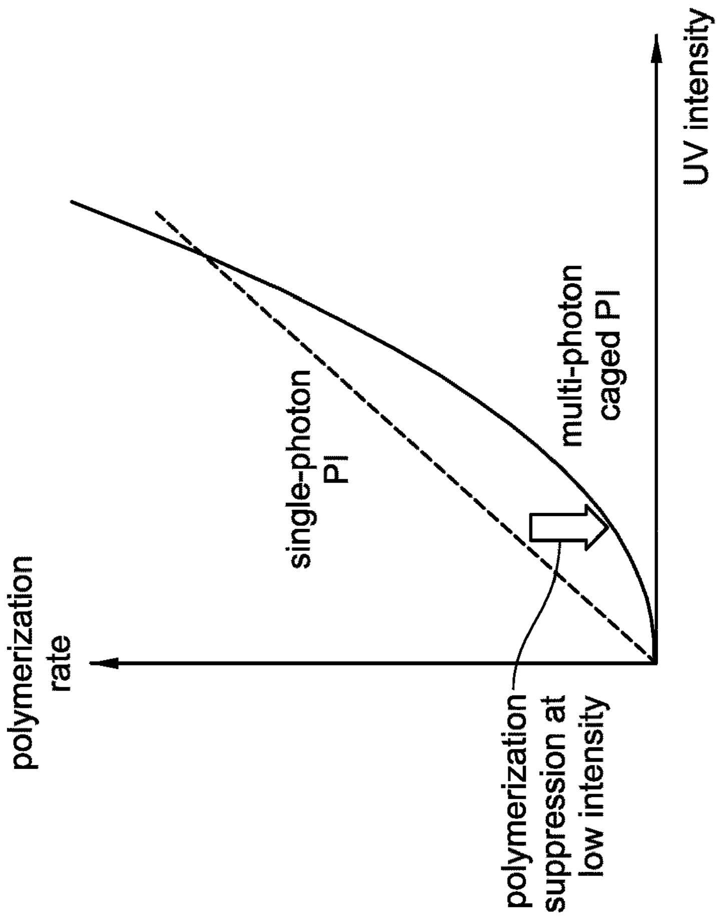
Figure 16C:
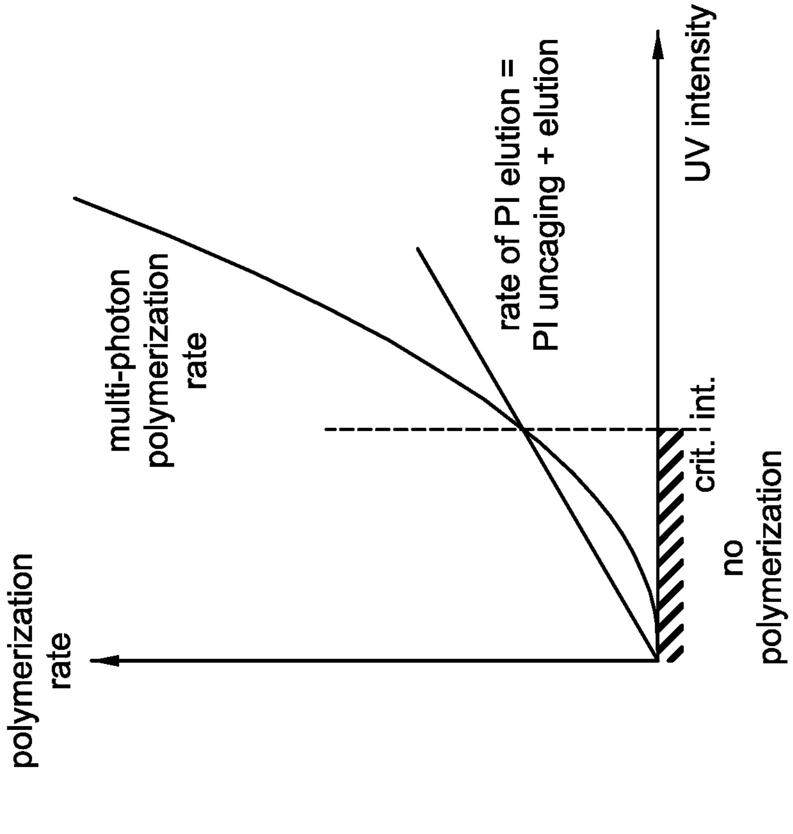

Next, the description returns to the basic principles of operation of these LALs 100. FIGS. 16A-C show the mechanisms and advantages of the LAL 100 on a conceptual level. FIG. 16A shows that the polymerization rate can be suppressed at the low intensities of the ambient sunlight by using a multi-photon PI 206 instead of a more traditional single photon PI, while this choice can keep the polymerization rate high at the high intensities of the adjustment illumination. This suppression is driven by the quadratic dependence of the polymerization rate of multi-photon PIs on the illumination intensity, in contrast to the linear dependence of single photon PIs. This suppression greatly reduces the probability of inadvertent polymerization and thus power shift by ambient sunlight. Therefore, this suppression of the photosensitivity can already greatly reduce the need for a lock-in treatment of such LALs 100. To completely eliminate the need for a lock-in procedure with a wide margin of safety, a further dynamical process of the physical chemistry of the LALs 100 can be implemented and harnessed as follows.

FIG. 16B shows the second concept that turns the suppression of polymerization into the elimination of the polymerization, and thus into the elimination of the need for a lock-in procedure. The concept is to create a low intensity cutoff, below which the already suppressed polymerization is effectively blocked. This low intensity cutoff is achieved by introducing a dynamical process to compete with the initiation of polymerization by the free photoinitiator 206*a*. This competition can be achieved by making the free PI 206*a* hydrophilic. As the mobile free PI 206*a* is diffusively migrating within the LAL 100, when it reaches a surface of the LAL 100, this hydrophilic property makes the PI 206*a* elute from the LAL 100 into the high-water-content aqueous of the eye, and thus will not subsequently initiate any polymerization. To provide quantitative contours, an elution time of the free PI 206*a* can be defined as the time in which at least 80% of the free PI 206*a* elutes out of the LAL 100 into the eye after the implantation of the LAL 100 into the eye and after the freeing of the caged PI 206*c* by the first illumination. This elution time can be in a range of 1 minute-1 month, in other embodiments, in a range of 10 minutes-1 week. To quantitatively set up the definition of the low intensity cutoff, we also define a (polymerization) initiation time, as the time in which the second illumination activates the freed photoinitiator 206*a* that thereby initiates the polymerization reaction of a fixed fraction of the mobile macromers 104. Clearly, the initiation time is inversely proportional to the intensity of the illumination: the stronger the illumination, the shorter time is needed to initiate the polymerization reaction of a fixed fraction of the mobile macromers 104.

FIG. 16B shows that in a low-UV intensity ambient sunlight the initiation time is longer than the elution time, and thus the free PIs 206*a* elute the LAL 100 before they could initiate the polymerization of the mobile macromers 104. This low intensity cutoff therefore effectively blocks the already suppressed polymerization by the ambient sunlight, and thus eliminates the need for a lock-in below a critical intensity, where the two times are equal. In contrast, in the high intensity adjustment illumination (higher than the critical intensity), the initiation time becomes shorter than the elution time, and thus the free PIs 206*a* initiate the polymerization of the mobile macromers 104 before eluting the LAL 100. Thus, the initiation time becoming shorter than the elution time at high intensities enables and preserves the adjustment of the optical power of the LAL 100 with the adjusting illumination.

FIG. 16C illustrates the low intensity cutoff concept in terms of the full (first plus second) illumination, not only starting after the freeing of the PI 206, as FIG. 16B did. Starting with the first illumination, the "rate of PI elution" is a product of the rate of the first illumination uncaging, or freeing the caged PI 206*c*, followed by the free PI 206*a* eluting the LAL 100. Because of the inclusion of the uncaging process, the probability, or "rate of PI elution" is linearly proportional to the intensity. In the case of the LAL 100 being subject to a low intensity ambient sunlight as both the first and the second illumination, the linear rate of PI elution is higher than the quadratic polymerization rate up to a critical intensity. This is a re-expression of the concept of the low intensity cutoff, below which the polymerization is effectively blocked, and thus the need for a lock-in procedure is eliminated. On the other hand, once the intensity exceeds the critical intensity, where the two rates intersected, the polymerization rate exceeds the rate of PI elution, and the LALs 100 became adjustable with the high intensity of an adjusting illumination.

FIGS. 16A-C summarized that in such LALs 100, in the low intensity ambient sunlight the initiation time is longer than the elution time, thereby eliminating the need for a lock-in, whereas in the high intensity adjustment light the initiation time shrinks and become shorter than the elution time. This "lock-in elimination by a low intensity cutoff" concept can be articulated more quantitatively as follows. In LALs 100 when (at least) the second illumination is characterized by the solar spectrum with an intensity less than 10 mW/cm$^2$ in the wavelength range shorter than 400 nm, then the second illumination initiates the polymerization in an initiation time that is longer than the elution time of the free photoinitiator; whereas when the second center wavelength of the second illumination is in a range of 300-400 nm with an average intensity greater than 30 mW/cm$^2$, then the second illumination initiates the polymerization in an initiation time that is shorter than the elution time of the free photoinitiator, wherein the initiation time is a time in which the second illumination activates the free photoinitiator that thereby initiates the polymerization reaction with at least a 10% polymerization rate.

Figure 17:
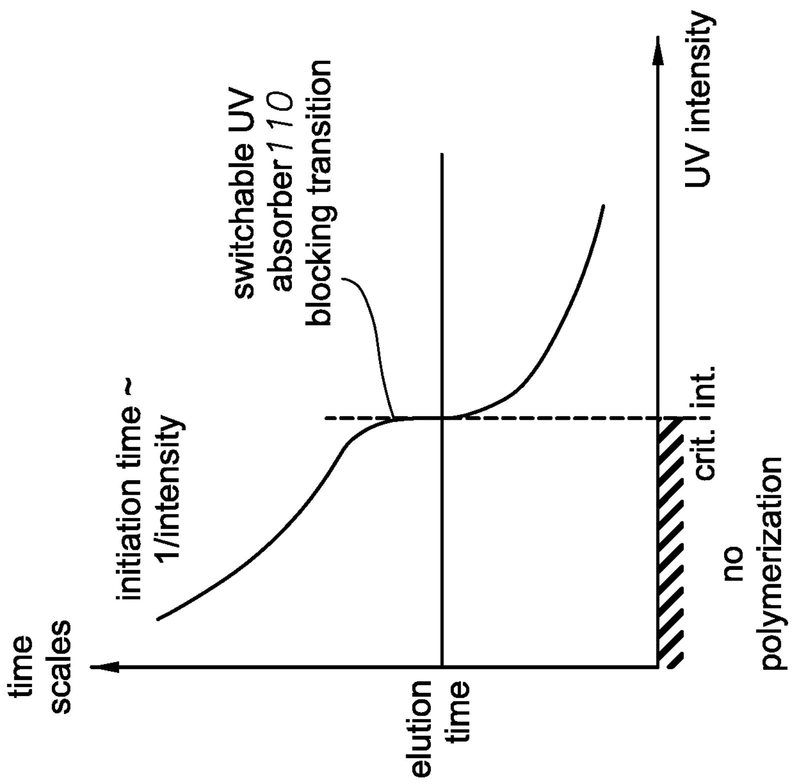
FIG. 17 shows the change in the construction of the low intensity cutoff in the presence of a switchable UV absorber front protection layer.

A few qualifiers are added to this description. First, the rate of polymerization can be defined as the product of the molar absorptivity of the free photoinitiator 206*a* times the quantum efficiency of the polymerization reaction. Second, some embodiments may have a switchable front protection UV absorber layer 110. The presence of such a front protection layer 110 modifies the above numerical values and dynamical balances. Especially so, if the switchable front protection layer 110 is in a blocking configuration for the low intensity sunlight, but switches to a non-blocking configuration for the high intensity adjustment light. An example is shown in FIG. 17, which demonstrates that the switching transition of the front protection UV absorber layer 110 can amplify the differences between the two intensity regimes: the low intensity regime, where the initiation time much exceeds the elution time, switching to the high intensity regime at a critical intensity because the switching absorber layer 110 ceases to block the UV illumination, where the initiation time becomes much shorter than the elution time. The actual value of this low intensity cutoff is strongly impacted by the relative spectral weights of the shorter than 400 nm and the longer than 400 nm wavelength components of the low intensity light.

Third, as described above, this polymerization initiation time is sensitive to the oxygen content on the LAL 100. As demonstrated in FIGS. 6B, 7 and 8, the activated photoinitiator 206* has a much higher affinity toward oxygen than toward the mobile macromers 104. Therefore, as the second UV illumination is applied, the activated PI 206* will react with the available oxygens rather than with the mobile macromer 104 and therefore will not initiate polymerization until the oxygen is not consumed. The above introduced initiation time does include the time needed to consume the oxygen, followed by initiating the polymerization of the mobile macromer 104. Fourth, in the important embodiment when the first and second illumination are a single, simultaneous and combined illumination, the above intensity values of 10 and 30 mW/cm$^2$ characterize the total intensity of the combined illumination.

The above design concept of eliminating the need for a lock-in can be realized with other classes of photoinitiators as well. The free PI 206*a* may become unable to initiate polymerization by another mechanism as well: by being thermally unstable and dissociating over a dissociation time. In such LALs 100, the competition of the dissociation time and the initiation time can be used to eliminate the need for a lock-in. In some detail, when the second illumination are characterized by the solar spectrum with an intensity less than 10 mW/cm$^2$ in the wavelength range shorter than 400 nm, then these illuminations initiate the polymerization in an initiation time that is longer than a dissociation time of the free photoinitiator; and when the first center wavelength of the first illumination and the second center wavelength of the second illumination are in a range of 300-400 nm range with an average intensity greater than 30 mW/cm$^2$, then these illuminations initiate the polymerization in an initiation time that is shorter than the dissociation time of the free photoinitiator, wherein the free photoinitiator is thermally unstable, and thereby has the dissociation time in which at least 80% of the free photoinitiator dissociates after implantation of the LAL into the eye; the initiation time is a time in which the free photoinitiator absorbs a photon and initiates the polymerization reaction with at least a 10% polymerization rate; and the dissociation time is in a range of 1 minute-1 month.

Next, several specific examples of the cage-photoinitiator complex 200 and the free photoinitiator 206*a* pairs will be described expressly.

EXAMPLE 1

In some embodiments of the LAL 100, the cage-photoinitiator complex 200 is 5-hydroxy-2,2-diphenyl-4H-benzo-[1,3]dioxinone (a.k.a. caged benzophenone (BP)); and the free photoinitiator 206*a* is benzophenone (BP).

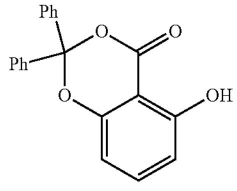

cage-PI complex 200

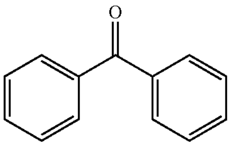

free PI 206a

Figure 18:
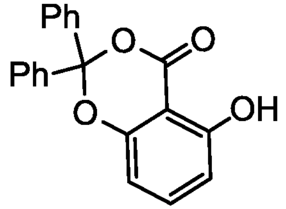
FIG. 18 shows the chemical composition and the absorptivity of the cage-photoinitiator complex and the free photoinitiator in Example 1.
Figure 18:
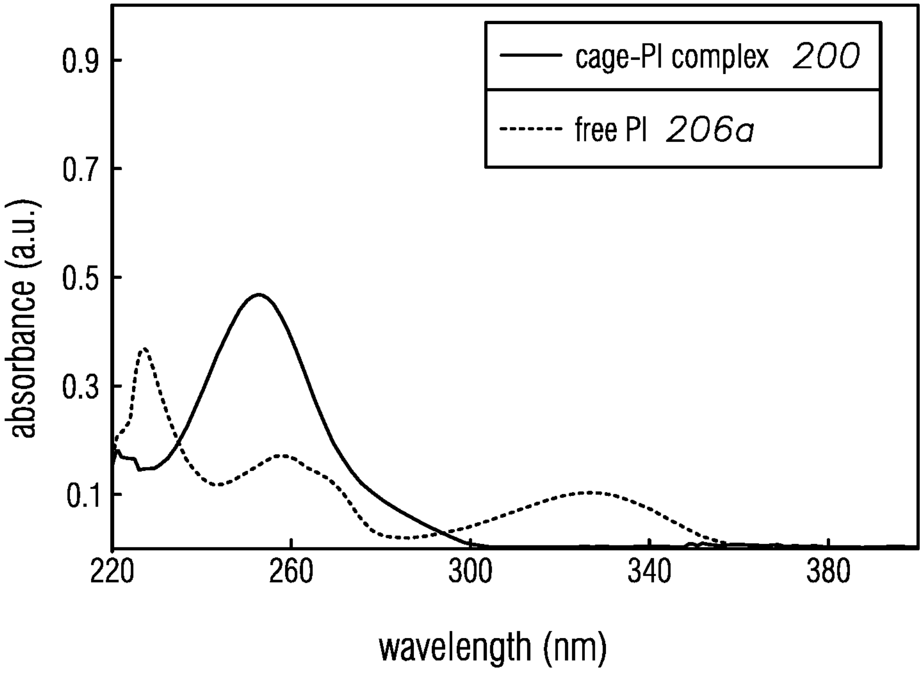
Figure 18:
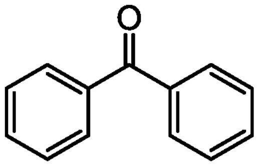

This cage-photo initiator complex 200 was synthesized according to the previously described procedure of M. A. Tasdelen et al., *Polymer* 47 (2006) 7611-7614. In a typical procedure, to a flask containing 20 mL of 0.8M solution of dihydroxybenzoic acid, DMAP (0.192 g, 1.6 mmol) and benzophenone (4.37 g, 24 mmol) were added. The reaction mixture was cooled to 0° C under $N_2$, followed by the dropwise addition of thionyl chloride (1.74 mL, 24 mmol). The reaction was brought to room temperature and stirred for 18 hours after which the volatiles were removed by rotary evaporation. Crude mixture was purified using column chromatography (5/95, EtOAc/Hex). Yield: 17%, 1H NMR (600 MHz, CDCl3): δ 10.13 (s, 1H), 7.61-7.55 (m, 4H), 7.42-7.32 (m, 7H), 6.65 (d, J=8.1 Hz, 1H), 6.56 (d, J=8.4 Hz, 1H). 13C NMR (151 MHz, CDCl3) δ 165.7, 161.6, 156.1, 139.2, 138.2, 129.6, 128.8, 126.6, 111.3, 107.7, 107.6, 101. The wavelength-dependent absorbances of these compounds are shown in FIG. 18.

EXAMPLE 2

In some embodiments of the LAL 100, the cage-photoinitiator complex 200 is 2-(benzo-[1,3]dioxolyl)-5-hydroxy-2-phenyl-4H-benzo[d][1,3]dioxinone (a.k.a. caged phenyl benzodioxole (PBD)); and the free photo-initiator 206*a* is benzo[d][1,3]dioxolyl (phenyl) methanone (a.k.a. phenyl benzodioxole (PBD)):

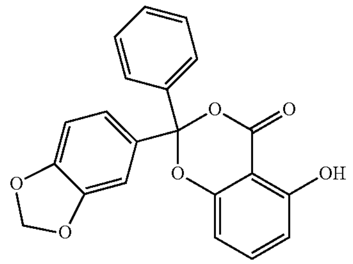

cage-PI complex 200

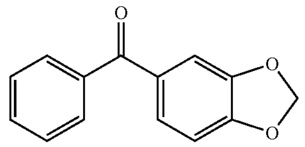

free PI 206a

Figure 19:
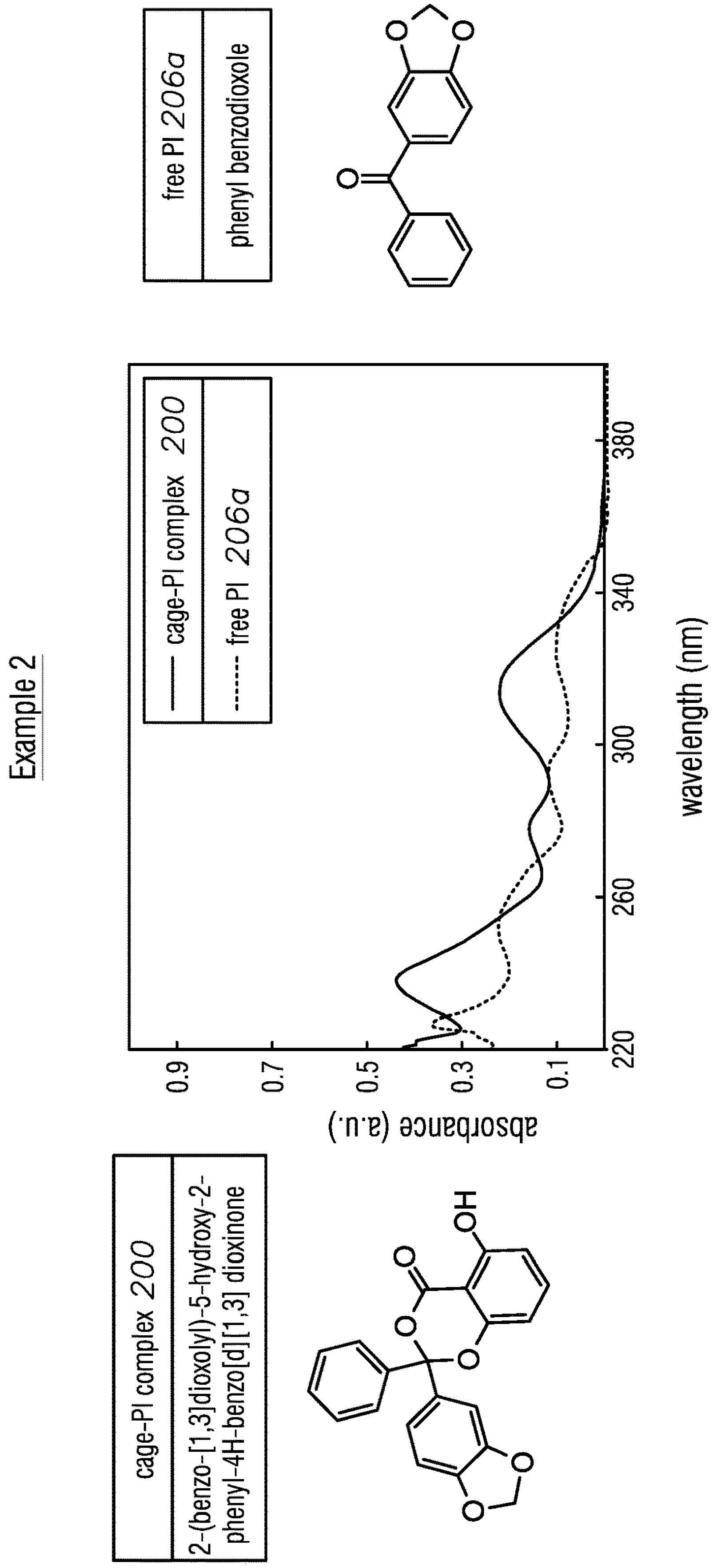
FIG. 19 shows the chemical composition and the absorptivity of the cage-photoinitiator complex and the free photoinitiator in Example 2.

This cage-photoinitiator complex 200 was synthesized from a commercially available precursor (PBD) according to the procedure referenced above. Yield: 55%, 1H NMR: (499 MHZ, CDCl3) δ 10.14 (s, 1H), 7.59-7.55 (m, 2H), 7.41-7.32 (m, 4H), 7.05-7.01 (m, 2H), 6.77-6.73 (m, 1H), 6.63 (dd, J=8.1, 0.9 Hz, 1H), 6.57 (dd, J=8.5, 0.9 Hz, 1H), 5.95-5.93 (m, 2H). 13C NMR (126 MHz, CDCl3) δ 165.7, 161.6, 156.1, 148.6, 148.1, 139.2, 138.2, 133.1, 129.6, 128.7, 126.5, 120.9, 111.3, 108.2, 107.63, 107.56, 107.4, 101.6, 101.0. The wavelength-dependent absorbances of these compounds are shown in FIG. 19.

EXAMPLE 3

In some embodiments of the LAL 100, the cage-photoinitiator complex 200 is 5-hydroxy-2-(naphthalenyl)-2 phenyl-4H-benzo-dioxinone (a.k.a. caged NPM); and the free photoinitiator 206*a* is 2-naphthalenyl phenylmethanone (NPM).

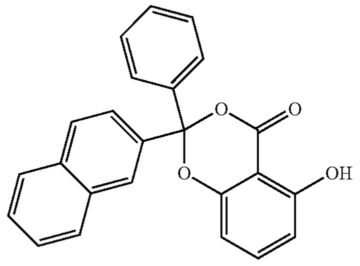

cage-PI complex 200

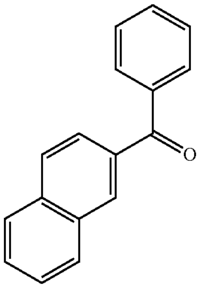

free PI 206a

Figure 20:
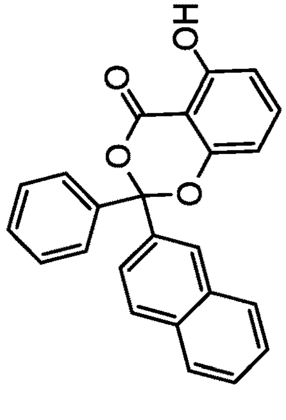
FIG. 20 shows the chemical composition and the absorptivity of the cage-photoinitiator complex and the free photoinitiator in Example 3.
Figure 20:
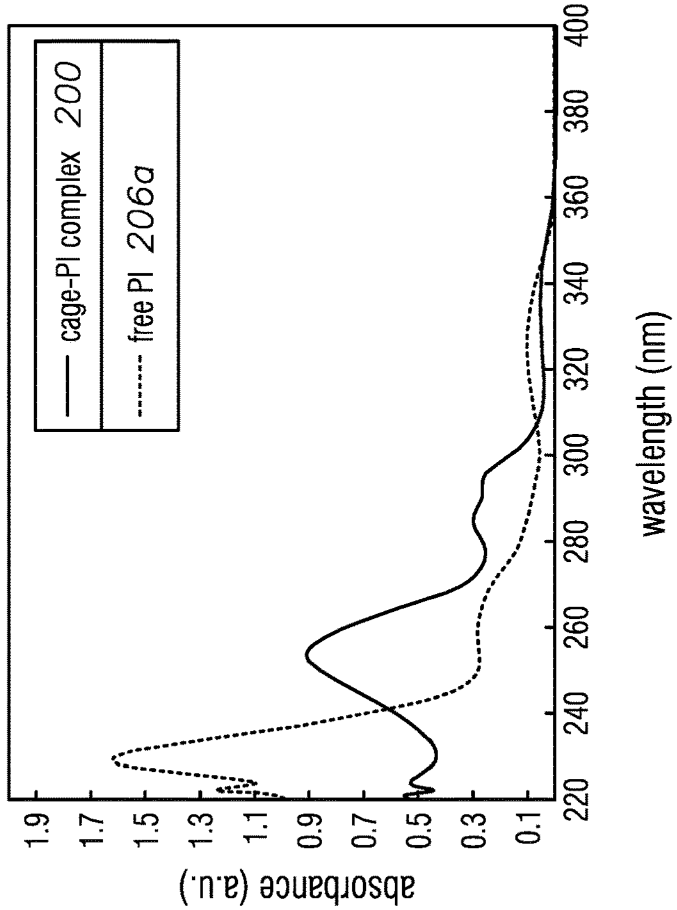
Figure 20:
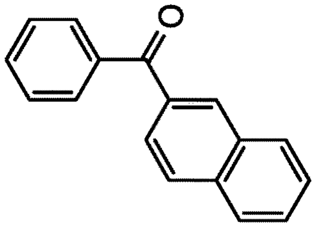

This cage-photoinitiator complex 200 was synthesized from a commercially available precursor (NPM) according to the procedure referenced above. Yield: 23%, 1H NMR (600 MHZ, CDCl3) δ 10.16 (s, 1H), 8.08 (br. s, 1H), 7.90-7.80 (m, 3H), 7.69 (dd, J=8.7, 1.9 Hz, 1H), 7.68-7.63 (m, 2H), 7.52 (qd, J=6.6, 3.4 Hz, 2H), 7.44-7.34 (m, 4H), 6.71 (d, J=8.2 Hz, 1H), 6.57 (d, J=8.4 Hz, 1H). 13C NMR (151 MHZ, CDCl3) δ 165.7, 161.6, 156.1, 139.2, 138.3, 136.5, 133.5, 132.7, 129.6, 128.9, 128.8, 127.8, 127.3, 126.8, 126.7, 126.4, 123.7, 111.4, 107.9, 107.6, 101.1 The wavelength-dependent absorbances of these compounds are shown in FIG. 20.

EXAMPLE 4

In some embodiments of the LAL 100, the cage-photoinitiator complex 200 is caged 9-anthracenyl (phenyl) methanone (a.k.a. caged APM); and the free photoinitiator **206*a*** is 9-anthracenyl (phenyl) methanone (APM). Due to unfavorable absorption profile of APM, the caged complex of APM was not pursued.

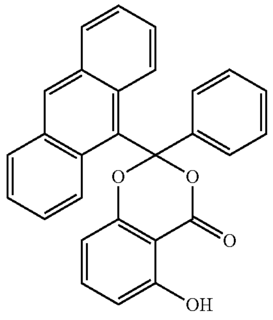

cage-PI complex 200

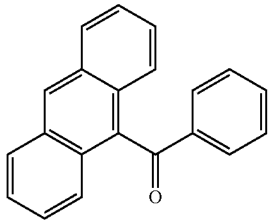

free PI 206a

Figure 21:
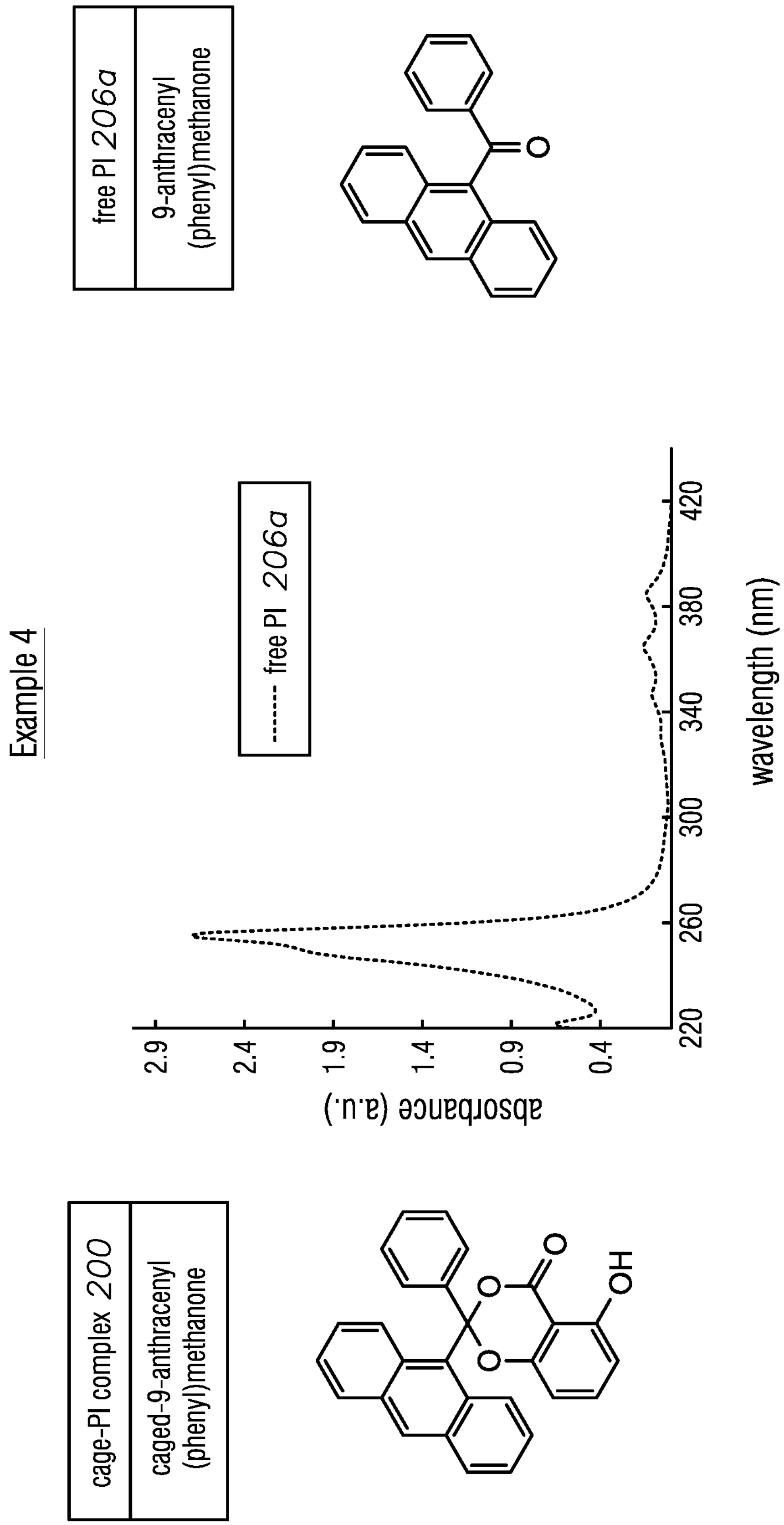
FIG. 21 shows the chemical composition and the absorptivity of the cage-photoinitiator complex and the free photoinitiator in Example 4.

The wavelength-dependent absorbance of commercially available APM is shown in FIG. 21.

EXAMPLE 5

In some embodiments of the LAL 100, the cage-photoinitiator complex 200 is 2-(4-(diphenylamino)phenyl)-5-hydroxy-2-phenyl-4H-benzo[d][1,3]dioxinone (a.k.a. caged DPABP); and the free photoinitiator is 4-diphenylamino benzophenone (DPABP).

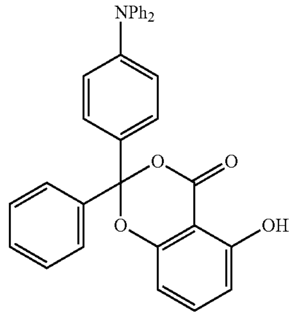

cage-PI complex 200

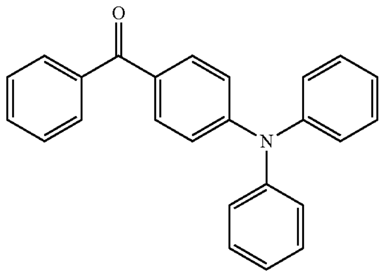

free PI 206a

DPABP was synthesized according to the previously described procedure of T. L. Huang et al., *J. Polymer Science,* 58 (2020) 2914-2925. A mixture of 4-bromobenzophenone (1.93 g, 7.40 mmol), diphenylamine (1.25 g, 7.40 mmol), sodium tert-butoxide (1.07 g, 11.1 mmol), bis (dibenzylideneacetone) palladium(0) (0.085 g, 0.147 mmol), and tri-tert-butylphosphine (0.06 ml, 0.31 mmol, 50% wt. in toluene) were dissolved in dry toluene (15 mL) under nitrogen and heated to 95° C overnight. After cooling, the reaction mixture was poured into dichloromethane (100 mL) and washed with water (100 mL). The organic phase was filtered through a cotton plug and subsequently dried with sodium sulfate. The solution was then concentrated in vacuo to yield the crude product as an orange solid. The crude product was purified by recrystallization from ethanol to yield the purified product as a pale-yellow solid (2.11 g, 82% yield). 1H NMR (600 MHz, CDCl3) δ 7.80-7.74 (m, 2H), 7.73-7.68 (m, 2H), 7.57-7.52 (m, 1H), 7.46 (t, J=7.6 Hz, 2H), 7.36-7.30 (m, 4H), 7.21-7.17 (m, 4H), 7.17-7.11 (m, 2H), 7.02 (d, J=8.5 Hz, 2H). 13C NMR (151 MHz, CDCl3) δ 195.3, 152.1, 146.6, 138.6, 132.1, 131.8, 129.78, 129.75, 129.7, 128.3, 126.1, 124.8, 119.7.

Figure 22:
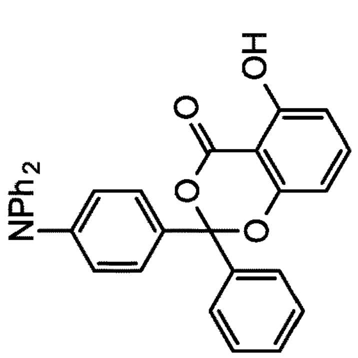
FIG. 22 shows the chemical composition and the absorptivity of the cage-photoinitiator complex and the free photoinitiator in Example 5.
Figure 22:
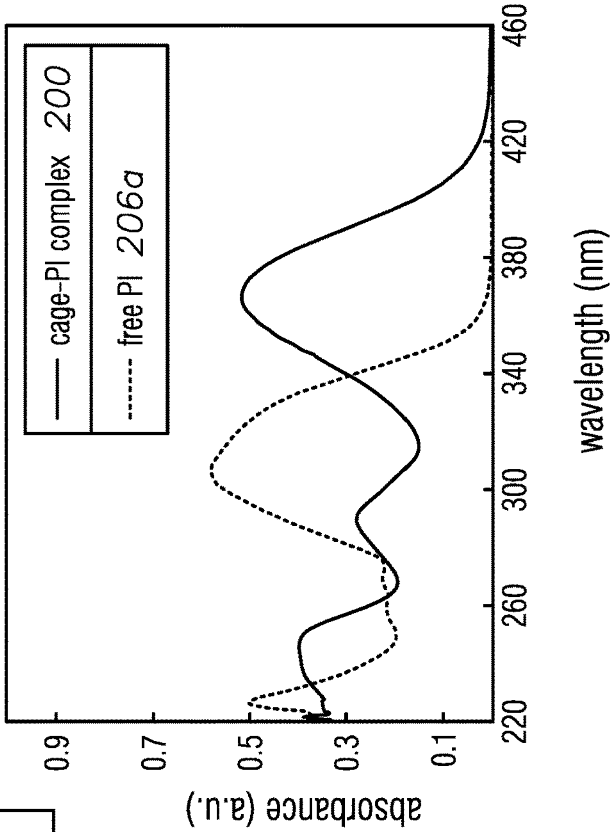
Figure 22:
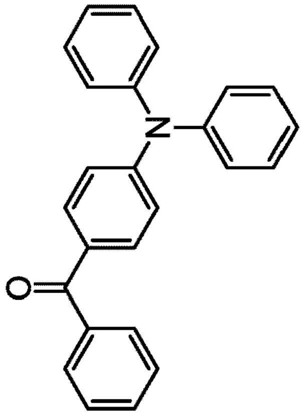

The caged version of DPABP was prepared according to the procedure referenced earlier by M. A. Tasdelen et al., *Polymer* 47 (2006) 7611-7614. Yield: 78%, 1H NMR (600 MHZ, CDCl3) δ 10.18 (s, 1H), 7.62-7.56 (m, 2H), 7.42-7.32 (m, 6H), 7.28-7.23 (m, 4H), 7.12-7.07 (m, 4H), 7.05 (td, J=7.3, 1.2 Hz, 2H), 7.01-6.96 (m, 2H), 6.62 (d, J=8.1 Hz, 1H), 6.57 (d, J=8.4 Hz, 1H). 13C NMR (151 MHz, CDCl3) δ 165.9, 161.6, 156.3, 149.0, 147.2, 139.2, 138.2, 138.0, 131.8, 129.52, 129.48, 129.2, 128.7, 128.4, 127.6, 126.8, 125.4, 125.3, 123.9, 121.6, 111.2, 108.0, 107.6, 101.1. The wavelength-dependent absorbances of these compounds are shown in FIG. 22.

While this document contains many specifics, details and numerical ranges, these should not be construed as limitations of the scope of the invention and of the claims, but, rather, as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to another subcombination or a variation of a subcombinations.

The invention claimed is:

1. A Light Adjustable Lens (LAL), comprising:
a polymer silicone network, molded in the presence of a mobile macromer and an ultraviolet absorber;
a cage-photoinitiator complex; wherein a caged photoinitiator can be freed from a cage by a first photon of a first illumination;
the free photoinitiator can be activated by a second photon of a second illumination; and
the activated photoinitiator is capable of inducing a polymerization reaction of the mobile macromer, leading to a changing of an optical power of the LAL; and
a front protection layer, including a switchable ultraviolet absorber.

2. The LAL of claim 1, wherein
the polymerization reaction includes grafting a mobile macromer onto the polymer silicone network, or bonding to another mobile macromer, wherein the bonded macromers eventually entangle with the polymer silicone network.

3. The LAL of claim 1, wherein:
the photoinitiator is freed from the cage by the first illumination into a mobile state without activation.

4. The LAL of claim 1, wherein:
the cage-photoinitiator complex has a wavelength-dependent first absorptivity with a first maximum at a first peak wavelength in a range of 250 nm-450 nm; and
the free photoinitiator has a wavelength-dependent second absorptivity with a second maximum at a second peak wavelength in a range of 250 nm-450 nm.

5. The LAL of claim 4, wherein:
the first peak wavelength and the second peak wavelength are both in a range of 330 nm-380 nm.

6. The LAL of claim 4, wherein:
a first center wavelength of the first illumination is different from a second center wavelength of the second illumination;
the first center wavelength is selected such that the first absorptivity of the cage-photoinitiator complex is greater than 1% of the first maximum; and
the second center wavelength is selected such that the second absorptivity of the free photoinitiator is greater than 1% of the second maximum.

7. The LAL of claim 4, wherein:
a first center wavelength of the first illumination is different from a second center wavelength of the second illumination;
the first center wavelength IS selected such that the first absorptivity of the cage-photoinitiator complex is in a range of 50-2,000 L/(mol cm); and
the second center wavelength is selected such that the second absorptivity of the free photoinitiator is in a range of 50-2,000 L/(mol cm).

8. The LAL of claim 4, wherein:
the first illumination and the second illumination are generated by the same illumination source with a common center wavelength.

9. The LAL of claim 8, wherein:
the common center wavelength is selected such that
the first absorptivity of the cage-photoinitiator complex at the common center wavelength is at least 0.1% of the first maximum; and
the second absorptivity of the free photoinitiator at the common center wavelength is at least 0.1% of the second maximum.

10. The LAL of claim 8, wherein:
the common center wavelength is selected such that
the first absorptivity of the cage-photoinitiator complex at the common center wavelength is in a range of 10-5,000 L/(mol cm); and
the second absorptivity of the free photoinitiator at the common center wavelength is in a range of 10-5,000 L/(mol cm).

11. The LAL of claim 4, wherein:
the first peak wavelength is shorter than the second peak wavelength.

12. The LAL of claim 4, wherein:
the first maximum absorptivity of the cage-photoinitiator complex is greater than the second absorptivity maximum of the free photoinitiator.

13. The LAL of claim 4, wherein:
the first maximum absorptivity of the cage-photoinitiator complex is smaller than the second absorptivity maximum of the free photoinitiator.

14. The LAL of claim 1, wherein
the free photoinitiator is Norrish type I, and thereby, after getting activated by the second illumination, the activated photoinitiator is capable of directly inducing the polymerization reaction of the mobile macromer.

15. The LAL of claim 1, wherein
the free photoinitiator is Norrish type II, and thereby, after getting activated by the second illumination, the activated photoinitiator is capable of inducing the polymerization reaction of the mobile macromer via activating one of a contributory initiator, a sacrificial hydrogen donor, another free photoinitiator, or itself by an intramolecular reaction;
wherein
the activation involves the free photoinitiator acquiring a hydrogen.

16. The LAL of claim 15, wherein:
the contributory initiator is one of an alcohol, an amine, or a hydrosilane that contained the acquired hydrogen in a labile bond.

17. The LAL of claim 1, wherein:
the free photoinitiator is hydrophilic and thereby has an elution time in which at least 80% of the free photoinitiator elutes out of the LAL into an eye after implantation of the LAL into the eye and after the freeing of the caged photoinitiator by the first illumination; wherein
the elution time is in a range of 1 minute-1 month.

18. The LAL of claim 17, wherein:
the elution time is in a range of 10 minutes-1 week.

19. The LAL of claim 17, wherein:
when the second illumination is characterized by the solar spectrum with an intensity less than 10 $mW/cm^2$ in the wavelength range shorter than 400 nm, then the second illumination initiates the polymerization in an initiation time that is longer than the elution time of the free photoinitiator; and when the second center wavelength of the second illumination is in a range of 300-400 nm with an average intensity greater than 30 $mW/cm^2$, then the second illumination initiates the polymerization in an initiation time that is shorter than the elution time of the free photoinitiator; wherein the initiation time is a time in which the second illumination activates the free photoinitiator that thereby initiates the polymerization reaction with at least a 10% polymerization rate.

20. The LAL of claim 1, wherein:

when the first and the second illumination are characterized by the solar spectrum with an intensity less than 10 $mW/cm^2$ in the wavelength range shorter than 400 nm, then these illuminations initiate the polymerization in an initiation time that is longer than a dissociation time of the free photoinitiator; and when the first center wavelength of the first illumination and the second center wavelength of the second illumination are in a range of 300-400 nm range with an average intensity greater than 30 $mW/cm^2$, then these illuminations initiate the polymerization in an initiation time that is shorter than the dissociation time of the free photoinitiator; wherein the free photoinitiator is thermally unstable, and thereby has the dissociation time in which at least 80% of the free photoinitiator dissociates after implantation of the LAL into the eye; the initiation time is a time in which the free photoinitiator absorbs a photon and initiates the polymerization reaction with at least a 10% polymerization rate; and the dissociation time is in a range of 1 minute-1 month.

21. The LAL of claim 1, wherein:

the cage-photoinitiator complex is 5-hydroxy-2,2-diphenyl-4H-benzo-[1,3]dioxinone (caged benzophenone (BP)):

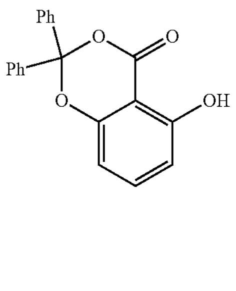 [SMILES: O=C1OC(c2ccccc2)(c2ccccc2)Oc2cccc(O)c21]

and the free photoinitiator is benzophenone (BP):

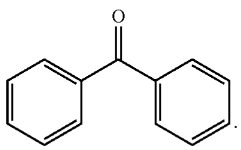 [SMILES: O=C(c1ccccc1)c1ccccc1]

22. The LAL of claim 1, wherein:

the cage-photoinitiator complex is 2-(benzo-[1,3]dioxolyl)-5-hydroxy-2-phenyl-4H-benzo[d][1,3]dioxinone (caged phenyl benzodioxole (PBD)):

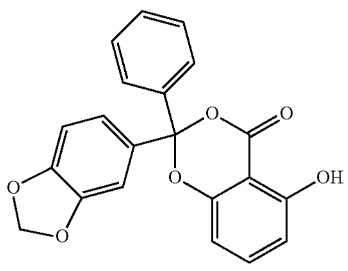 [SMILES: O=C1OC(c2ccccc2)(c2ccc3c(c2)OCO3)Oc2cccc(O)c21]

and the free photoinitiator is benzo[d][1,3]dioxolyl(phenyl)methanone (phenyl benzodioxole (PBD)):

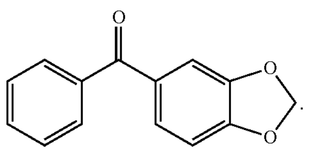 [SMILES: O=C(c1ccccc1)c1ccc2c(c1)OCO2]

23. The LAL of claim 1, wherein:

the cage-photoinitiator complex is 5-hydroxy-2-(naphthalenyl)-2 phenyl-4H-benzo-dioxinone (caged NPM)

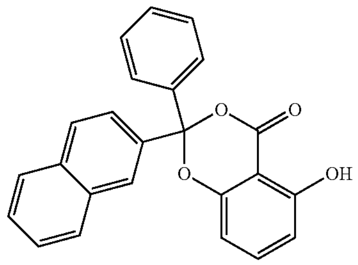 [SMILES: O=C1OC(c2ccccc2)(c2ccc3ccccc3c2)Oc2cccc(O)c21]

and the free photoinitiator is 2-naphthalenyl phenylmethanone (NPM)

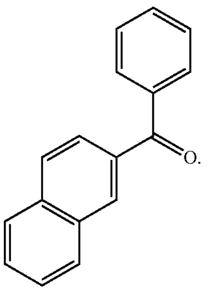 [SMILES: O=C(c1ccccc1)c1ccc2ccccc2c1]

24. The LAL of claim 1, wherein:

the cage-photoinitiator complex is caged 9-anthracenyl (phenyl) methanone (caged APM):

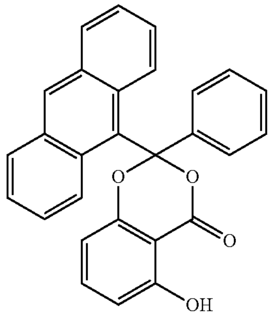 [SMILES: O=C1OC(c2ccccc2)(c2c3ccccc3cc3ccccc23)Oc2cccc(O)c21]

and the free photoinitiator is 9-anthracenyl (phenyl) methanone (APM):

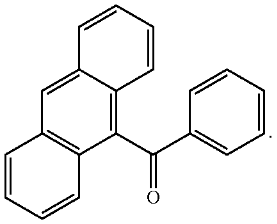 [SMILES: O=C(c1ccccc1)c1c2ccccc2cc2ccccc12]

25. The LAL of claim 1, wherein:

the cage-photoinitiator complex is 2-(4-(diphenylamino) phenyl)-5-hydroxy-2-phenyl-4H-benzo[d][1,3] dioxinone (caged DPABP):

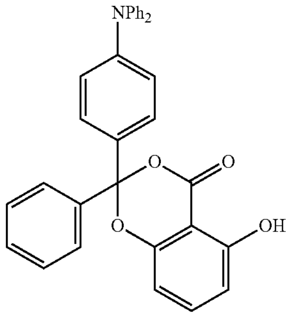

and the free photoinitiator is 4-diphenylamino benzophenone (DPABP):

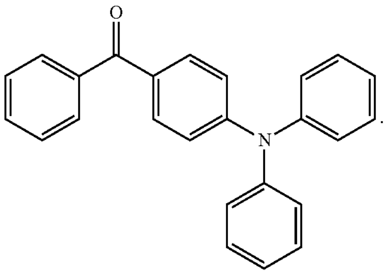 [SMILES: O=C(c1ccccc1)c1ccc(N(c2ccccc2)c2ccccc2)cc1]

* * * * *